US011603410B2

(12) United States Patent
Gaudreau et al.

(10) Patent No.: US 11,603,410 B2
(45) Date of Patent: Mar. 14, 2023

(54) IMMUNOSTIMULATORY AGONISTIC ANTIBODIES FOR USE IN TREATING CANCER

(71) Applicant: Bristol-Myers Squibb Company, Princeton, NJ (US)

(72) Inventors: Marie-Claude Gaudreau, San Mateo, CA (US); Chan Gao, Redwood City, CA (US); Michael Quigley, Ambler, PA (US); Praveen Aanur, Princeton, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 112 days.

(21) Appl. No.: 16/760,776

(22) PCT Filed: Nov. 1, 2018

(86) PCT No.: PCT/US2018/058704
§ 371 (c)(1),
(2) Date: Apr. 30, 2020

(87) PCT Pub. No.: WO2019/089921
PCT Pub. Date: May 9, 2019

(65) Prior Publication Data
US 2020/0369777 A1 Nov. 26, 2020

Related U.S. Application Data

(60) Provisional application No. 62/657,616, filed on Apr. 13, 2018, provisional application No. 62/628,207, filed on Feb. 8, 2018, provisional application No. 62/583,808, filed on Nov. 9, 2017, provisional application No. 62/581,905, filed on Nov. 6, 2017, provisional application No. 62/581,441, filed on Nov. 3, 2017, provisional application No. 62/580,346, filed on Nov. 1, 2017.

(51) Int. Cl.
| | |
|---|---|
| *C07K 16/28* | (2006.01) |
| *A61P 35/00* | (2006.01) |
| *A61K 9/00* | (2006.01) |
| *G01N 33/574* | (2006.01) |
| *A61K 39/00* | (2006.01) |

(52) U.S. Cl.
CPC ........ *C07K 16/2878* (2013.01); *A61K 9/0019* (2013.01); *A61P 35/00* (2018.01); *C07K 16/2827* (2013.01); *G01N 33/57492* (2013.01); *A61K 2039/505* (2013.01); *A61K 2039/507* (2013.01); *A61K 2039/54* (2013.01); *A61K 2039/545* (2013.01); *C07K 2317/565* (2013.01); *C07K 2317/75* (2013.01); *C07K 2317/94* (2013.01); *G01N 2500/04* (2013.01); *G01N 2800/52* (2013.01)

(58) Field of Classification Search
CPC ............ C07K 16/2878; C07K 16/2827; A61K 9/0019; G01N 33/57492
See application file for complete search history.

(56) References Cited

U.S. PATENT DOCUMENTS

| | | | | |
|---|---|---|---|---|
| 9,644,032 | B2 * | 5/2017 | Cai | .................... C07K 16/3069 |
| 2004/0197328 | A1 * | 10/2004 | Young | .................... C07K 16/00 |
| | | | | 424/155.1 |
| 2016/0355597 | A1 | 12/2016 | Rhee et al. | |
| 2017/0306035 | A1 | 10/2017 | Cai et al. | |

FOREIGN PATENT DOCUMENTS

WO    WO-2019089921 A1    5/2019

OTHER PUBLICATIONS

Almagro & Fransson, Humanization of antibodies, Frontiers in Bioscience 2008; 13: 1619-33 (Year: 2008).*
Rudikoff et al., Single amino acid substitution altering antigen-binding specificity, PNAS, USA, 1982, 79: 1979-1983 (Year: 1982).*
Riemer et al., Matching of trastuzumab (Herceptin®) epitope mimics onto the surface of Her-2/neu—a new method of epitope definition, Mol Immunol, 2005 42(9): 1121-1124 (Year: 2005).*
Gura, T., Systems for Identifying New Drugs Are Often Faulty, Science, 1997, 278:1041-1042 (Year: 1997).*
Kaiser, J., First pass at cancer genoome reveals complex landscape, Science, 2006, 313:1370 (Year: 2006).*
Chames et al., Therapeutic antibodies: successes, limitations and hopes for the future, British J. of Pharmacology, 2009, 157, 220-233 (Year: 2009).*
International Search Report and Written Opinion dated May 9, 2019, International Application No. PCT/US2018/058704, EPO, Netherlands, 20 pages.
De Vos, S., et al., "A phase II study of dacetuzumab (SGN-40) in patients with relapsed diffuse large B-cell lymphoma (DLBCL) and correlative analyses of patient-specific factors," Journal of Hematology & Oncology (7)12: 44, Biomed Central, England (Jun. 2014).

(Continued)

*Primary Examiner* — Peter J Reddig
*Assistant Examiner* — Cheng Lu
(74) *Attorney, Agent, or Firm* — Sterne, Kessler, Goldstein and Fox PLLC

(57) ABSTRACT

Provided herein are methods of treating cancer using agonistic antibodies that specifically bind to immunostimulatory receptors, wherein the antibodies are administered in an amount and/or frequency sufficient to achieve and/or maintain a receptor occupancy of less than about 80%, for example, a receptor occupancy of about 20% to about 80%. Also provided are methods of determining human doses for such agonistic antibodies, and methods for monitoring receptor occupancy of the agonistic antibodies in order to maintain effective antibody levels in, e.g., human patients. Also provided are methods of measuring soluble OX40 in a subject. Also provided are methods of treating cancer, comprising administering to the subject an effective amount of each of an anti-OX40 antibody and an anti-PD-1 antibody.

20 Claims, 68 Drawing Sheets

Specification includes a Sequence Listing.

(56) References Cited

OTHER PUBLICATIONS

Vonderheide, R., et al., "Clinical activity and immune modulation in cancer patients treated with CP-870,893, a novel CD40 agonist monoclonal antibody," Journal of Clinical Oncology 25(7): 876-883, American Society of Clinical Oncology, United States (Mar. 2007).

* cited by examiner

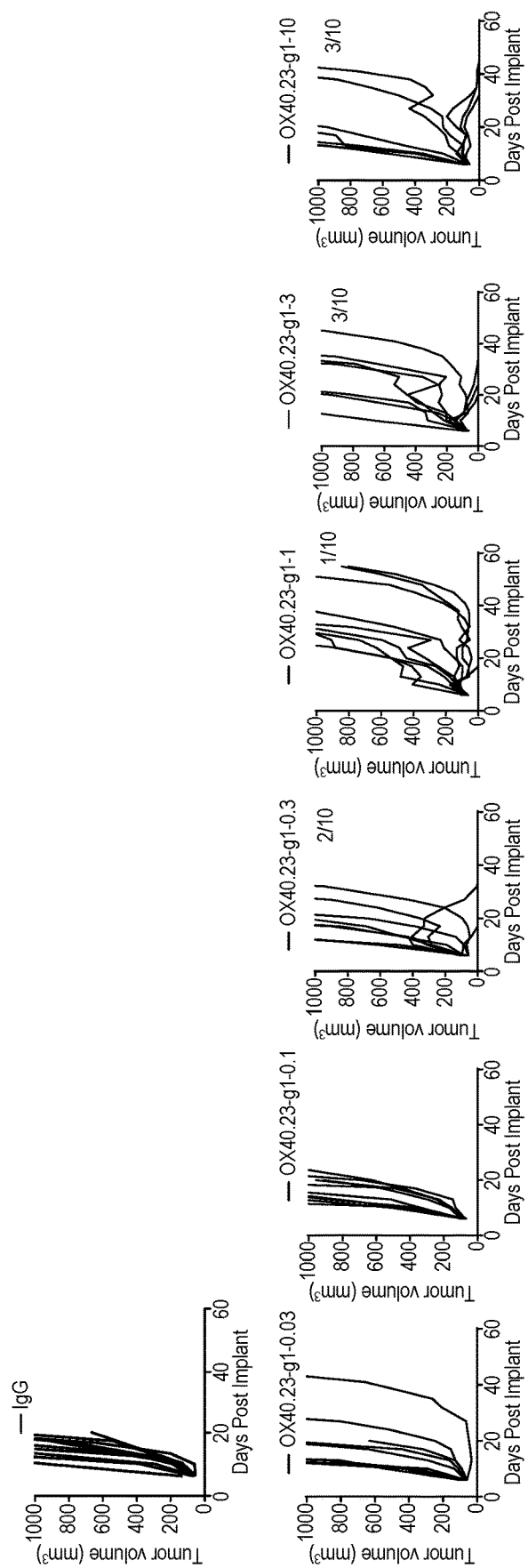
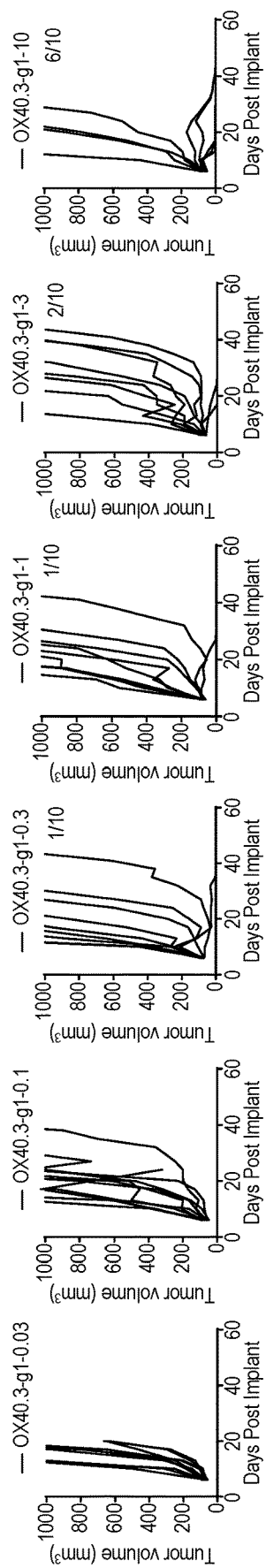
FIG. 1A
FIG. 1B

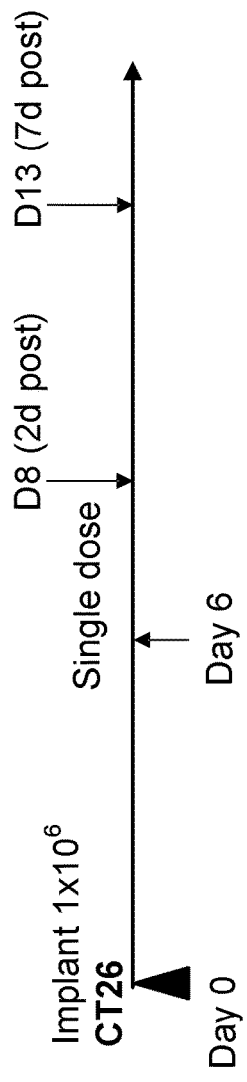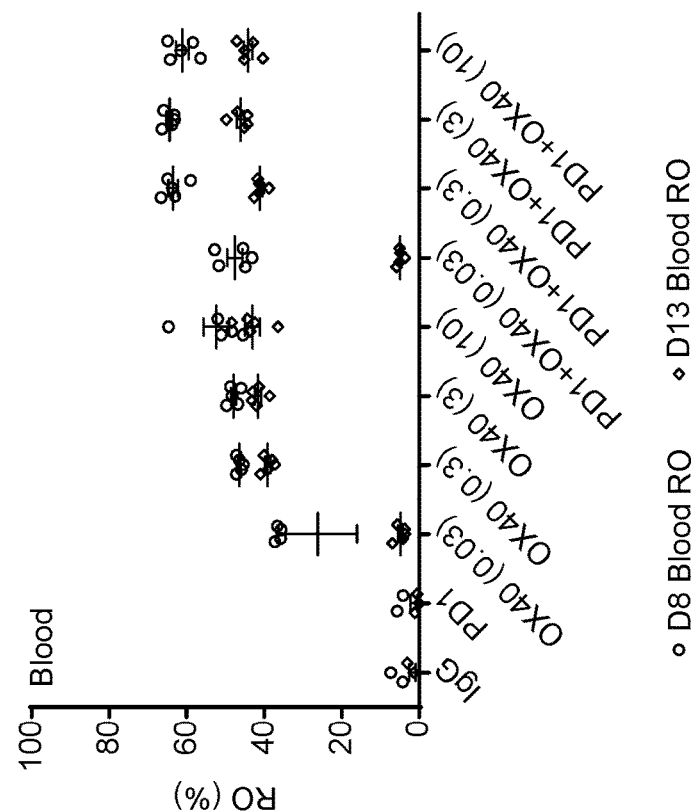
FIG. 6A
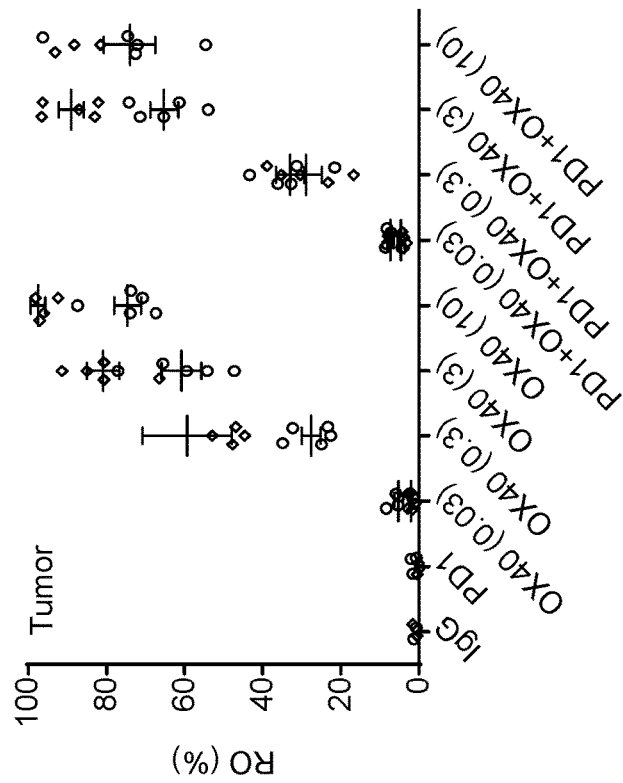
FIG. 6B

| Dose [mg] | FREQ | Predicted Median %RO in Blood | Predicted Median %RO in Tumor | Dose [mg] | FREQ | Predicted Median %RO in Blood | Predicted Median %RO in Tumor |
|---|---|---|---|---|---|---|---|
| 20 | Q2W | 89 | 87 | 40 | Q2W | 96 | 96 |
|  | Q4W | 73 | 64 |  | Q4W | 90 | 88 |
|  | Q6W | 52 | 35 |  | Q6W | 77 | 70 |
|  | Q8W | 28 | 15 |  | Q8W | 59 | 44 |
|  | Q12W | 3 | 1 |  | Q12W | 18 | 9 |
| Dose [mg] | FREQ | Predicted Median %RO in Blood | Predicted Median %RO in Tumor | Dose [mg] | FREQ | Predicted Median %RO in Blood | Predicted Median %RO in Tumor |
| 80 | Q2W | 97 | 97 | 160 | Q2W | 99 | 99 |
|  | Q4W | 95 | 95 |  | Q4W | 98 | 98 |
|  | Q6W | 90 | 89 |  | Q6W | 95 | 94 |
|  | Q8W | 83 | 78 |  | Q8W | 90 | 89 |
|  | Q12W | 53 | 36 |  | Q12W | 71 | 60 |

FIG. 10A

| Dose [mg] | FREQ | Predicted Median %RO in Blood | Predicted Median %RO in Tumor | Dose [mg] | FREQ | Predicted Median %RO in Blood | Predicted Median %RO in Tumor |
|---|---|---|---|---|---|---|---|
| 20 | Q2W | 89 | 26 | 40 | Q2W | 96 | 65 |
|  | Q4W | 73 | 9 |  | Q4W | 90 | 27 |
|  | Q6W | 52 | 3 |  | Q6W | 77 | 11 |
|  | Q8W | 28 | 1 |  | Q8W | 59 | 5 |
|  | Q12W | 3 | 0.1 |  | Q12W | 18 | 0.7 |

| Dose [mg] | FREQ | Predicted Median %RO in Blood | Predicted Median %RO in Tumor | Dose [mg] | FREQ | Predicted Median %RO in Blood | Predicted Median %RO in Tumor |
|---|---|---|---|---|---|---|---|
| 80 | Q2W | 97 | 78 | 160 | Q2W | 99 | 93 |
|  | Q4W | 95 | 54 |  | Q4W | 98 | 84 |
|  | Q6W | 90 | 29 |  | Q6W | 95 | 50 |
|  | Q8W | 83 | 15 |  | Q8W | 90 | 29 |
|  | Q12W | 53 | 4 |  | Q12W | 71 | 8 |

FIG. 10B

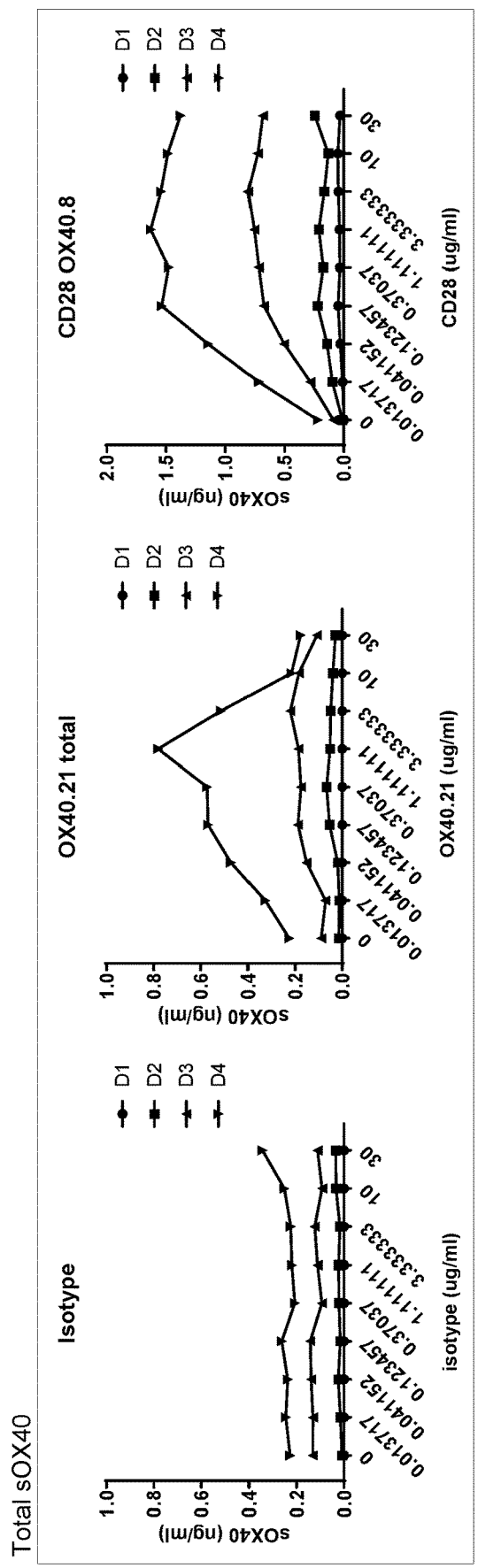
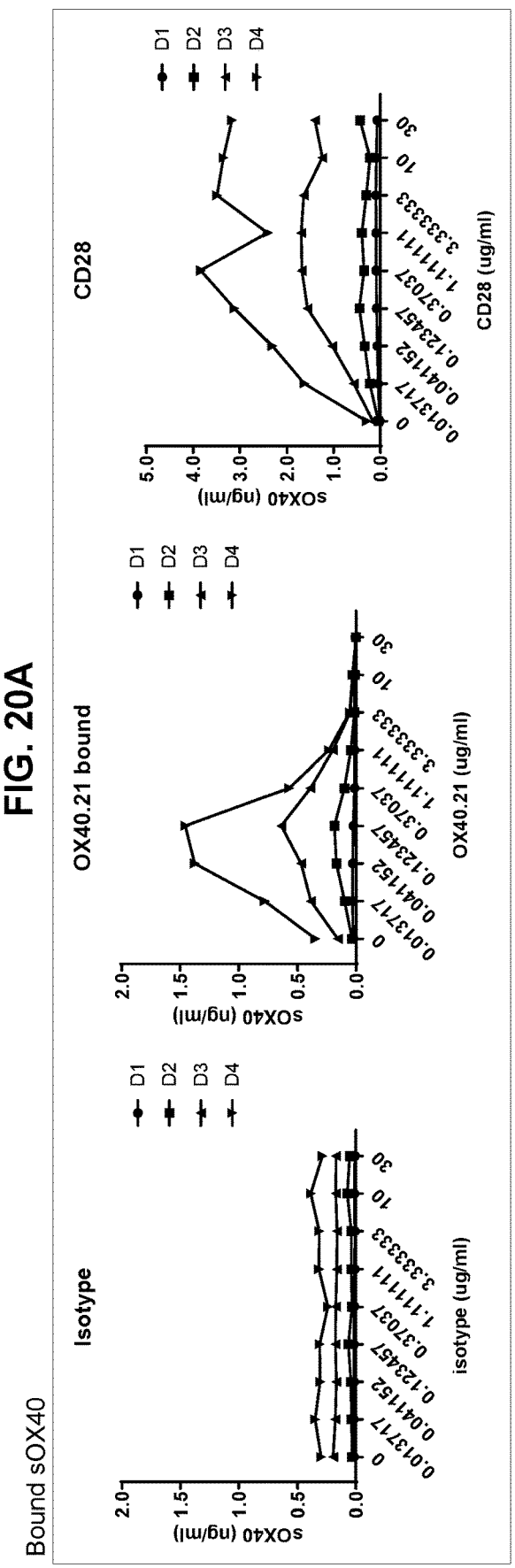
FIG. 20A
FIG. 20B pH Sensitive Internalization Assay
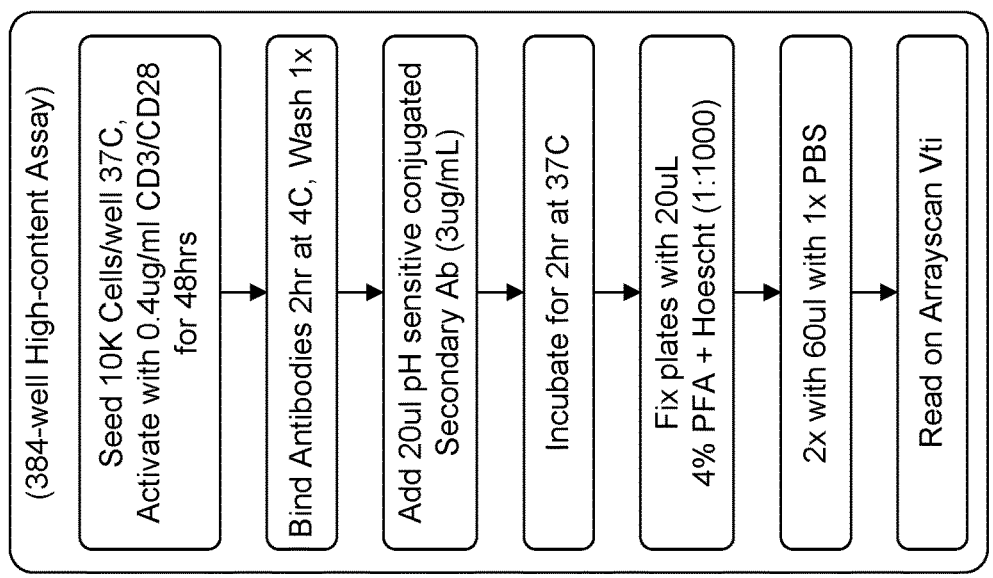
Assay scheme
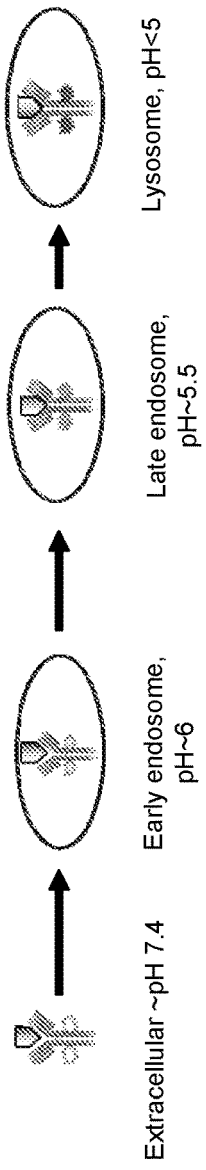
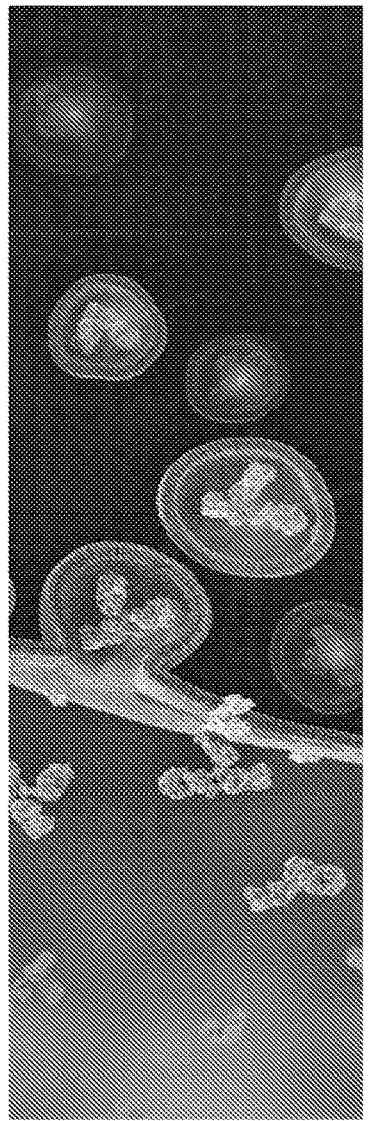
FIG. 22

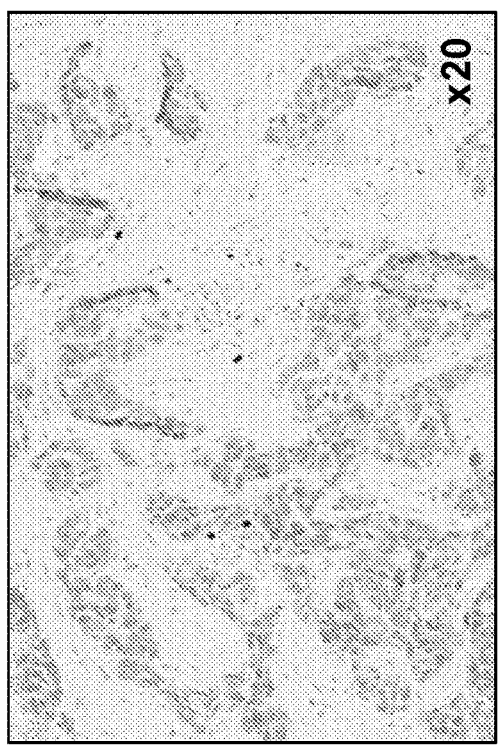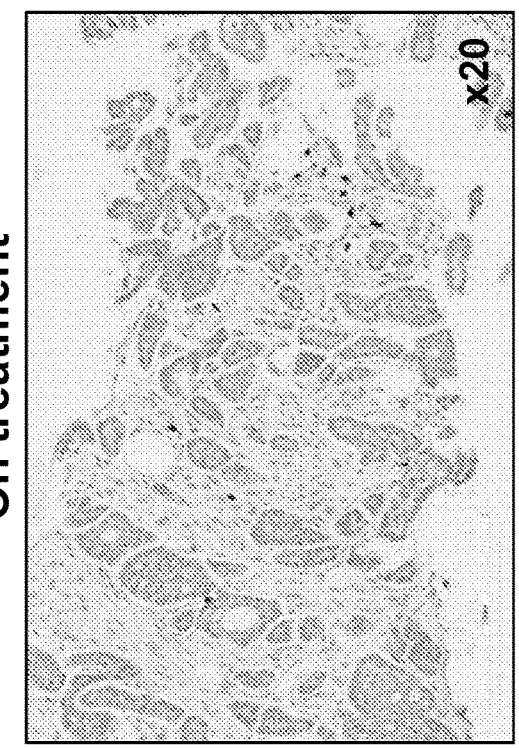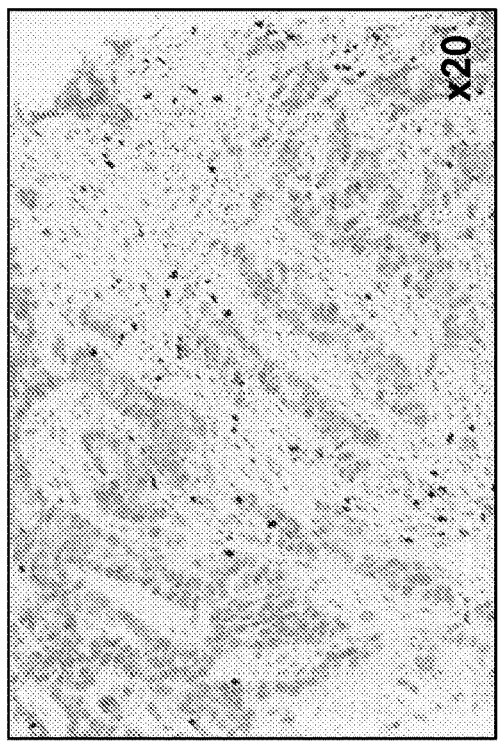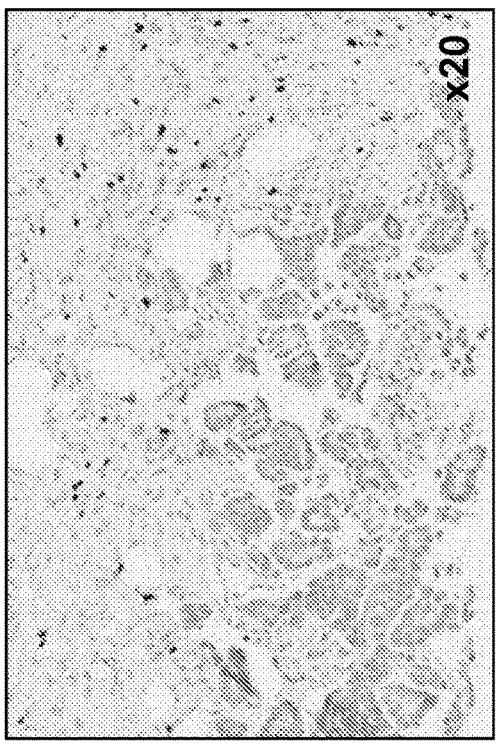
FIG. 26E

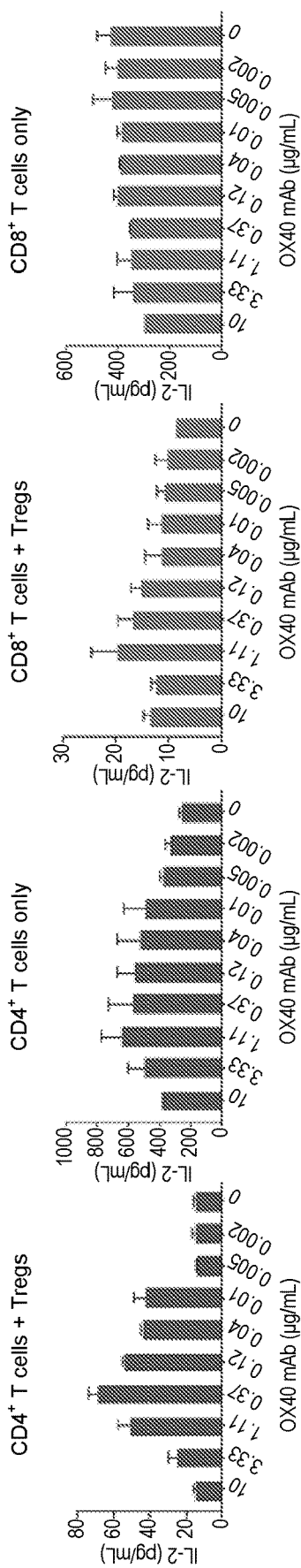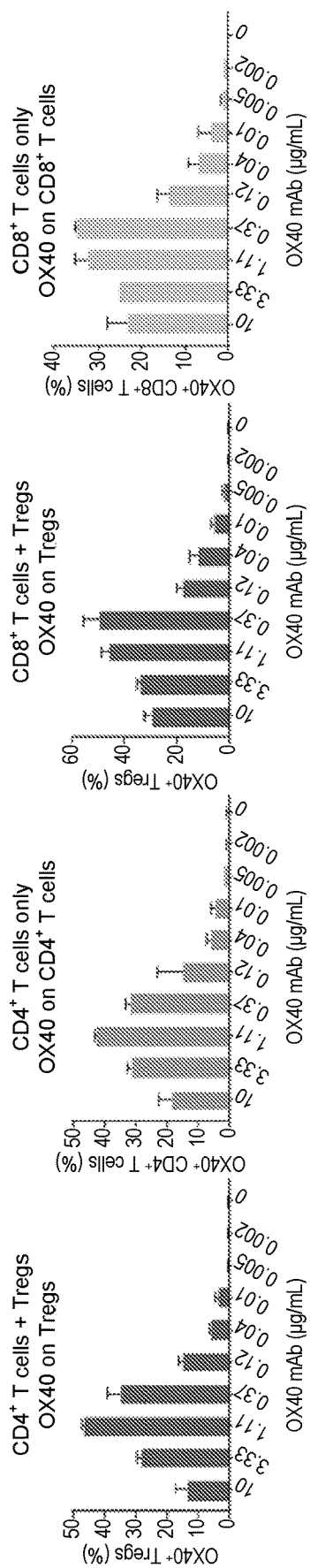

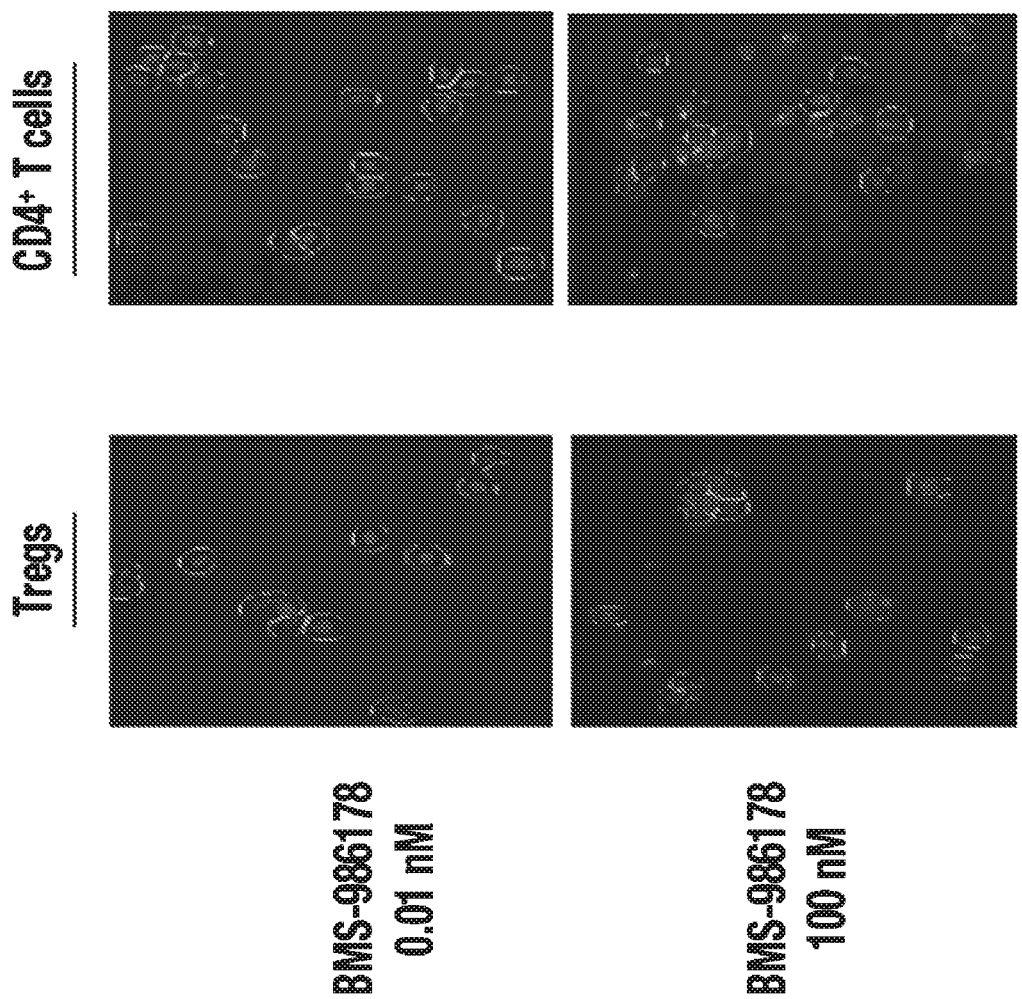

SEQUENCE LISTING

<160> NUMBER OF SEQ ID NOS: 33

<210> SEQ ID NO 1
<211> LENGTH: 277
<212> TYPE: PRT
<213> ORGANISM: Artificial Sequence
<220> FEATURE:
<223> OTHER INFORMATION: Human OX40 precursor

<400> SEQUENCE: 1

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
                180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
            210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275
```

<210> SEQ ID NO 2
<211> LENGTH: 189
<212> TYPE: PRT
<213> ORGANISM: Artificial Sequence
<220> FEATURE:
<223> OTHER INFORMATION: Extracellular domain of mature human OX40

<400> SEQUENCE: 2

```
Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
                20                  25                  30

Asn Thr Val Cys Arg Pro Cys Gly Pro Gly Phe Tyr Asn Asp Val Val
            35                  40                  45

Ser Ser Lys Pro Cys Lys Pro Cys Thr Trp Cys Asn Leu Arg Ser Gly
        50                  55                  60
```

-continued

```
Ser Glu Arg Lys Gln Leu Cys Thr Ala Thr Gln Asp Thr Val Cys Arg
 65                  70                  75                  80

Cys Arg Ala Gly Thr Gln Pro Leu Asp Ser Tyr Lys Pro Gly Val Asp
                 85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala
            180                 185
```

<210> SEQ ID NO 3
<211> LENGTH: 277
<212> TYPE: PRT
<213> ORGANISM: Artificial Sequence
<220> FEATURE:
<223> OTHER INFORMATION: Cynomolgus OX40

<400> SEQUENCE: 3

```
Met Cys Val Gly Ala Arg Arg Leu Gly Arg Gly Pro Cys Ala Ala Leu
  1               5                  10                  15

Leu Leu Leu Gly Leu Gly Leu Ser Thr Thr Ala Lys Leu His Cys Val
                 20                  25                  30

Gly Asp Thr Tyr Pro Ser Asn Asp Arg Cys Cys Gln Glu Cys Arg Pro
             35                  40                  45

Gly Asn Gly Met Val Ser Arg Cys Asn Arg Ser Gln Asn Thr Val Cys
         50                  55                  60

Arg Pro Cys Gly Pro Gly Phe Tyr Asn Asp Val Val Ser Ala Lys Pro
 65                  70                  75                  80

Cys Lys Ala Cys Thr Trp Cys Asn Leu Arg Ser Gly Ser Glu Arg Lys
                 85                  90                  95

Gln Pro Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Thr Gln Pro
                165                 170                 175

Gln Glu Thr Gln Gly Pro Pro Ala Arg Pro Thr Val Gln Pro Thr
            180                 185                 190

Glu Ala Trp Pro Arg Thr Ser Gln Arg Pro Ser Thr Arg Pro Val Glu
        195                 200                 205

Val Pro Arg Gly Pro Ala Val Ala Ala Ile Leu Gly Leu Gly Leu Ala
    210                 215                 220

Leu Gly Leu Leu Gly Pro Leu Ala Met Leu Leu Ala Leu Leu Leu Leu
225                 230                 235                 240
```

```
Arg Arg Asp Gln Arg Leu Pro Pro Asp Ala Pro Lys Ala Pro Gly Gly
                245                 250                 255

Gly Ser Phe Arg Thr Pro Ile Gln Glu Glu Gln Ala Asp Ala His Ser
            260                 265                 270

Ala Leu Ala Lys Ile
        275

<210> SEQ ID NO 4
<211> LENGTH: 183
<212> TYPE: PRT
<213> ORGANISM: Artificial Sequence
<220> FEATURE:
<223> OTHER INFORMATION: Human OX40 L

<400> SEQUENCE: 4

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Thr Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 5
<211> LENGTH: 5
<212> TYPE: PRT
<213> ORGANISM: Artificial Sequence
<220> FEATURE:
<223> OTHER INFORMATION: VHCDR1

<400> SEQUENCE: 5

Ser Tyr Ala Met Tyr
1               5

<210> SEQ ID NO 6
<211> LENGTH: 16
<212> TYPE: PRT
<213> ORGANISM: Artificial Sequence
<220> FEATURE:
<223> OTHER INFORMATION: VHCDR2
```

```
<400> SEQUENCE: 6

Ala Ile Asp Thr Asp Ala Gly Thr Phe Tyr Ala Asp Ser Val Arg Gly
1               5                   10                  15

<210> SEQ ID NO 7
<211> LENGTH: 9
<212> TYPE: PRT
<213> ORGANISM: Artificial Sequence
<220> FEATURE:
<223> OTHER INFORMATION: VHCDR3

<400> SEQUENCE: 7

Leu Gly Glu Gly Tyr Phe Phe Asp Tyr
1               5

<210> SEQ ID NO 8
<211> LENGTH: 11
<212> TYPE: PRT
<213> ORGANISM: Artificial Sequence
<220> FEATURE:
<223> OTHER INFORMATION: VLCDR1

<400> SEQUENCE: 8

Arg Ala Ser Gln Ser Val Ser Ser Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: VLCDR2

<400> SEQUENCE: 9

Asp Ala Ser Asn Arg Ala Thr
1               5

<210> SEQ ID NO 10
<211> LENGTH: 9
<212> TYPE: PRT
<213> ORGANISM: Artificial Sequence
<220> FEATURE:
<223> OTHER INFORMATION: VLCDR3

<400> SEQUENCE: 10

Gln Gln Arg Ser Asn Trp Pro Pro Thr
1               5

<210> SEQ ID NO 11
<211> LENGTH: 117
<212> TYPE: PRT
<213> ORGANISM: Artificial Sequence
<220> FEATURE:
<223> OTHER INFORMATION: VH

<400> SEQUENCE: 11

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Ala Ile Asp Thr Asp Ala Gly Thr Phe Tyr Ala Asp Ser Val Arg
    50                  55                  60
```

```
Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Phe Cys Ala
                 85                  90                  95

Arg Leu Gly Glu Gly Tyr Phe Phe Asp Tyr Trp Gly Gln Gly Thr Leu
            100                 105                 110

Val Thr Val Ser Ser
            115

<210> SEQ ID NO 12
<211> LENGTH: 107
<212> TYPE: PRT
<213> ORGANISM: Artificial Sequence
<220> FEATURE:
<223> OTHER INFORMATION: VL

<400> SEQUENCE: 12

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gly Gly Thr Lys Val Glu Ile Lys
            100                 105

<210> SEQ ID NO 13
<211> LENGTH: 446
<212> TYPE: PRT
<213> ORGANISM: Artificial Sequence
<220> FEATURE:
<223> OTHER INFORMATION: HC

<400> SEQUENCE: 13

Glu Val Gln Leu Val Gln Ser Gly Gly Gly Leu Val Gln Pro Gly Gly
  1               5                  10                  15

Ser Leu Arg Leu Ser Cys Ala Gly Ser Gly Phe Thr Phe Ser Ser Tyr
                 20                  25                  30

Ala Met Tyr Trp Val Arg Gln Ala Pro Gly Lys Gly Leu Glu Trp Val
             35                  40                  45

Ser Ala Ile Asp Thr Asp Ala Gly Thr Phe Tyr Ala Asp Ser Val Arg
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Phe Cys Ala
                 85                  90                  95

Arg Leu Gly Glu Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125
```

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 14
<211> LENGTH: 214
<212> TYPE: PRT
<213> ORGANISM: Artificial Sequence
<220> FEATURE:
<223> OTHER INFORMATION: LC

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 15
<211> LENGTH: 17
<212> TYPE: PRT
<213> ORGANISM: Artificial Sequence
<220> FEATURE:
<223> OTHER INFORMATION: synthetic

<400> SEQUENCE: 15

Asp Val Val Ser Ser Lys Pro Cys Lys Pro Cys Thr Trp Cys Asn Leu
 1               5                  10                  15

Arg

<210> SEQ ID NO 16
<211> LENGTH: 440
<212> TYPE: PRT
<213> ORGANISM: Artificial Sequence
<220> FEATURE:
<223> OTHER INFORMATION: Heavy chain  nivolumab

<400> SEQUENCE: 16

Gln Val Gln Leu Val Glu Ser Gly Gly Gly Val Val Gln Pro Gly Arg
 1               5                  10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

-continued

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 17
<211> LENGTH: 214
<212> TYPE: PRT
<213> ORGANISM: Artificial Sequence
<220> FEATURE:
<223> OTHER INFORMATION: Light chain nivolumab

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

```
Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 18
<211> LENGTH: 113
<212> TYPE: PRT
<213> ORGANISM: Artificial Sequence
<220> FEATURE:
<223> OTHER INFORMATION: Heavy chain variable region   nivolumab

<400> SEQUENCE: 18

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
                100                 105                 110

Ser

<210> SEQ ID NO 19
<211> LENGTH: 107
<212> TYPE: PRT
<213> ORGANISM: Artificial Sequence
<220> FEATURE:
<223> OTHER INFORMATION: Light chain variable region   nivolumab
```

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 20
<211> LENGTH: 5
<212> TYPE: PRT
<213> ORGANISM: Artificial Sequence
<220> FEATURE:
<223> OTHER INFORMATION: HCDR1   nivolumab

<400> SEQUENCE: 20

Asn Ser Gly Met His
1               5

<210> SEQ ID NO 21
<211> LENGTH: 17
<212> TYPE: PRT
<213> ORGANISM: Artificial Sequence
<220> FEATURE:
<223> OTHER INFORMATION: HCDR2   nivolumab

<400> SEQUENCE: 21

Val Ile Trp Tyr Asp Gly Ser Lys Arg Tyr Tyr Ala Asp Ser Val Lys
1               5                   10                  15

Gly

<210> SEQ ID NO 22
<211> LENGTH: 4
<212> TYPE: PRT
<213> ORGANISM: Artificial Sequence
<220> FEATURE:
<223> OTHER INFORMATION: HCDR3   nivolumab

<400> SEQUENCE: 22

Asn Asp Asp Tyr
1

<210> SEQ ID NO 23
<211> LENGTH: 11
<212> TYPE: PRT
<213> ORGANISM: Artificial Sequence
<220> FEATURE:
<223> OTHER INFORMATION: LCDR1   nivolumab

<400> SEQUENCE: 23

Arg Ala Ser Gln Ser Val Ser Ser Tyr Leu Ala
1               5                   10

```
<210> SEQ ID NO 24
<211> LENGTH: 7
<212> TYPE: PRT
<213> ORGANISM: Artificial Sequence
<220> FEATURE:
<223> OTHER INFORMATION: LCDR2   nivolumab

<400> SEQUENCE: 24

Asp Ala Ser Asn Arg Ala Thr
1               5

<210> SEQ ID NO 25
<211> LENGTH: 9
<212> TYPE: PRT
<213> ORGANISM: Artificial Sequence
<220> FEATURE:
<223> OTHER INFORMATION: LCDR3   nivolumab

<400> SEQUENCE: 25

Gln Gln Ser Ser Asn Trp Pro Arg Thr
1               5

<210> SEQ ID NO 26
<211> LENGTH: 118
<212> TYPE: PRT
<213> ORGANISM: Artificial Sequence
<220> FEATURE:
<223> OTHER INFORMATION: Heavy chain variable region   ipilimumab

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 27
<211> LENGTH: 108
<212> TYPE: PRT
<213> ORGANISM: Artificial Sequence
<220> FEATURE:
<223> OTHER INFORMATION: Light chain variable region

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
                100                 105
```

<210> SEQ ID NO 28
<211> LENGTH: 5
<212> TYPE: PRT
<213> ORGANISM: Artificial Sequence
<220> FEATURE:
<223> OTHER INFORMATION: HCDR1    ipilimumab

<400> SEQUENCE: 28

```
Ser Tyr Thr Met His
1               5
```

<210> SEQ ID NO 29
<211> LENGTH: 17
<212> TYPE: PRT
<213> ORGANISM: Artificial Sequence
<220> FEATURE:
<223> OTHER INFORMATION: HCDR2    ipilimumab

<400> SEQUENCE: 29

```
Phe Ile Ser Tyr Asp Gly Asn Asn Lys Tyr Tyr Ala Asp Ser Val Lys
1               5                   10                  15

Gly
```

<210> SEQ ID NO 30
<211> LENGTH: 9
<212> TYPE: PRT
<213> ORGANISM: Artificial Sequence
<220> FEATURE:
<223> OTHER INFORMATION: HCDR3    ipilimumab

<400> SEQUENCE: 30

```
Thr Gly Trp Leu Gly Pro Phe Asp Tyr
1               5
```

<210> SEQ ID NO 31
<211> LENGTH: 12
<212> TYPE: PRT
<213> ORGANISM: Artificial Sequence
<220> FEATURE:
<223> OTHER INFORMATION: LCDR1    ipilimumab

<400> SEQUENCE: 31

```
Arg Ala Ser Gln Ser Val Gly Ser Ser Tyr Leu Ala
1               5                   10
```

<210> SEQ ID NO 32
<211> LENGTH: 7
<212> TYPE: PRT
<213> ORGANISM: Artificial Sequence
<220> FEATURE:
<223> OTHER INFORMATION: LCDR2    ipilimumab

<400> SEQUENCE: 32

```
Gly Ala Phe Ser Arg Ala Thr
1               5
```

```
<210> SEQ ID NO 33
<211> LENGTH: 9
<212> TYPE: PRT
<213> ORGANISM: Artificial Sequence
<220> FEATURE:
<223> OTHER INFORMATION: LCDR3  ipilimumab

<400> SEQUENCE: 33

Gln Gln Tyr Gly Ser Ser Pro Trp Thr
1               5
```

IMMUNOSTIMULATORY AGONISTIC ANTIBODIES FOR USE IN TREATING CANCER

CROSS-REFERENCE TO RELATED APPLICATIONS

This PCT application claims the priority benefit of U.S. Provisional Application Nos. 62/580,346, filed Nov. 1, 2017; 62/581,441, filed Nov. 3, 2017; 62/581,905, filed Nov. 6, 2017; 62/583,808, filed Nov. 9, 2017; 62/628,207, filed Feb. 8, 2018; and 62/657,616, filed Apr. 13, 2018, each of which is herein incorporated by reference in its entirety

REFERENCE TO SEQUENCE LISTING SUBMITTED ELECTRONICALLY

The content of the electronically submitted sequence listing in ASCII text file (Name: 3338.115PC06_ST25.txt; Size: 30,589 bytes; and Date of Creation: Oct. 30, 2018) filed with the application is herein incorporated by reference in its entirety.

BACKGROUND

Although a number of immunoinhibitory receptors have been successfully targeted in cancer therapies, the complex interplay between stimulatory and inhibitory receptors expressed on immune cells, such as regulatory T cells, effector cells (e.g., T cells), and antigen-presenting cells, renders difficult the prediction of whether an antibody targeting a particular immune receptor would be effective. Relative to the recent success of antagonistic antibodies that target immunoinhibitory receptors (e.g., nivolumab, ipilimumab), few agonistic antibodies that target immunostimulatory receptors have been successful in clinical settings due to, e.g., lack of efficacy and/or toxicity. These antibodies represent untapped potential, and have the possibility to substantially increase the pool of therapeutics available to combat oncologic indications if the reasons underlying their lack of efficacy/toxicity can be addressed and their use optimized. Given the ongoing need for improved strategies for treating diseases such as cancer through, e.g., enhancing immune responses such as T cell responses, optimizing methods for activating immunostimulatory receptors would be therapeutically beneficial.

SUMMARY

In one aspect, provided herein is a method of treating cancer comprising administering to a subject in need thereof an agonistic antibody that specifically binds to an immunostimulatory receptor, wherein the antibody is administered in an amount or frequency sufficient to achieve and/or maintain a receptor occupancy of less than about 80%.

In another aspect, provided herein is method of reducing or depleting the number of T regulatory cells in a tumor of a subject with cancer comprising administering to the subject an agonistic antibody that specifically binds to an immunostimulatory receptor, wherein the antibody is administered in an amount or frequency sufficient to achieve and/or maintain a receptor occupancy of less than about 80%.

In another aspect, provided herein is a method of increasing IL-2 and/or IFN-γ production in T cells in a subject with cancer comprising administering to the subject an agonistic antibody that specifically binds to an immunostimulatory receptor, wherein the antibody is administered in an amount or frequency sufficient to achieve and/or maintain a receptor occupancy of less than about 80%.

In another aspect, provided herein is a method of stimulating an immune response in a subject with cancer comprising administering to the subject an agonistic antibody that specifically binds to an immunostimulatory receptor, wherein the antibody is administered in an amount or frequency sufficient to achieve and/or maintain a receptor occupancy of less than about 80%.

In another aspect, provided herein is a method of inhibiting the growth of tumor cells in a subject with cancer comprising administering to the subject an agonistic antibody that specifically binds to an immunostimulatory receptor, wherein the antibody is administered in an amount or frequency sufficient to achieve and/or maintain a receptor occupancy of less than about 80%.

In another aspect, provided herein is a method of selecting an effective dose or schedule of antibody administration of a therapeutic agonistic antibody that specifically binds to an immunostimulatory receptor for the treatment of a subject with cancer comprising:
  (a) administering the agonistic antibody to an animal model;
  (b) obtaining a sample from the animal model;
  (c) determining receptor occupancy or receptor occupancy range of the agonistic antibody in the sample;
  (d) using the receptor occupancy or receptor occupancy range obtained from step (c) to project an expected receptor occupancy or receptor occupancy range in the subject; and
  (e) selecting a dose or schedule of antibody administration of the agonistic antibody that is sufficient to achieve and/or maintain a receptor occupancy of less than about 80% in the subject based on the expected receptor occupancy obtained in step (d).

In another aspect provided herein is a method of treating cancer in a subject comprising administering to the subject an effective amount of a therapeutic agonistic antibody that specifically binds to an immunostimulatory receptor, or a pharmaceutical composition comprising the antibody, wherein the effective amount of the antibody to administer has been selected according to the methods described herein.

In another aspect, provided herein is a method of monitoring the level of a therapeutic agonistic antibody that specifically binds to an immunostimulatory receptor in a subject being treated for cancer, comprising:
  (a) obtaining a sample from the subject;
  (b) determining receptor occupancy of the agonistic antibody in the sample;
  (c) reducing the amount or frequency of the agnostic antibody being administered to the subject if the receptor occupancy is greater than about 80% (e.g., 70%, 60%, 50%), or increasing the amount or frequency of the antibody if the receptor occupancy is less than about 20% (e.g., 30%, 40%, 50%, or 60%);
  (d) optionally repeating steps (a)-(c) until a receptor occupancy of about 20% to about 80% (e.g., about 20% to about 70%, about 20% to about 60%, about 20% to about 50%, about 20% to about 40%) is achieved and/or maintained.

In another aspect, provided herein is a method of treating cancer comprising administering to a subject in need thereof an agonistic antibody that specifically binds to an immunostimulatory receptor and an additional therapy, wherein the additional therapy is administered on a fixed frequency and the agonistic antibody is administered at a dose and frequency that is sufficient to achieve and/or maintain a receptor occupancy of less than about 80%.

In another aspect, provided herein is a method of determining the effectiveness of a treatment for cancer in a subject administered a therapeutic agonistic antibody that specifically binds to an immunostimulatory receptor comprising measuring levels of soluble OX40 in the subject (e.g., in a sample from the subject).

In some embodiments of the methods disclosed herein, the agonistic antibody is administered in a dose or frequency sufficient to achieve and/or maintain a receptor occupancy range of about 20% to about 80%, about 20% to about 70%, about 20% to about 60%, about 20% to about 50%, about 20% to about 40%. In some embodiments, receptor occupancy and/or receptor occupancy range is measured on day 1 after cycle 1 of a treatment regimen.

In certain embodiments of the methods disclosed herein, the agnostic antibody that binds to an immunostimulatory receptor, such as a co-stimulatory receptor. In some embodiments, the antibody binds to a member of the tumor necrosis factor receptor superfamily, ICOS, LFA-1 (CD11a/CD18), CD2, CD7, CD30, CD40, CD54, CD160, BAFFR, HVEM, LIGHT, NKG2C, SLAMF7, and NKp80. In one embodiment, the agonistic antibody binds to OX40.

In some embodiments of the methods disclosed herein, the agonistic antibody is selected from the group consisting of IgG1, IgG2, IgG3, IgG4, or a variant thereof. In some embodiments, the agonistic antibody comprises an Fc having enhanced binding to an activating FcγR. In some embodiments, the agonistic antibody is a human, humanized, or chimeric antibody. In some embodiments, the agonistic antibody is a bispecific antibody.

In some embodiments of the methods disclosed herein, the cancer to be treated is selected from the group consisting of: bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, non-small cell lung cancer, and virus-related cancer. In some embodiments, the cancer is metastatic, refractory, or recurrent.

In some embodiments of the methods described herein, one or more additional therapies (e.g., anti-PD1 antibody, anti-PDL1 antibody, anti-LAG3 antibody, anti-CTLA4 antibody, anti-TGFβ antibody) is further administered to a subject (e.g., a human patient). Such one or more additional therapies can be administered before, after, or concurrently with the agonistic antibody.

In some embodiments, the agonistic antibody and, optionally, one or more additional therapies is formulated as a pharmaceutical composition.

BRIEF DESCRIPTION OF THE DRAWINGS

FIGS. 1A and 1B are tumor growth curves of a CT26 mouse tumor model treated with the indicated dose (in mg/kg) of IgG and ligand-blocking OX40.23 (FIG. 1A) and ligand non-blocking OX40.3 (FIG. 1B).

FIG. 6A is a schematic for dosing and sampling schedule for OX40.23 administered as monotherapy or combination therapy with anti-PD1 antibody. FIG. 6B shows graphs of OX40 receptor occupancy (RO) in mice treated with IgG, PD1, OX40.23 (0.3, 3, and 10 mg/kg), and anti-PD1 antibody+OX40.23 (at 0.03, 0.3, 3, and 10 mg/kg) in blood and tumor samples.

FIGS. 10A and 10B show the predicted human tumor RO for various dosing regimens. FIG. 10A provides the mean tumor penetration and mean target load. FIG. 10B provides the low tumor penetration and high target load.

FIG. 20A is a graph showing total levels of sOX40 on days 1, 2, 3, and 4 when cells were treated with isotype, OX40.21, or an anti-CD28 antibody. FIG. 20B is a graph showing levels of bound sOX40 on days 1, 2, 3, and 4, when cells were treated with isotype, OX40.21, or an anti-CD28 antibody.

FIG. 22 is a schematic showing the OX40 internalization assay.

FIG. 26E shows an immunohistochemical analysis of FOXP3+ cells from tumor samples of human patients with ovarian serous carcinoma (upper panel) and ovarian adenocarcinoma (lower panel).

FIGS. 33A-33I show the hook effect and dose dependency in a Treg suppression assay when CHO cells were treated with OX-40 agonist antibody. FIG. 33A is a schematic of the Treg suppression assay. FIG. 33B shows IL-2 expression over treatment of various concentrations of BMS-986178 (BMS-986178 surrogate mouse antibody) in CD4+ in the presence of Tregs. FIG. 33C shows IL-2 expression over treatment of various concentrations of BMS-986178 (BMS-986178 surrogate mouse antibody) in CD4+ in the absence of Tregs. FIG. 33D shows OX40 expression on Tregs from the corresponding cultures over treatment of various concentrations of BMS-986178 (BMS-986178 surrogate mouse antibody) in CD4+ in the presence of Tregs. FIG. 33E shows OX40 expression on Tregs from the corresponding cultures over treatment of various concentrations of BMS-986178 (BMS-986178 surrogate mouse antibody) in CD4+ in the absence of Tregs. FIG. 33F shows IL-2 expression over treatment of various concentrations of BMS-986178 (BMS-986178 surrogate mouse antibody) in CD8+ in the presence of Tregs. FIG. 33G shows IL-2 expression over treatment of various concentrations of BMS-986178 (BMS-986178 surrogate mouse antibody) in CD8+ in the absence of Tregs. FIG. 33H shows OX40 expression on Tregs from the corresponding cultures over treatment of various concentrations of BMS-986178 (BMS-986178 surrogate mouse antibody) in CD8+ in the presence of Tregs. FIG. 33I shows OX40 expression on Tregs from the corresponding cultures over treatment of various concentrations of BMS-986178 (BMS-986178 surrogate mouse antibody) in CD8+ in the absence of Tregs.

(BMS-986178 surrogate mouse antibody), 5 mg/kg BMS-986178 (BMS-986178 surrogate mouse antibody), or control PD-1 monoclonal antibody.

FIG. 36 shows internalization of OX40-bound-BMS-986178 (BMS-986178 surrogate mouse antibody) internalized in Tregs and CD4+ T cells when cells were treated with 0.01 nM and 100 nM of BMS-986178.

FIG. 46A shows the calibration curve between BMS-986178 and two different OX40 proteins (OX40-His_Sino and OX40-Fc_R&D). FIG. 46B shows the serum OX40 correlation between two antibody pairs. FIGS. 46C and 46D show the dilution parallelism and linearity, respectively. FIG. 46E shows the selectivity of BMS-986178. FIGS. 46F and 46G shows the drug interference data. FIG. 46H shows the storage and freeze-thaw stability of BMS-986178 at 5 different conditions.

DETAILED DESCRIPTION

Figure 2A:
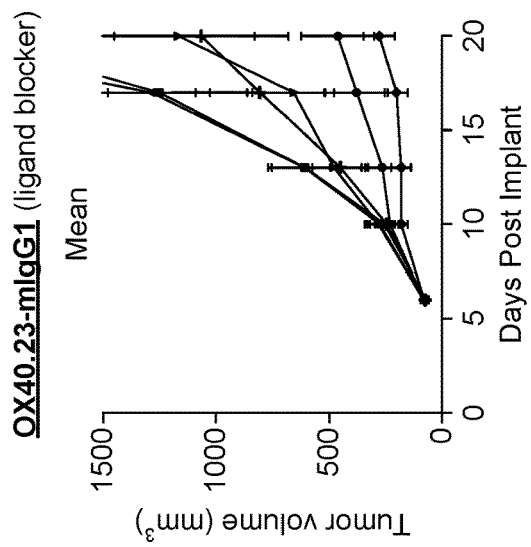
FIGS. 2A and 2B show the mean and median tumor volumes of the OX40.3 treated mice at the indicated doses (mg/kg), respectively.
Figure 2B:
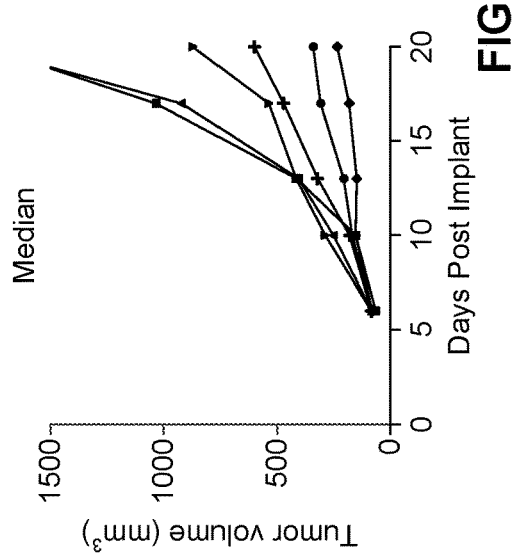
Figure 2C:
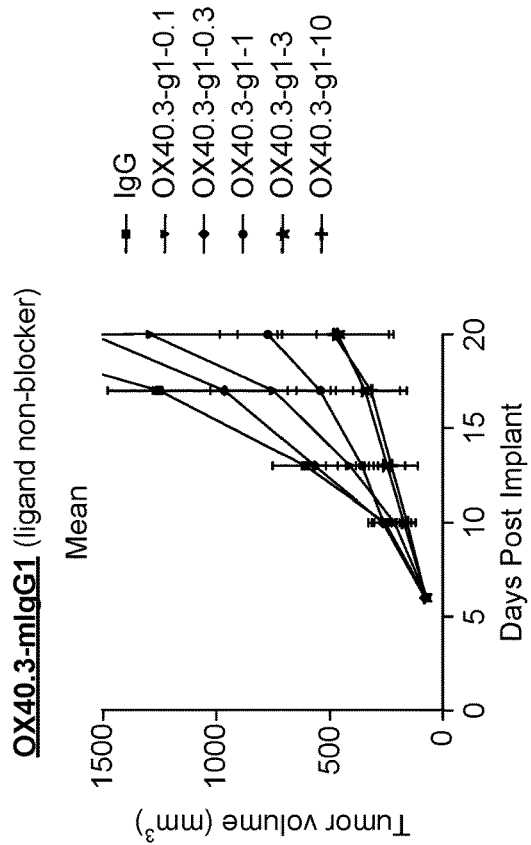
FIGS. 2C and 2D show the mean and median tumor volumes of the OX40.23 treated mice at the indicated doses (mg/kg), respectively.
Figure 2D:
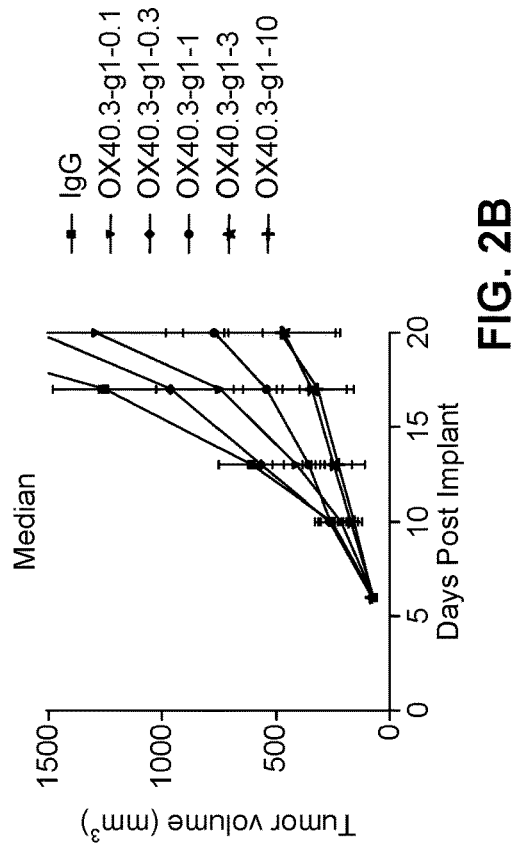

Provided herein are methods of enhancing an immune response using agonistic antibodies that specifically bind to immunostimulatory receptors in amount sufficient to achieve and/or maintain a receptor occupancy of less than about 80%, wherein the antibodies are administered alone or in combination with other immunostimulatory agents and/or cancer therapies. The methods described herein may be used in a wide variety of oncological applications, e.g., to treat cancer or inhibit tumor growth.

Definitions

In order that the present description may be more readily understood, certain terms are first defined. Additional definitions are set forth throughout the detailed description.

As used herein, "immunostimulatory receptor" refers to a receptor that is involved in stimulating an immune response. Such receptors include, for example, co-stimulatory receptors.

As used herein, "co-stimulatory receptor" refers to a receptor that transmits a co-stimulatory signal to an immune cell. Examples of co-stimulatory receptors include, but are not limited to, members of the tumor necrosis factor receptor superfamily (TNFRSF), ICOS (CD278), CD28, LIGHT, CD40L, TIM1, SLAM, CD1, CD2, CD226, LFA-1 (CD11A, CD18), CD2, CD5, CD7, CD30, CD54, CD97, CD154, CD160, LIGHT, NKG2C, SLAMF7, and NKp80.

As used herein, an "agonist antibody" or "agonistic antibody" refers to an antibody that is an agonist of an immunostimulatory receptor, e.g., an antibody that is capable of boosting the immune system (or an immune response) of a subject by stimulating the activity of a protein that, in turn, stimulates an immune cell.

As used herein, an "agonistic antibody that binds to an immunostimulatory receptor" or synonymous expressions refers to an antibody that specifically binds to an immunostimulatory receptor (e.g., a co-stimulatory receptor such as a member of the tumor necrosis factor receptor superfamily), and activates the receptor and/or its downstream signaling pathway(s).

As used herein, "tumor necrosis factor receptor superfamily" or "TNFRSF" refers to a protein superfamily of cytokine receptors having cysteine-rich domains in their extracellular domains that bind to cognate ligands, and includes members such as TNFR1, TNFR2, HVEM, LTβR, OX40, CD27, CD40, FAS, DCR3, CD30, 4-1BB, TRAILR1, TRAILR2, TRAILR3, TRAILR4, OPG, RANK, FN14, TACI, BAFFR, BCMA, GITR, TROY, DR3 (death receptor 3), DR6 (death receptor 6), XEDAR (ectodysplasin A2 receptor), and NGFR (see, e.g., Croft et al., *Nat Rev Drug Discov* 2013; 12:147-168).

The term "OX40" as used herein refers to a receptor that is a member of the TNFRSF, which binds to OX40 ligand (OX40-L). OX40 is also referred to as tumor necrosis factor receptor superfamily, member 4 (TNFRSF4), ACT35, IMD16, TXGP1L, and CD134. The term "OX40" includes any variants or isoforms of OX40 which are naturally expressed by cells.

The amino acid sequence of human OX40 precursor (Accession No. NP_003318.1) is set forth in SEQ ID NO: 1. The amino acid sequence of the extracellular domain of mature human OX40 is set forth in SEQ ID NO: 2. The amino acid sequence of cynomolgus OX40 is set forth in SEQ ID NO: 3. The amino acid sequence of human OX40-L is set forth in SEQ ID NO: 4.

The terms "Programmed Death 1," "Programmed Cell Death 1," "Protein PD-1," "PD-1," PD1," "PDCD1," "hPD-1" and "hPD-I," refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

The term "cytotoxic T lymphocyte-associated antigen-4," "CTLA-4," "CTLA4," "CTLA-4 antigen" and "CD152" (see, e.g., Murata (1999) Am. J. Pathol. 155:453-460) are used interchangeably, and include variants, isoforms, species homologs of human CTLA-4, and analogs having at least one common epitope with CTLA-4 (see, e.g., Balzano (1992) Int. J. Cancer Suppl. 7:28-32). A complete sequence of human CTLA-4 is set forth in GenBank Accession No. L1 5006.

The term "antibody" as used to herein may include whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region. In certain naturally occurring IgG, IgD, and IgA antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antibodies typically bind specifically to their cognate antigen with high affinity, reflected by a dissociation constant ($K_D$) of $10^{-7}$ to $10^{-11}$M or less. Any $K_D$ greater than about $10^{-6}$M is generally considered to indicate nonspecific binding. As used herein, an antibody that "binds specifically" to an antigen refers to an antibody that binds to the antigen and substantially identical antigens with high affinity, which means having a $K_D$ of $10^{-7}$M or less, preferably $10^{-8}$M or less, even more preferably $5 \times 10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen. By way of example, an antibody that binds specifically to human OX40 may cross-react with OX40 from certain non-human primate species (e.g., cynomolgus monkey), but may not cross-react with OX40 from other species (e.g., murine OX40), or with an antigen other than OX40.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In certain embodiments, the anti-OX40 antibodies described herein are of the IgG1 or IgG2 subtype. Immunoglobulins, e.g., IgG1, exist in several allotypes, which differ from each other in at most a few amino acids. "Antibody" may include, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

The term "antigen-binding portion" or "antigen-binding fragment" of an antibody, as used herein, refers to one or more fragments of an antibody that retain the ability to specifically bind to an antigen (e.g., human OX40). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These and other potential constructs are described at Chan & Carter (2010) *Nat. Rev. Immunol.* 10:301. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animals (e.g., a transgenic mouse having a genome comprising a human heavy chain transgene and a light chain), to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations that occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid sequences that encode the light chain and heavy chain immunoglobulin polypeptides in response to an antigen may not be identical to the original germline sequences, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most, or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

The phrases "an antibody recognizing an antigen" and "an antibody specific for an antigen" are used interchangeably herein with the term "an antibody which binds specifically to an antigen."

An "isolated antibody," as used herein, is intended to refer to an antibody that is substantially free of other antibodies having different antigenic specificities.

As used herein, an antibody that "inhibits binding of OX40-L to OX40" is intended to refer to an antibody that inhibits the binding of OX40-L to OX40.

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Various properties of human FcγRs are summarized in Table 1. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

TABLE 1

Properties of human FcγRs

| Fcγ | Allelic variants | Affinity for human IgG | Isotype preference | Cellular distribution |
| --- | --- | --- | --- | --- |
| FcγRI | None described | High ($K_D$ ~10 nM) | IgG1 = 3 > 4 >> 2 | Monocytes, macrophages, activated neutrophils, dendritic cells |
| FcγRIIA | H131 | Low to medium | IgG1 > 3 > 2 > 4 | Neutrophils, monocytes, macrophages, eosinophils, |
| | R131 | Low | IgG1 > 3 > 4 > 2 | dendritic cells, platelets |
| FcγRIIIA | V158 | Medium | IgG1 = 3 >> 4 > 2 | NK cells, monocytes, |
| | F158 | Low | IgG1 = 3 >> 4 > 2 | macrophages, mast cells, eosinophils, dendritic cells |
| FcγRIIB | I232 | Low | IgG1 = 3 = 4 > 2 | B cells, monocytes, |
| | T232 | Low | IgG1 = 3 = 4 > 2 | macrophages, dendritic cells, mast cells |

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises $C_{H2}$ and $C_{H3}$ constant domains in each of the antibody's two heavy chains; IgM and IgE Fc regions comprise three heavy chain constant domains ($C_H$ domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. Kabat et al. (1991) *Sequences of Proteins of Immunological Interest*, National Institutes of Health, Bethesda, Md.; see also FIGS. 3C-3F of U.S. Pat. App. Pub. No. 2008/0248028. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG. As used herein, the Fc region may be a native sequence Fc, including any allotypic variant, or a variant Fc (e.g., a non-naturally occurring Fc). Fc may also refer to this region in isolation or in the context of an Fc-comprising protein polypeptide such as a "binding protein comprising an Fc region," also referred to as an "Fc fusion protein" (e.g., an antibody or immunoadhesin).

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE 2000 surface plasmon resonance (SPR) instrument using the predetermined antigen as the analyte and the antibody as the ligand, and (ii) binds to the predetermined antigen with an affinity that is at least two-fold greater than its affinity for binding to a non-specific antigen (e.g., BSA, casein) other than the predetermined antigen or a closely-related antigen.

The term "$k_{assoc}$" or "$k_a$", as used herein, is intended to refer to the association rate constant of a particular antibody-antigen interaction, whereas the term "kdis" or "$k_d$," as used herein, is intended to refer to the dissociation rate constant of a particular antibody-antigen interaction. The term "$K_D$", as used herein, is intended to refer to the equilibrium dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® SPR system or flow cytometry and Scatchard analysis.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

The term "EC50" in the context of an in vitro or in vivo assay using an antibody refers to the concentration of antibody that induces a response that is 50% of the maximal response, i.e., halfway between the maximal response and the baseline.

"Receptor occupancy" or "occupancy of the receptor," as used herein, refers to the amount of agonistic antibody that is bound to the immunostimulatory receptor. "% receptor occupancy" or "% occupancy of the receptor" can be calculated using the following formula: ([ΔMFI of Test]/[ΔMFI of Total])×100. ΔMFI is calculated by subtracting the mean fluorescence intensity (MFI) of background staining with an isotype control antibody from the MFI from the bound agonistic antibody. The total receptor level is determined by adding a saturating amount of agonistic antibody in order to determine the maximum expression and therefore MFI of the particular immunostimulatory receptor. An alternative means to calculate total receptor expression is to use an antibody against the same immunostimulatory receptor that does not compete with the agonistic antibody for which receptor occupancy is being calculated.

An "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4+ or CD8+ T cell, or the inhibition of a Treg cell.

"Immunotherapy" refers to the treatment of a subject afflicted with, or at risk of contracting or suffering a recurrence of, a disease by a method comprising inducing, enhancing, suppressing or otherwise modifying an immune response.

"T effector" ("$T_{eff}$") cells refers to T cells (e.g., CD4+ and CD8+ T cells) with cytolytic activities as well as T helper (Th) cells, which secrete cytokines and activate and direct other immune cells, but does not include regulatory T cells (Treg cells).

An increased ability to stimulate an immune response or the immune system can result from an enhanced agonist activity of T cell costimulatory receptors and/or an enhanced antagonist activity of inhibitory receptors. An increased ability to stimulate an immune response or the immune system may be reflected by a fold increase of the $EC_{50}$ or maximal level of activity in an assay that measures an immune response, e.g., an assay that measures changes in cytokine or chemokine release, cytolytic activity (determined directly on target cells or indirectly via detecting CD107a or granzymes) and proliferation. The ability to stimulate an immune response or the immune system activity may be enhanced by at least 10%, 30%, 50%, 75%, 2 fold, 3 fold, 5 fold or more.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, sub- cuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the term "T cell-mediated response" refers to a response mediated by T cells, including effector T cells (e.g., CD8+ cells) and helper T cells (e.g., CD4+ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by CD8+ T cells.

As used herein, the terms "inhibits" or "blocks" (e.g., inhibition/blocking of binding of OX40-L to OX40 on cells) are used interchangeably and encompass both partial and complete inhibition/blocking. Similarly, a "blocking antibody" refers to an antibody which blocks the binding of a ligand to its receptor, e.g., OX40.21 inhibits the binding of OX40 to its ligand, and thus is referred to as a blocking antibody. Conversely, an antibody which does not block the binding of a ligand to its receptor, e.g., OX40.8, is referred to as a "non-blocking antibody."

As used herein, the term "inhibits growth" of a tumor includes any measurable decrease in the growth of a tumor, e.g., the inhibition of growth of a tumor by at least about 10%, for example, at least about 20%, at least about 30%, at least about 40%, at least about 50%, at least about 60%, at least about 70%, at least about 80%, at least about 90%, at least about 99%, or 100%.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Prophylaxis refers to administration to a subject who does not have a disease, to prevent the disease from occurring or minimize its effects if it does.

A "hematological malignancy" includes a lymphoma, leukemia, myeloma or a lymphoid malignancy, as well as a cancer of the spleen and the lymph nodes. Exemplary lymphomas include both B cell lymphomas (a B-cell hematological cancer) and T cell lymphomas. B-cell lymphomas include both Hodgkin's lymphomas and most non-Hodgkin's lymphomas. Non-limiting examples of B cell lymphomas include diffuse large B-cell lymphoma, follicular lymphoma, mucosa-associated lymphatic tissue lymphoma, small cell lymphocytic lymphoma (overlaps with chronic lymphocytic leukemia), mantle cell lymphoma (MCL), Burkitt's lymphoma, mediastinal large B cell lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia, acute myelogenous leukemia, chronic myelogenous leukemia, and acute lymphoblastic leukemia. Hematological malignancies further include myelomas, such as, but not limited to, multiple myeloma and smoldering multiple myeloma. Other hematological and/or B cell- or T-cell-associated cancers are encompassed by the term hematological malignancy.

The term "effective dose" or "effective dosage" or "sufficient dose" is defined as an amount of drug (e.g., an agonistic antibody that binds to an immunostimulatory receptor) sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction.

In reference to solid tumors, an effective amount comprises an amount sufficient to cause a tumor to shrink and/or to decrease the growth rate of the tumor (such as to suppress tumor growth) or to prevent or delay other unwanted cell proliferation. In certain embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit, i.e., slow to some extent and may stop, tumor metastasis; (v) inhibit tumor growth; (vi) prevent or delay occurrence and/or recurrence of tumor; and/or (vii) relieve to some extent one or more of the symptoms associated with the cancer.

As used herein, the terms "fixed dose", "flat dose" and "flat-fixed dose" are used interchangeably and refer to a dose that is administered to a patient without regard for the weight or body surface area (BSA) of the patient. The fixed or flat dose is therefore not provided as a mg/kg dose, but rather as an absolute amount of the agent.

A "prophylactically effective amount" or a "prophylactically effective dosage" of a drug, is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that slows cancer progression or promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. Pharmacological effectiveness refers to the ability of the drug to promote cancer regression in the patient. Physiological safety refers to an acceptably low level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In other preferred embodiments described herein, tumor regression may be observed and may continue for a period of at least about 20 days, more preferably at least about 40 days, or even more preferably at least about 60 days.

The terms "patient" and "subject" refer to any human or non-human animal that receives either prophylactic or therapeutic treatment. For example, the methods and compositions described herein can be used to treat a subject or patient having cancer, such as an advanced solid tumor.

The use of the alternative (e.g., "or") should be understood to mean either one, both, or any combination thereof of the alternatives.

As used herein, the indefinite articles "a" or "an" should be understood to refer to "one or more" of any recited or enumerated component.

As used herein, the term "about," in the context of a numerical value or range, means±10% of the numerical value or range.

Any concentration range, percentage range, ratio range, or integer range described herein is to be understood to include the value of any integer within the recited range and, when appropriate, fractions thereof (such as one tenth and one hundredth of an integer), unless otherwise indicated.

Various aspects described herein are described in further detail in the following subsections.

I. Methods of Use

Provided herein are methods of treating cancer using agonistic antibodies that bind to immunostimulatory receptors in an amount (dose) or frequency (schedule of antibody administration) sufficient to achieve and/or maintain a non-saturating receptor occupancy (RO). As shown in the Examples, saturating or near-saturating doses of agonistic antibodies that bind to immunostimulatory receptors (doses that result in >80% RO) result in reduced anti-tumor efficacy, as reflected in markers of T cell activation and proliferation, relative to non-saturating doses (doses that result in an RO of less than about 80%). This suggests treating subjects with cancer by administering sub-saturating doses of agonistic antibodies that bind to immunostimulatory receptors may provide a greater therapeutic benefit than when the antibodies are administered at saturating doses.

Accordingly, provided herein is a method of treating cancer comprising administering to a subject (e.g., a human patient) in need thereof an agonistic antibody that binds to an immunostimulatory receptor, wherein the antibody is administered in an amount or frequency sufficient to achieve and/or maintain an RO of less than about 80%.

Also provided herein is a method of treating cancer in a subject (e.g., a human patient) for whom an amount or frequency of an agonistic antibody that binds to an immunostimulatory receptor sufficient to achieve and/or maintain a RO of less than about 80% has been determined, comprising administering to the subject the sufficient amount of antibody.

Also provided herein is a method of reducing or depleting the number of T regulatory cells in a tumor of a subject with cancer comprising administering to the subject an agonistic antibody that binds to an immunostimulatory receptor, wherein the antibody is administered in an amount or frequency sufficient to achieve and/or maintain a RO of less than about 80%.

Also provided herein is a method of increasing IL-2 and/or IFN-γ production in T cells in a subject with cancer comprising administering to the subject an agonistic antibody that binds to an immunostimulatory receptor, wherein the antibody is administered in an amount or frequency sufficient to achieve and/or maintain a RO of less than about 80%.

Also provided herein is a method of stimulating an immune response in a subject with cancer comprising administering to the subject an agonistic antibody that binds to an immunostimulatory receptor, wherein the antibody is administered in an amount or frequency sufficient to achieve and/or maintain a RO of less than about 80%.

Also provided herein is a method of inhibiting the growth of a tumor or tumor cells in a subject with cancer comprising administering to the subject an agonistic antibody that binds to an immunostimulatory receptor, wherein the antibody is administered in an amount or frequency sufficient to achieve and/or maintain a RO of less than about 80%.

In some embodiments, the agonistic antibody is administered in an amount or frequency sufficient to achieve and/or maintain a RO of less than about 70%, e.g., less than about 60%, less than about 50%, less than about 40%, or less than about 30%. In some embodiments, the agonistic antibody is administered in an amount sufficient to achieve and/or maintain a RO range of about 20% to about 80%, about 20% to about 70%, about 20% to about 60%, about 20% to about 50%, about 20% to about 40%, about 20% to about 30%, about 30% to about 70%, about 40% to about 70%, about 50% to about 70%, about 60% to about 70%, about 30% to about 60%, or about 30% to about 50%.

In certain embodiments of the methods described herein, the agonistic antibody is administered in an amount or frequency sufficient to achieve and/or maintain a RO of less than about 20%, for example, less than about 15%, less than about 10%, less than about 5%, or from about 5% to about 20%, from about 10% to about 20%, or from about 15% to about 20%. In some embodiments, sub-20% RO is achieved and/or maintained with intermittent or pulse dosing of a subject (e.g., a human patient). For example, pulse dosing may entail a combination therapy of the agonistic antibody and an additional agent, wherein the agonistic antibody is administered every 8 weeks or 12 weeks, and the additional agent (e.g., anti-PD1 antibody) is administered every 4 weeks.

In some embodiments, RO is measured on day 1 after cycle 1 in an antibody therapy regimen. In some embodiments, RO is measured mid-cycle in an antibody therapy regimen. In some embodiments, RO is measured at the beginning of a cycle of an antibody therapy regimen. In some embodiments, RO is measured on multiple days in a cycle or cycles of an antibody therapy regimen. For example, in one embodiment, RO is measured on days 1, 7, and/or 14, and at a set interval thereafter (e.g., every 2 weeks), of a 14-day cycle. In certain embodiments, RO is measured when antibody concentrations are near Cmax, Cmin, and/or Ctrough, and/or at the peak of an induced immune response when the expression of the immunostimulatory receptor is predicted to be highest (e.g., days 7-14 post-dose).

Methods of measuring RO are well known in the art. For example, RO can be measured in biological samples (e.g., blood) using flow cytometry with a fluorescently-labeled version of the antibody of interest, as described in, e.g., Example 7A. Methods for measuring receptor occupancy have been reviewed in detail in, e.g., Liang et al., *Cytometry B Clin Cytom* 2016; 90:117-27, Ciccimaro et al. *Anal Chem* 2017; 89:5115-512. Affinity extraction liquid chromatography-mass spectrometry (AE LC-MS) can also be used to measure RO from peripheral blood as well as in tissues by assessing the total levels of agonistic antibody, total level of the immunostimulatory receptor of interest, as well as the complex.

In some embodiments, the RO of agonistic antibodies that bind to immunostimulatory receptors may be used to inform human dose selection. For example, provided herein are methods of treating cancer comprising (a) administering to a subject in need thereof an antibody that specifically binds to an immunostimulatory receptor, (b) measuring RO in a sample from the subject, and (c) determining an amount of the antibody to administer to the subject or a schedule of antibody administration based on the measured RO and/or RO range.

In some embodiments, provided herein are methods of selecting an effective amount or a schedule of antibody administration of a therapeutic agonistic antibody that specifically binds to an immunostimulatory receptor for the treatment of a subject with cancer comprising:
 (a) administering the antibody to the subject;
 (b) obtaining a sample (e.g., blood) from the subject;
 (c) determining RO on cells in the sample; and
 (d) selecting an amount of antibody or a schedule of antibody administration that is sufficient to achieve and/or maintain a RO or RO range of less than about 80% (or less than about 70%, less than about 60%, less than about 50%, less than about 40%, less than about 50%, about 20% to about 70%, about 20% to about 60%, about 20% to about 50%, about 20% to about 40%, or about 20% to about 30%).

RO of an agonistic antibody can be initially determined in pre-clinical animal models to inform dosing in other mammals, e.g., humans. For example, in some embodiments, provided herein are methods of selecting an effective amount or schedule of antibody administration of a therapeutic agonistic antibody that specifically binds to an immunostimulatory receptor for the treatment of a subject with cancer comprising:
 (a) administering the antibody to an animal model (e.g., a mouse tumor model, monkey tumor models);
 (b) obtaining a sample (e.g., blood) from the animal model;
 (c) determining RO of the antibody in the sample;

(d) using the RO obtained from step (c) to project/predict an expected RO in the subject; and (e) selecting an amount of the antibody or schedule of antibody administration that is sufficient to achieve and/or maintain a RO or RO range of less than about 80% to administer to the subject (or an RO of less than about 70%, less than about 60%, less than about 50%, less than about 40%, less than about 50%, about 20% to about 70%, about 20% to about 60%, about 20% to about 50%, about 20% to about 40%, or about 20% to about 30%).

In certain embodiments, an effective amount of antibody is defined based on a RO range at which the antibody exhibits therapeutic efficacy (e.g., anti-tumor activity). Accordingly, also provided herein are methods for determining an effective RO range of an agonistic antibody that specifically binds to an immunostimulatory receptor at which the antibody achieves a therapeutic effect, e.g., anti-tumor activity comprising:

(a) administering the antibody to, e.g., an animal model (e.g., a mouse tumor model) at different amounts or different frequencies;

(b) obtaining a sample (e.g., blood) from the animals;

(c) measuring RO of the antibody in the sample to obtain a dose-response RO curve;

(d) determining an amount of or frequency of administering the antibody that results in a therapeutic effect (e.g., anti-tumor activity) and correlating it with a range of RO.

In some embodiments, the method further comprises a step of projecting/predicting an expected RO range of the agonistic antibody to a subject (e.g., a human patient) based on the RO range determined in step (d).

In some embodiments, provided herein are methods of selecting an effective amount or schedule of antibody administration of a therapeutic agonistic antibody that specifically binds to an immunostimulatory receptor for the treatment of a subject with cancer comprising:

(a) obtaining samples (e.g., tumor biopsy samples) from patients treated with the antibody;

(b) determining RO of the antibody in the sample;

(c) using the RO obtained from step (b) to determine an expected RO in the subject; and (d) selecting an amount of the antibody or schedule of antibody administration that is sufficient to achieve and/or maintain a RO of less than about 80% to administer to the subject (or an RO of less than about 70%, less than about 60%, less than about 50%, less than about 40%, less than about 50%, about 20% to about 70%, about 20% to about 60%, about 20% to about 50%, about 20% to about 40%, or about 20% to about 30%).

In some embodiments, an expected RO and/or RO range in a human patient can be projected/predicted based on a RO and/or RO range associated with therapeutic efficacy (e.g., anti-tumor activity) from preclinical data or by retrospective analysis.

In the preclinical setting, human RO can be calculated, for example, using the dissociation constant Kd determined from surface plasmon resonance or the binding $EC_{50}$ obtained from an in vitro human cell line (Muller P Y and Brennan F R, *Clin Pharmacol Ther.* 2009; 85:247-58; Saber H et al., *Regul Toxicol Pharmacol.* 2016; 81:448-56). However, because of limitations (e.g., lack of competing ligand) of various in vitro systems, human RO predictions can be substantiated by evaluating how well the in vitro RO in an animal species correlates with the in vivo RO observed in that species (Yang Z et al., *J Pharmacol Exp Ther.* 2015; 355:506-515). Clinically, population pharmacokinetic-pharmacodynamic (PK-PD) modeling can be conducted to determine a relationship between drug concentrations and RO data (Rosario M C et al., *Br J Clin Pharmacol.* 2008; 65:86-94), from which human RO data at different dosage regimens can be predicted. The predicted/projected RO can then be used to determine an effective human dose or schedule of antibody administration of the agonistic therapeutic antibody, e.g., a dose or frequency sufficient to achieve and/or maintain a RO or RO range of less than about 80% (or less than about 70%, less than about 60%, less than about 50%, less than about 40%, less than about 50%, about 20% to about 70%, about 20% to about 60%, about 20% to about 50%, about 20% to about 40%, or about 20% to about 30%) in a human patient with cancer.

Suitable pre-clinical animal models for use in projecting an expected RO and/or RO range of an agonistic antibody that binds to an immunostimulatory receptor include, but are not limited to, mouse tumor models (e.g., CT26 mouse syngeneic tumor model), mouse vaccination models, monkey vaccination models, and in vitro stimulation model systems utilizing primary human leukocyte populations.

For retrospective analysis, RO can be determined in samples obtained from patients treated with the agonistic antibody that binds to an immunostimulatory receptor. Samples from patients can be, for example, tumor biopsies, blood, and isolated peripheral blood mononuclear cells. The RO obtained from retrospective analysis can then be used to inform doses or schedule of administration (e.g., doses or frequencies sufficient to achieve and/or maintain an RO of less than about 80%) to administer to human patients with cancer.

In some embodiments, provided herein are methods of treating cancer comprising administering an effective amount or a schedule of antibody administration of a therapeutic agonistic antibody that specifically binds to an immunostimulatory receptor to a subject in need thereof, wherein the amount of antibody to administer or schedule of antibody administration has been selected according to the dose selection methods described above.

In some embodiments, provided herein are methods of treating cancer in a subject (e.g., a human patient) for whom an amount of therapeutic agonistic antibody or a schedule of antibody administration sufficient to achieve and/or maintain an RO and/or RO range of less than about 80% (or less than about 70%, less than about 60%, less than about 50%, less than about 40%, less than about 50%, about 20% to about 70%, about 20% to about 60%, about 20% to about 50%, about 20% to about 40%, or about 20% to about 30%) has been determined using the methods described herein, comprising administering the sufficient amount or schedule of administration of the therapeutic agonistic antibody to the subject.

Also provided herein is a method of monitoring the level of a therapeutic agonistic antibody that specifically binds to an immunostimulatory receptor in a subject being treated for cancer, comprising:

(a) obtaining a sample (e.g., blood) from the subject;

(b) determining RO (i.e., occupancy of the receptor by the antibody) in the sample;

(c) reducing the dose or frequency of administration of the antibody if the RO is greater than about 80%, or increasing the dose or frequency of the antibody if the RO is less than about 20%;

(d) optionally repeating steps (a)-(c) until a dose of the antibody or a schedule of antibody administration sufficient to achieve and/or maintain an RO of about 20% to about 80%, about 20% to about 70%, about 20% to about 60%, about 20% to about 50%, about 20% to about 40%, or about 20% to about 30% is achieved.

In another embodiment, provided herein is a method of monitoring the level of a therapeutic agonistic antibody that specifically binds to an immunostimulatory receptor in a subject being treated for cancer, comprising:

(a) obtaining a sample (e.g., blood) from the subject;
(b) determining RO (i.e., occupancy of the receptor by the antibody) in the sample;
(c) establishing a PK-PD relationship between antibody concentration and RO for predicting RO of a dose regimen and/or dose frequency;
(d) selecting a dose and/or schedule of antibody administration that would achieve and/or maintain a RO and/or RO range of about 20% to about 80%, about 20% to about 70%, about 20% to about 60%, about 20% to about 50%, about 20% to about 40%, or about 20% to about 30%.

Also provided herein are methods of treating cancer comprising administering to a subject in need thereof an agonistic antibody that specifically binds to an immunostimulatory receptor and an additional therapy, wherein the additional therapy is administered at a fixed frequency and the agonistic antibody is administered at a frequency that is sufficient to achieve and/or maintain an RO and/or RO range of less than about 80% (or less than about 70%, less than about 60%, less than about 50%, less than about 40%, less than about 50%, about 20% to about 70%, about 20% to about 60%, about 20% to about 50%, about 20% to about 40%, or about 20% to about 30%). In some embodiments, the frequency of dosing of the agonistic antibody is determined using the dose selection methods described above.

In some embodiments of the methods described herein, the immunostimulatory receptor is a co-stimulatory receptor, for example, a receptor selected from the group consisting of a member of the tumor necrosis factor receptor superfamily (TNFRSF), ICOS (CD278), CD28, LIGHT, CD40L, TIM1, SLAM, CD1, CD2, CD226, LFA-1 (CD11A, CD18), CD2, CD5, CD7, CD30, CD54, CD97, CD154, CD160, LIGHT, NKG2C, SLAMF7, and NKp80.

In some embodiments, the co-stimulatory receptor is a member of the tumor necrosis factor receptor superfamily (TNFRSF). Accordingly, in some embodiments, the agonistic antibodies used in the methods described herein bind to TNFR1, TNFR2, HVEM, LTβR, OX40, CD27, CD40, FAS, DCR3, CD30, 4-1BB, TRAILR1, TRAILR2, TRAILR3, TRAILR4, OPG, RANK, FN14, TACI, BAFFR, BCMA, GITR, TROY, DR3 (death receptor 3), DR6 (death receptor 6), XEDAR (ectodysplasin A2 receptor), or NGFR.

In a particular embodiment, the immunostimulatory receptor is OX40. Accordingly, provided herein is a method of treating cancer comprising administering to a subject in need thereof an agonistic antibody that specifically binds to OX40 (e.g., OX40.21), wherein the agonistic antibody is administered in an amount or frequency sufficient to achieve and/or maintain an RO and/or RO range of less than about 80% (or less than about 70%, less than about 60%, less than about 50%, less than about 40%, less than about 50%, about 20% to about 70%, about 20% to about 60%, about 20% to about 50%, about 20% to about 40%, or about 20% to about 30%) in the subject.

In some embodiments, a method of treating cancer described herein comprises administering to a subject in need thereof an effective amount of each of an anti-OX40 antibody and anti-PD-1 antibody, wherein the anti-OX40 and anti-PD-1 antibodies are administered for at least one administration cycle, wherein the cycle is a period of 12 weeks, wherein for each of the at least one cycles, at least one dose of the anti-OX40 antibody is administered at a fixed dose of about 1, 3, 10, 20, 40, 50, 80, 100, 130, 150, 180, 200, 240 or 280 mg and at least 3 doses of the anti-PD-1 antibody are administered at fixed dose of about 50, 80, 100, 120, 150, 180, 200, 240, 480, 720, or 960 mg. In one embodiment, for each of the at least one cycles, one dose of the anti-OX40 antibody is administered at a fixed dose of about 20, 40, or 80 mg and 3 doses of the anti-PD-1 antibody are administered at fixed dose of about 480 mg. In one embodiment, for each of the at least one cycles, one dose of the anti-OX40 antibody is administered at a fixed dose of about 20 mg and 3 doses of the anti-PD-1 antibody are administered at fixed dose of about 480 mg. In one embodiment, for each of the at least one cycles, one dose of the anti-OX40 antibody is administered at a fixed dose of about 40 mg and 3 doses of the anti-PD-1 antibody are administered at fixed dose of about 480. In one embodiment, for each of the at least one cycles, one dose of the anti-OX40 antibody is administered at a fixed dose of about 80 mg and 3 doses of the anti-PD-1 antibody are administered at fixed dose of about 480. In one embodiment, the anti-PD-1 antibody is administered on Days 1, 29, and 57 of each cycle. In one embodiment, the anti-OX40 antibody is administered on Day 1 of each cycle. In one embodiment, the anti-PD-1 antibody is administered on Days 1, 29, and 57 of each cycle and the anti-OX40 antibody is administered on Day 1 of each cycle. In one embodiment, 12-week administration cycle can be repeated, as necessary. In one embodiment, the administration consists of up to 9 cycles. In one embodiment, the administration consists of 1, 2, 3, 4, 5, 6, 7, 8, or 9 cycles. In one embodiment, the OX-40 antibody comprises OX40.21. In one embodiment, the anti-PD-1 antibody comprises nivolumab. In one embodiment, the cancer is chosen from bladder, cervical, renal cell, testicular, colorectal, lung, head and neck, and ovarian cancers. In one embodiment, the cancer is bladder cancer. In one embodiment, the subject is a human subject.

Also provided is a combination therapy with an agonistic antibody that binds to an immunostimulatory receptor and an additional agent. In such embodiments, an effective amount the agonistic antibody (e.g., anti-OX40 antibody) may be substantially lower than when the agonistic antibody is used alone (i.e., in monotherapy).

Accordingly, provided herein is a method for treating cancer comprising administering to a subject in need thereof an agonistic antibody that specifically binds to OX40 (e.g., MEDI6469, MEDI0562, PF-04518600, MOXR0916, GSK3174998, and antibodies described in WO2016/196228 (e.g., OX40.21)) and an additional therapy (non-limiting examples include an anti-PD1 antibody, an anti-PDL1 antibody, an anti-LAG3 antibody, an anti-CTLA4 antibody, and -TGFβ antibody), wherein the agonistic antibody is administered in an amount or frequency sufficient to achieve and/or maintain a RO and/or RO range of less than about 80% (or less than about 70%, less than about 60%, less than about 50%, less than about 40%, less than about 50%, about 20% to about 70%, about 20% to about 60%, about 20% to about 50%, about 20% to about 40%, or about 20% to about 30%) in the subject.

In some embodiments, the anti-OX40 antibody is administered at a different frequency than the additional therapy. For example, the additional therapy is administered at a fixed frequency, and the anti-OX40 antibody is administered at a dose and/or frequency that is sufficient to achieve a RO and/or RO range of less than about 80% (or less than about 70%, less than about 60%, less than about 50%, less than about 40%, less than about 50%, about 20% to about 70%, about 20% to about 60%, about 20% to about 50%, about 20% to about 40%, or about 20% to about 30%).

In some embodiments, the agonistic antibodies that bind to immunostimulatory receptors (e.g., an anti-OX40 antibody such as OX40.21) are pulse administered when used in combination with an additional therapy (e.g., nivolumab). In some embodiments, the agonistic antibody is pulse administered in order to achieve and/or maintain an RO of less than about 80% (or less than about 70%, less than about 60%, less than about 50%, less than about 40%, less than about 50%, about 20% to about 70%, about 20% to about 60%, about 20% to about 50%, about 20% to about 40%, or about 20% to about 30%). For example, in one embodiment, pulse administering may entail a combination therapy of the agonistic antibody and an additional agent, wherein the agonistic antibody is administered every 8 weeks or 12 weeks, and the additional agent (e.g., anti-PD1 antibody) is administered every 4 weeks.

Markers of T cell activation can be monitored in the subject being treated with an agonistic antibody that binds to an immunostimulatory receptor to confirm that an effective dose or frequency of the agonistic antibody is being administered. Examples of additional markers of T cell activation that can be monitored (and exhibit the "hook effect") include, but are not limited to, surface expression of the immunostimulatory receptor (e.g., OX40), ICOS, CD44, and Ki67, as well as cytokines that are known to be upregulated during an immune response (e.g., IFN-γ, IL-2)). Methods for measuring levels of the above markers are well known in the art (e.g., ELISA). T cell proliferation can be monitored by, e.g., 3[H]-thymidine incorporation assays.

When the immunostimulatory receptor targeted in the methods described herein is OX40, soluble OX40 (sOX40) can be used as a marker to monitor therapeutic efficacy of agonistic antibody treatment, since sOX40 also exhibits the so-called "hook effect" at high RO levels (see, e.g., Example 8). An exemplary method (ELISA) for determining sOX40 levels is provided in Example 8.

Cancers whose growth may be treated or monitored with the methods described herein include cancers typically responsive to immunotherapy and those that are not typically responsive to immunotherapy. Cancers may be cancers with solid tumors or blood malignancies (liquid tumors). Non-limiting examples of cancers for treatment include squamous cell carcinoma, small-cell lung cancer, non-small cell lung cancer, squamous non-small cell lung cancer (NSCLC), non-squamous NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, T-cell lymphoma, environmentally-induced cancers including those induced by asbestos, virus-related cancers or cancers of viral origin (e.g., human papilloma virus (HPV-related or -originating tumors)), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CIVIL), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, B cell lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers.

The methods described herein may also be used to treat metastatic cancers, unresectable, and/or refractory cancers (e.g., cancers refractory to previous immunotherapy, e.g., with a blocking CTLA-4 or PD-1 antibody), and recurrent cancers.

In some embodiments, the patient to be treated with the methods disclosed herein has an advanced solid tumor. For example, in one embodiment, the patient has cervical cancer. In another embodiment, the patient has colorectal (CRC) cancer. In another embodiment, the patient has bladder cancer (e.g., unresectable locally advanced or metastatic bladder cancer). In another embodiment, the patient has ovarian cancer (e.g., unresectable locally advanced or metastatic ovarian cancer).

In one embodiment, the patient being treated with the methods described herein has non-small cell lung cancer (NSCLC). In another embodiment, the patient has squamous cell carcinoma of the head and neck (SCCHN). In another embodiment, the patient has B-cell non-Hodgkin's lymphoma (B-NHL). In another embodiment, the patient has myeloma. In another embodiment, the patient has melanoma. In another embodiment, the patient has diffuse large B-cell lymphoma (DLBCL).

In one embodiment, the patient being treated with the methods described herein has cervical cancer. In one embodiment, the cervical cancer is unresectable, metastatic, or recurrent with documented disease progression.

In one embodiment, the patient being treated with the methods described herein has renal cell carcinoma. In one embodiment, the renal cell carcinoma is metastatic renal cell carcinoma. In one embodiment, the renal cell carcinoma is a renal cell carcinoma with a clear-cell component.

In one embodiment, the patient being treated with the methods described herein has testicular cancer.

In one embodiment, the patient being treated with the methods described herein has colorectal cancer. In one embodiment, the colorectal cancer is a microsatellite instability-high (MSI-H) colorectal cancer. In one embodiment, the colorectal cancer is a microsatellite stable colorectal cancer. In one embodiment, the colorectal cancer is a mismatch repair-deficient colorectal cancer.

In one embodiment, the patient being treated with the methods described herein has lung cancer.

In one embodiment, the patient being treated with the methods described herein has head and neck cancer. In one embodiment, the head and neck cancer is squamous cell carcinoma.

In one embodiment, the patient being treated with the methods described herein has ovarian cancer. In one embodiment, the ovarian cancer is unresectable locally advanced ovarian cancer. In one embodiment, the ovarian cancer is metastatic ovarian cancer. In one embodiment, the ovarian cancer is recurrent platinum-sensitive ovarian cancer.

In some embodiments, the patient being treated with the methods described herein has a cancer that exhibited an inadequate response to a prior treatment, e.g., a prior treatment with an immuno-oncology drug, or patients having a cancer that is refractory or resistant, either intrinsically refractory or resistant, or wherein the resistance or refractory state is acquired. In some embodiments, the patient has not previously received (i.e., been treated with) an immuno-oncology agent, e.g., a PD-1 pathway antagonist.

In some embodiments, the methods described herein may further include a standard of care treatment (e.g., surgery, radiation, and chemotherapy). In other embodiments, the methods may be performed as a maintenance therapy, e.g., a therapy that is intended to prevent the occurrence or recurrence of tumors.

In some embodiments, the agonistic antibody that binds to an immunostimulatory receptor such as a TNF and TNFR family molecule (e.g., OX40) is given to a subject as an adjunctive therapy. In some embodiments, the agonistic antibody that binds to an immunostimulatory receptor such as a TNF and TNFR family molecule (e.g., OX40) is used as a first-, second-, or third-line treatment.

In some embodiments, the agonistic antibody that binds to an immunostimulatory receptor such as a TNF and TNFR family molecule (e.g., OX40) can be administered as a monotherapy, or as the only immunostimulating therapy.

In other embodiments, the agonistic antibody that binds to an immunostimulatory receptor such as a TNF and TNFR family molecule (e.g., OX40) can be administered as a part of combination therapy, as described below.

The agonistic antibody that specifically binds to an immunostimulatory receptor such as a TNF and TNFR family molecule (e.g., OX40) can be combined with an immuno-oncology agent, e.g., (i) an agonist of a immunostimulatory (e.g., co-stimulatory) molecule (e.g., receptor or ligand) and/or (ii) an antagonist of an immunoinhibitory molecule (e.g., receptor or ligand) on immune cells, such as T cells, both of which result in amplifying immune responses, such as antigen-specific T cell responses. In certain aspects, an immuno-oncology agent is (i) an agonist of an immunostimulatory (including a co-stimulatory) molecule (e.g., receptor or ligand) or (ii) an antagonist of an immunoinhibitory (including a co-inhibitory) molecule (e.g., receptor or ligand) present on cells involved in innate immunity, e.g., NK cells. Such immuno-oncology agents are often referred to as immune checkpoint regulators, e.g., immune checkpoint inhibitor or immune checkpoint stimulator.

In some embodiments, the agonistic antibody that specifically binds to an immunostimulatory receptor such as a TNF and TNFR family molecule (e.g., OX40) is administered with an agent that targets a stimulatory or inhibitory molecule that is a member of the immunoglobulin super family (IgSF). In some embodiments, the agonistic antibody that specifically binds to an immunostimulatory receptor may be administered with an agent that targets (or binds specifically to) a member of the B7 family of membrane-bound ligands that includes B7-1, B7-2, B7-H1 (PD-L1), B7-DC (PD-L2), B7-H2 (ICOS-L), B7-H3, B7-H4, B7-H5 (VISTA), and B7-H6, or a co-stimulatory or co-inhibitory receptor binding specifically to a B7 family member.

In some embodiments, the agonistic antibody that specifically binds to an immunostimulatory receptor such as a TNF and TNFR family molecule (e.g., OX40) may also be administered with an agent that targets a member of the TNF and TNFR family of molecules (ligands or receptors), such as CD40 and CD40L, GITR, GITR-L, CD70, CD27L, CD30, CD30L, 4-1BBL, CD137, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDA1, EDA2, TNFR1, Lymphotoxin α/TNFβ, TNFR2, TNFα, LTβR, Lymphotoxin α1β2, FAS, FASL, RELT, DR6, TROY, and NGFR (see, e.g., Tansey (2009) Drug Discovery Today 00:1).

In some embodiments, the agonistic antibody that specifically binds to an immunostimulatory receptor such as a TNF and TNFR family molecule (e.g., OX40) is administered with one or more of the following agents:

(1) An antagonist (inhibitor or blocking agent) of a protein that inhibits T cell activation (e.g., immune checkpoint inhibitors), such as CTLA-4, PD-1, PD-L1, PD-L2, and LAG-3, as described above, and any of the following proteins: TIM-3, Galectin 9, CEACAM-1, BTLA, CD69, Galectin-1, TIGIT, CD113, GPR56, VISTA, B7-H3, B7-H4, 2B4, CD48, GARP, PD1H, LAIR1, TIM-1, and TIM-4; and/or (2) An agonist of a protein that stimulates T cell activation, such as B7-1, B7-2, CD28, 4-1BB (CD137), 4-1BBL, ICOS, ICOS-L, GITR, GITR-L, CD70, CD27, CD40, DR3 and CD28H.

Exemplary agents that modulate one of the above proteins for treating cancer, include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), Atacicept (to TACI), CP-870893 (to CD40), Lucatumumab (to CD40), Dacetuzumab (to CD40), Muromonab-CD3 (to CD3), Ipilumumab (to CTLA-4). In some embodiments, the agonistic antibody that specifically binds to an immunostimulatory receptor is administered with pidilizumab (CT-011).

Other molecules that can be combined with the agonistic antibody that specifically binds to an immunostimulatory receptor such as a TNF and TNFR family molecule (e.g., OX40) for the treatment of cancer include antagonists of inhibitory receptors on NK cells or agonists of activating receptors on NK cells, for example, antagonists of KIR (e.g., lirilumab).

In some embodiments, the agonistic antibody that specifically binds to an immunostimulatory receptor such as a TNF and TNFR family molecule (e.g., OX40) may be administered with antagonists of cytokines that inhibit T cell activation or agonists of cytokines that stimulate T cell activation.

In certain embodiments, the agonistic antibody that specifically binds to an immunostimulatory receptor such as a TNF and TNFR family molecule (e.g., OX40) can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-β, VEGF; "immunosuppressive cytokines") and/or (ii) agonists of stimulatory receptors of the IgSF family, B7 family or the TNF family or of cytokines that stimulate T cell activation, for stimulating an immune response, e.g., for treating proliferative diseases, such as cancer.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

The agonistic antibody that specifically binds to an immunostimulatory receptor such as a TNF and TNFR family molecule (e.g., OX40) may also be administered with agents that inhibit TGF-β signaling.

Additional agents for combination therapy include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Yet other therapies for use in combination therapy include therapies that deplete or block Treg cells, e.g., an agent that specifically binds to CD25.

Another therapy that may be combined with an agonistic antibody that specifically binds to an immunostimulatory receptor such as a TNF and TNFR family molecule (e.g., OX40) is a therapy that inhibits a metabolic enzyme such as indoleamine dioxigenase (IDO), dioxigenase, arginase, or nitric oxide synthetase.

Another class of agents that may be used with agonistic antibodies that specifically binds to an immunostimulatory receptor such as a TNF and TNFR family molecule (e.g., OX40) includes agents that inhibit the formation of adenosine or inhibit the adenosine A2A receptor.

Other therapies for use in combination therapy include those that reverse/prevent T cell anergy or exhaustion and therapies that trigger an innate immune activation and/or inflammation at a tumor site.

In some embodiments, the agonistic antibody that specifically binds to an immunostimulatory receptor such as a TNF and TNFR family molecule (e.g., OX40) may be combined with more than one immuno-oncology agent, and may be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells; a therapy that stimulates positive immune regulation, e.g., agonists that stimulate the CD-137 and/or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

In some embodiments, the agonistic antibody that specifically binds to an immunostimulatory receptor such as a TNF and TNFR family molecule (e.g., OX40) can be used together with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In certain embodiments, the agonistic antibody that specifically binds to an immunostimulatory receptor such as a TNF and TNFR family molecule (e.g., OX40) is administered to a subject together with a BRAF inhibitor if the subject is BRAF V600 mutation positive.

In certain embodiments, the agonistic antibody that specifically binds to an immunostimulatory receptor such as a TNF and TNFR family molecule (e.g., OX40) is administered together with another immunostimulatory antibody, such as an antagonistic anti-PD1 antibody, an antagonistic anti-PDL1 antibody, an antagonistic anti-CTLA4 antibody, an antagonistic anti-LAG3 antibody, the anti-OX40 antibody is administered together with another immunostimulatory antibody. In a particular embodiment, the combination therapy comprises an agonistic anti-OX40 antibody and an antagonistic anti-PD1 antibody.

Suitable PD-1 antagonists for use in the methods described herein, include, without limitation, ligands, antibodies (e.g., monoclonal antibodies and bispecific antibodies), and multivalent agents. In one embodiment, the PD-1 antagonist is a fusion protein, e.g., an Fc fusion protein, such as AMP-244. In one embodiment, the PD-1 antagonist is an anti-PD-1 or anti-PD-L1 antibody. An exemplary anti-PD-1 antibody is nivolumab (BMS-936558) or an antibody that comprises the CDRs or variable regions of one of antibodies 17D8, 2D3, 4H1, 5C4, 7D3, 5F4 and 4A11 described in WO 2006/121168. In certain embodiments, an anti-PD1 antibody is MK-3475 (Lambrolizumab) described in WO2012/145493; and AMP-514 described in WO 2012/145493. Further known PD-1 antibodies and other PD-1 inhibitors include those described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368. Any of the anti-PD-1 antibodies disclosed in WO2013/173223 may also be used. An anti-PD-1 antibody that competes for binding with, and/or binds to the same epitope on PD-1 as, as one of these antibodies may also be used in combination treatments. Another approach to target the PD-1 receptor is the recombinant protein composed of the extracellular domain of PD-L2 (B7-DC) fused to the Fc portion of IgG1, called AMP-224. In certain embodiments, the antibody has at least about 90% variable region amino acid sequence identity with the above-mentioned antibodies.

In certain embodiments, the agonistic antibody that specifically binds to an immunostimulatory receptor such as a TNF and TNFR family molecule (e.g., OX40) is used in combination with nivolumab, which comprises heavy and light chains comprising the sequences shown in SEQ ID NOs: 16 and 17, respectively, or antigen binding fragments and variants thereof. In certain embodiments, the antibody has heavy and light chain CDRs or variable regions of nivolumab. Accordingly, in one embodiment, the antibody comprises CDR1, CDR2, and CDR3 domains of the VH of nivolumab having the sequence set forth in SEQ ID NO: 18, and CDR1, CDR2 and CDR3 domains of the VL of nivolumab having the sequence set forth in SEQ ID NO: 19. In certain embodiments, the antibody comprises CDR1, CDR2 and CDR3 domains comprising the sequences set forth in SEQ ID NOs: 20-22, respectively, and CDR1, CDR2 and CDR3 domains comprising the sequences set forth in SEQ ID NOs: 23-25, respectively. In certain embodiments, the antibody comprises VH and/or VL regions comprising the amino acid sequences set forth in SEQ ID NO: 18 and/or SEQ ID NO: 19, respectively. In certain embodiments, the antibody has at least about 90%, e.g., at least about 90%, 95%, or 99% variable region identity with SEQ ID NO: 18 and/or SEQ ID NO: 19.

Exemplary anti-PD-L1 antibodies include BMS-936559 (referred to as 12A4 in WO 2007/005874 and U.S. Pat. No. 7,943,743), or an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743. In certain embodiments, the anti-PD-L1 antibody is MEDI4736 (also known as Anti-B7-H1), NIPDL3280A (also known as RG7446), MSB0010718C (W02013/79174), or rHigM12B7. Any of the anti-PD-L1 antibodies disclosed in WO2013/173223, WO2011/066389, WO2012/145493, U.S. Pat. Nos. 7,635,757 and 8,217,149 and U.S. Publication No. 2009/145493 may also be used.

Exemplary anti-CTLA-4 antibodies include Yervoy™ (ipilimumab or antibody 10D1, described in PCT Publication WO 01/14424), tremelimumab (formerly ticilimumab, CP-675,206), or an anti-CTLA-4 antibody described in any of the following publications: WO 98/42752; WO 00/37504; U.S. Pat. No. 6,207,156; Hurwitz et al. (1998) *Proc. Natl. Acad. Sci. USA* 95(17):10067-10071; Camacho et al. (2004) *J. Clin. Oncology* 22(145): Abstract No. 2505 (antibody CP-675206); and Mokyr et al. (1998) *Cancer Res.* 58:5301-5304. Any of the anti-CTLA-4 antibodies disclosed in WO2013/173223 may also be used.

In certain embodiments, the agonistic antibody that specifically binds to an immunostimulatory receptor is used in combination with ipilimumab. In certain embodiments, the antibody has heavy and light chain CDRs or variable regions of ipilimumab. Accordingly, in one embodiment, the antibody comprises CDR1, CDR2, and CDR3 domains of the VH of ipilimumab having the sequence set forth in SEQ ID NO: 26, and CDR1, CDR2 and CDR3 domains of the VL of ipilimumab having the sequence set forth in SEQ ID NO: 27. In certain embodiments, the antibody comprises CDR1, CDR2 and CDR3 domains comprising the sequences set forth in SEQ ID NOs: 28-30, respectively, and CDR1, CDR2 and CDR3 domains comprising the sequences set forth in SEQ ID NOs: 31-33, respectively. In certain embodiments, the antibody comprises VH and/or VL regions comprising the amino acid sequences set forth in SEQ ID NO: 26 and/or SEQ ID NO: 27, respectively. In certain embodiments, the antibody has at least about 90%, e.g., at least about 90%, 95%, or 99% variable region identity with SEQ ID NO: 26 or SEQ ID NO: 27.

Exemplary anti-LAG3 antibodies include antibodies comprising the CDRs or variable regions of antibodies 25F7, 26H10, 25E3, 8B7, 11F2 or 17E5, which are described in U.S. Patent Publication No. US2011/0150892, WO10/19570 and WO2014/008218. In one embodiment, an anti-LAG-3 antibody is BMS-986016. Other art recognized anti-LAG-3 antibodies that can be used include IMP731 and IMP-321, described in US 2011/007023, WO08/132601, and WO09/44273.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. Furthermore, if more than one dose of the combination therapy is administered sequentially, the order of the sequential administration can be reversed or kept in the same order at each time point of administration, and sequential administrations can be combined with concurrent administrations, or any combination thereof.

In certain embodiment, a subject having a disease that may benefit from stimulation of the immune system, e.g., cancer or an infectious disease, is treated by administration to the subject an agonistic antibody that specifically binds to an immunostimulatory receptor and an immuno-oncology agent. Exemplary immune-oncology agents include CD137 (4-1BB) agonists (e.g., an agonistic CD137 antibody such as urelumab or PF-05082566 (WO12/32433)); GITR agonists (e.g., an agonistic anti-GITR antibody), CD40 agonists (e.g., an agonistic CD40 antibody); CD40 antagonists (e.g., an antagonistic CD40 antibody such as lucatumumab (HCD122), dacetuzumab (SGN-40), CP-870,893 or Chi Lob 7/4); CD27 agonists (e.g., an agonistic CD27 antibody such as varlilumab (CDX-1127)), MGA271 (to B7H3) (WO11/109400)); KIR antagonists (e.g., lirilumab); IDO antagonists (e.g., INCB-024360 (WO2006/122150, WO07/75598, WO08/36653, WO08/36642), indoximod, NLG-919 (WO09/73620, WO09/1156652, WO11/56652, WO12/142237) or F001287); Toll-like receptor agonists (e.g., TLR2/4 agonists (e.g., Bacillus Calmette-Guerin); TLR7 agonists (e.g., Hiltonol or Imiquimod); TLR7/8 agonists (e.g., Resiquimod); or TLR9 agonists (e.g., CpG7909)); and TGF-β inhibitors (e.g., GC1008, LY2157299, TEW7197, or IMC-TR1).

Optionally, the agonistic antibody that specifically binds to an immunostimulatory receptor as sole immunotherapeutic agent, or a combination of the agonistic antibody and one or more additional immunotherapeutic antibodies (e.g., anti-CTLA-4 and/or anti-PD-1 and/or anti-PD-L1 and/or anti-LAG-3 blockade), can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below). A combination of the agonistic antibody that specifically binds to an immunostimulatory receptor and one or more additional antibodies (e.g., CTLA-4 and/or PD-1 and/or PD-L1 and/or LAG-3 blockade) can also be further combined with standard cancer treatments. For example, a combination of the agonistic antibody that specifically binds to an immunostimulatory receptor and one or more additional antibodies (e.g., CTLA-4 and/or PD-1 and/or PD-L1 and/or LAG-3 blockade) can be effectively combined with chemotherapeutic regimes. In these instances, the dose of other chemotherapeutic reagent administered with the combination can be reduced (Mokyr et al. (1998) *Cancer Research* 58: 5301-5304). For example, such a combination may include the agonistic antibody that specifically binds to an immunostimulatory receptor with or without and an additional antibody (e.g., anti-CTLA-4 antibodies and/or anti-PD-1 antibodies and/or anti-PD-L1 antibodies and/or anti-LAG-3 antibodies), further in combination with decarbazine or interleukin-2 (IL-2) for the treatment of melanoma. The scientific rationale behind combining an agonistic antibody that specifically binds to an immunostimulatory receptor with CTLA-4 and/or PD-1 and/or PD-L1 and/or LAG-3 blockade with chemotherapy is that cell death, which is a consequence of the cytotoxic action of most chemotherapeutic compounds, should result in increased levels of tumor antigen in the antigen presentation pathway. Other combination therapies that may result in synergy with a combination of the agonistic antibody that specifically binds to an immunostimulatory receptor with or without and CTLA-4 and/or PD-1 and/or PD-L1 and/or LAG-3 blockade through cell death include radiation, surgery, or hormone deprivation. Each of these protocols creates a source of tumor antigen in the host. Angiogenesis inhibitors can also be combined with a combination of the agonistic antibody that specifically binds to an immunostimulatory receptor and CTLA-4 and/or PD-1 and/or PD-L1 and/or LAG-3 blockade. Inhibition of angiogenesis leads to tumor cell death, which can be a source of tumor antigen fed into host antigen presentation pathways.

In certain embodiments, the agonistic antibody that specifically binds to an immunostimulatory receptor can be used as the sole immunotherapeutic agent, or a combination of the anti-OX40 antibody and CTLA-4 and/or PD-1 and/or PD-L1 and/or LAG-3 blocking antibodies, can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. The T cell arm of these responses would be augmented by the use of a combination of the agonistic antibody that specifically binds to an immunostimulatory receptor and CTLA-4 and/or PD-1 and/or PD-L1 and/or LAG-3 blockade.

In another example, the agonistic antibody that specifically binds to an immunostimulatory receptor can be used as the sole immunotherapeutic agent, or a combination of the agonistic antibody that specifically binds to an immunostimulatory receptor and additional immunostimulating agent, e.g., antagonistic anti-CTLA-4 antibody and/or antagonistic anti-PD-1 antibody and/or antagonistic anti-PD-L1 antibody and/or antagonistic LAG-3 agent (e.g., antibody) can be used in conjunction with an anti-neoplastic antibody, such as Rituxan® (rituximab), Herceptin® (trastuzumab), Bexxar® (tositumomab), Zevalin® (ibritumomab), Campath® (alemtuzumab), Lymphocide® (epratuzumab), Avastin® (bevacizumab), and Tarceva® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by the immunostimulating agent (e.g., antagonistic CTLA-4, PD-1, PD-L1 or LAG-3 agent, e.g., antibody). In an exemplary embodiment, a treatment of a hyperproliferative disease (e.g., a cancer tumor) can include an anti-cancer agent (e.g., antibody) in combination with the agonistic antibody that specifically binds to an immunostimulatory receptor and optionally an additional immunostimulating agent, e.g., antagonistic anti-CTLA-4 and/or anti-PD-1 and/or anti-PD-L1 and/or anti-LAG-3 agent (e.g., antibody), concurrently or sequentially or any combination thereof, which can potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) *J Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be further combined with the agonistic antibody that specifically binds to an immunostimulatory receptor, with or without an additional immunostimulating agent, e.g., an antagonistic anti-CTLA-4 and/or anti-PD-1 and/or anti-PD-L1 and/or anti-LAG-3 agent, such as antibody, to counteract the effects of immunosuppressive agents and favor anti-tumor immune responses by the host.

Other agents (e.g., antibodies) that can be used to activate host immune responsiveness can be further used in combination with the agonistic antibody that specifically binds to an immunostimulatory receptor with or without an additional immunostimulating agent, such as an antagonistic anti-CTLA-4 and/or anti-PD-1 and/or anti-PD-L1 and/or anti-LAG-3 antibody. These include molecules on the surface of dendritic cells that activate DC function and antigen presentation. Anti-CD40 antibodies (Ridge et al., supra) can be used in conjunction with the agonistic antibody that specifically binds to an immunostimulatory receptor and optionally an additional immunostimulating agent, e.g., an anti-CTLA-4 and/or anti-PD-1 and/or anti-PD-L1 and/or anti-LAG-3 agent, e.g., antibody. Other activating antibodies to T cell costimulatory molecules Weinberg et al., supra, Melero et al. supra, Hutloff et al., supra, may also provide for increased levels of T cell activation.

As discussed above, bone marrow transplantation is currently being used to treat a variety of tumors of hematopoietic origin. An agonistic antibody that specifically binds to an immunostimulatory receptor alone or combined with CTLA-4 and/or PD-1 and/or PD-L1 and/or LAG-3 blockade can be used to increase the effectiveness of the donor engrafted tumor specific T cells.

Several experimental treatment protocols involve ex vivo activation and expansion of antigen specific T cells and adoptive transfer of these cells into recipients in order to antigen-specific T cells against tumor (Greenberg & Riddell, supra). These methods can also be used to activate T cell responses to infectious agents such as CMV. Ex vivo activation in the presence of the agonistic antibody that specifically binds to an immunostimulatory receptor with or without an additional immunostimulating therapy, e.g., antagonistic anti-CTLA-4 and/or anti-PD-1 and/or anti-PD-L1 and/or anti-LAG-3 antibodies, can be expected to increase the frequency and activity of the adoptively transferred T cells.

The agonistic antibody that specifically binds to an immunostimulatory receptor and combination antibody therapies described herein can be used in combination (e.g., simultaneously or separately) with an additional treatment, such as irradiation, chemotherapy (e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, 5-fu, or camptothecin+ apo2l/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 inhibitor (e.g., INCB24360, indoximod, NLG-919, or F001287), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., Nat Med 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., Avastin), synthetic triterpenoids (see Hyer et al., Cancer Research 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), Trastuzumab, Cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3β inhibitors, IAP inhibitors, and/or genotoxic drugs.

The agonistic antibody that specifically binds to an immunostimulatory receptor and combination antibody therapies described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Anti-proliferative agents, including, without limitation, taxanes, paclitaxel (paclitaxel is commercially available as TAXOL'), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discodermolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with the agonistic antibody that specifically binds to an immunostimulatory receptor, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™, can also be administered to the patient. When employing the methods or compositions described herein, other agents used in the modulation of tumor growth or metastasis in a clinical setting, such as antimimetics, can also be administered as desired.

In certain embodiments, the agonistic antibody that specifically binds to an immunostimulatory receptor (e.g., anti-OX40 antibody such as OX40.21) is administered in combination (concurrently or separately) with nivolumab to treat a patient with cancer, for example, colorectal or bladder cancer.

In certain embodiments, the agonistic antibody that specifically binds to an immunostimulatory receptor (e.g., anti-OX40 antibody such as OX40.21) is administered in combination (concurrently or separately) with ipilimumab to treat a patient with cancer, for example, ovarian, bladder, or prostate cancer.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

II. Agonistic Antibodies that Bind to Immunostimulatory Receptors

Agonistic antibodies that bind to immunostimulatory receptors that are suitable for use in the methods described herein (including combination therapies) include newly developed agonistic antibodies, as well as agonistic antibodies which are known in the art (including antibodies that compete with or bind to the same epitope as the antibodies). New agonistic antibodies targeting immunostimulatory receptors can be obtained using standard antibody production and screening techniques, and can be tested for agonist activity using art-recognized assays.

In certain embodiments, suitable agonistic antibodies for use in the methods described herein bind to and activate immunostimulatory receptors and their downstream signaling pathway(s), and thereby stimulate an immune response. In some embodiments, the agonistic antibodies that bind to immunostimulatory receptors for use in the methods described herein exhibit a "hook effect," wherein near-saturating or saturating concentrations of the antibody (e.g., concentrations that result in >80% RO) result in diminished efficacy compared to concentrations resulting in sub-80% RO in functional in vitro (e.g., cytokine production, proliferation assays, surface expression of receptors) and/or in vivo assays (e.g., anti-tumor efficacy).

In some embodiments, the agonistic antibody binds to a co-stimulatory receptor, for example, a co-stimulatory receptor selected from the group consisting of: a member of the tumor necrosis factor receptor superfamily (TNFRSF), ICOS (CD278), CD28, LIGHT, CD40L, TIM1, SLAM, CD1, CD2, CD226, LFA-1 (CD11A, CD18), CD5, CD7, CD30, CD54, CD97, CD154, CD160, LIGHT, NKG2C, SLAMF7, NKp80, and TGF-β. In some embodiments, the agonistic antibodies that bind to co-stimulatory receptors for use in the methods described herein exhibit a "hook effect."

In some embodiments, the agonistic antibody binds to a member of the TNFRSF, for example, a receptor selected from the group consisting of: TNFR1, TNFR2, HVEM, LTβR, OX40 (CD134/TNFRSF4), CD27 (TNFRSF7), CD40, FAS, DCR3, CD30, 4-1BB, TRAILR1, TRAILR2, TRAILR3, TRAILR4, OPG, RANK, FN14, TACI, BAFFR, BCMA, GITR, TROY, DR3 (death receptor 3), DR6 (death receptor 6), XEDAR (ectodysplasin A2 receptor), and NGFR. In some embodiments, the agonistic antibodies that bind to members of the TNFRSF for use in the methods described herein exhibit a "hook effect."

In some embodiments, the agonistic antibody specifically binds to OX40, e.g., an agonistic anti-OX40 antibody that exhibits a "hook effect". Exemplary agonistic anti-OX40 antibodies are MEDI6469, MEDI0562, PF-04518600, MOXR0916, GSK3174998, RG-7888 (vonlerolizumab), INCAGN-1949, and antibodies described in WO2016/196228 (e.g., OX40.21); WO/1995/012673; WO199942585; WO/2014/148895; WO15153513; WO15153514; WO/2013/038191; WO2016057667; WO03106498; WO12027328; WO13028231; WO2016200836; WO 17063162; WO17134292; WO 17096179; WO 17096281; WO 17096182; the contents of each are herein incorporated by reference in their entireties. In some embodiments, the agonistic anti-OX40 antibody exhibits the following properties:

(a) binds to membrane-bound human OX40, e.g., with an $EC_{50}$ of 1 nM or less (e.g., 0.01 nM to 1 nM), e.g., as measured by FACS;

(b) binds to cynomolgus OX40, e.g., binding to membrane bound cynomolgus OX40, e.g., with an $EC_{50}$ of 10 nM or less (e.g., 0.01 nM to 10 nM), e.g., as measured by FACS;

(c) binds to soluble human OX40, e.g., with a $K_D$ of 10 nM or less (e.g., 0.01 nM to 10 nM), e.g., as measured by BIACORE® SPR analysis;

(d) induces or enhances T cell activation, as evidenced by (i) increased IL-2 and/or IFN-γ production in OX40-expressing T cells and/or (ii) enhanced T cell proliferation; and (e) inhibits the binding of OX40 ligand to OX40, e.g., with an $EC_{50}$ of 1 nM or less as measured by FACS, e.g., in an assay with hOX40-293 cells.

In some embodiments, the agonistic anti-OX40 antibody binds to Fc receptors, for example, Fcγ receptors.

In some embodiments, the agonistic anti-OX40 antibody induces or enhances T cell activation through multivalent cross-linking.

In some embodiments, the agonistic anti-OX40 antibodies may stimulate or enhance an immune response, e.g., by activating $T_{eff}$ cells, limiting the suppression of T-effector cells by Treg cells, depleting and/or inhibiting tumor Treg cells and/or activating NK cells, e.g., in the tumor. For example, the agonistic anti-OX40 antibodies may activate or costimulate $T_{eff}$ cells as evidenced, e.g., by enhanced cytokine (e.g., IL-2 and IFN-γ) secretion and/or enhanced proliferation. In certain embodiments, the agonistic anti-OX40 antibody increases IL-2 secretion by a factor of 50%, 100% (i.e., 2 fold), 3 fold, 4 fold, 5 fold or more, optionally with a maximum of up to 10 fold, 30 fold, 100 fold, as measured, e.g., on primary human T cells or T cells expressing human OX40. In certain embodiments, the agonistic anti-OX40 antibody increases IFN-γ secretion by a factor of 50%, 100% (i.e., 2 fold), 3 fold, 4 fold, 5 fold or more, optionally with a maximum of up to 10 fold, 30 fold, 100 fold, as measured, e.g., on primary human T cells or T cells expressing human OX40.

In some embodiments, the agonistic anti-OX40 antibody binds the C1q component of human complement. In some embodiments, the agonistic anti-OX40 antibody induces NK cell-mediated lysis of activated CD4+ T cells. In some embodiments, the agonistic anti-OX40 antibody promotes macrophage-mediated phagocytosis of OX40 expressing cells. In some embodiments, the agonistic anti-OX40 antibody inhibits regulatory T cell-mediated suppression of CD4+ T cell proliferation.

In some embodiments, the agonistic anti-OX40 antibody binds to both human and cynomolgus OX40.

In some embodiments, the agonistic anti-OX40 antibody binds to all or a portion of the sequence DVVSSKPCK-PCTWCNLR (SEQ ID NO: 15) in human OX40.

In a particular embodiment, the agonistic anti-OX40 antibody used in the methods described herein is OX40.21. The heavy and light chain sequences, variable region sequences, and CDR sequences of OX40.21 are provided below.

In some embodiments, the anti-OX40 antibody comprises heavy and light chain variable region sequences set forth in SEQ ID NOs: 11 and 12, respectively.

In some embodiments, the anti-OX40 antibody comprises heavy and light chain sequences set forth in SEQ ID NOs: 13 and 14, respectively.

Exemplary agonistic antibodies that bind to immunostimulatory receptors include anti-4-1BB antibodies (e.g., urelumab (BMS-663513) and PF-05082566), anti-GITR antibodies (e.g., TRX518, MK-4166, MK-1248, GWN323, and antibodies disclosed in WO2017087678, the contents of which are herein incorporated by reference in their entirety), anti-CD27 antibodies (e.g., varlilumab (CDX-1127)), anti-ICOS antibodies (e.g., MEDI-570, GSK3359609, JTX-2011), anti-DR3 antibodies (e.g., PTX-25), and anti-CD40 antibodies (e.g., CP-870,893, dacetuzmumab, Chi Lob 7/4, lucatumumab, APX005M, ADC-1013, JNJ-64457107,

TABLE 2

Summary of OX40.21 sequences

| SEQ ID | | OX40.21 sequences |
|---|---|---|
| 5 | VHCDR1 | SYAMY |
| 6 | VHCDR2 | AIDTDAGTFYADSVRG |
| 7 | VHCDR3 | LGEGYFFDY |
| 8 | VLCDR1 | RASQSVSSYLA |
| 9 | VLCDR2 | DASNRAT |
| 10 | VLCDR3 | QQRSNWPPT |
| 11 | VH | EVQLVQSGGGLVQPGGSLRLSCAGSGFTFSSYAMYWVRQAPGKGLEWVSAIDTDAG<br>TFYADSVRGRFTISRDNAKNSLYLQMNSLRAEDTAVYFCARLGEGYFFDYWGQGTL<br>VTVSS |
| 12 | VL | EIVLTQSPATLSLSPGERATLSCRASQSVSSYLAWYQQKPGQAPRLLIYDASNRAT<br>GIPARFSGSGSGTDFTLTISSLEPEDFAVYYCQQRSNWPPTFGGGTKVEIK |
| 13 | HC | EVQLVQSGGGLVQPGGSLRLSCAGSGFTFSSYAMYWVRQAPGKGLEWVSAIDTDAG<br>TFYADSVRGRFTISRDNAKNSLYLQMNSLRAEDTAVYFCARLGEGYFFDYWGQGTL<br>VTVSSASTKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKRVEPKSCDKTH<br>TCPPCPAPELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKALPAPIEKTI<br>SKAKGQPREPQVYTLPPSREEMTKNQVSLTCLVKGFYPSDIAVEWESNGQPENNYK<br>TTPPVLDSDGSFFLYSKLTVDKSRWQQGNVFSCSVMHEALHNHYTQKSLSLSPG |
| 14 | LC | EIVLTQSPATLSLSPGERATLSCRASQSVSSYLAWYQQKPGQAPRLLIYDASNRAT<br>GIPARFSGSGSGTDFTLTISSLEPEDFAVYYCQQRSNWPPTFGGGTKVEIKRTVAA<br>PSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC |

Accordingly, in some embodiments, the anti-OX40 antibody comprises the three variable heavy chain CDRs and the three variable light chain CDRs that are in the variable heavy chain and variable light chain of SEQ ID NOs: 11 and 12, respectively.

In some embodiments, the anti-OX40 antibody comprises heavy chain CDR1, CDR2, and CDR3 sequences comprising SEQ ID NOs: 5-7, respectively, and/or light chain CDR1, CDR2, and CDR3 sequences comprising SEQ ID NOs: 8-10, respectively.

In some embodiments, the anti-OX40 antibody comprises heavy chain CDR1, CDR2, and CDR3 sequences consisting of SEQ ID NOs: 5-7, respectively, and/or light chain CDR1, CDR2, and CDR3 sequences consisting of SEQ ID NOs: 8-10, respectively.

SEA-CD40), as well as antibodies that compete with and/or bind to the same epitope as these antibodies.

Preferably, the agonistic antibodies bind to the immunostimulatory receptor with high affinity, for example, with a $K_D$ of $10^{-7}$ M or less, $10^{-8}$M or less, $10^{-9}$M or less, $10^{-10}$ M or less, $10^{-11}$M or less, $10^{-12}$M or less, $10^{-12}$M to $10^{-7}$M, $10^{-11}$M to $10^{-7}$M, $10^{-10}$ M to $10^{-7}$M, or $10^{-9}$M to $10^{-7}$M.

In some embodiments, the agonistic antibodies that bind to the immunostimulatory receptor are antibodies selected from the group consisting of an IgG1, an IgG2, an IgG3, an IgG4, or a variant thereof. In a particular embodiment, the antibody is an IgG1 anti-OX40 antibody, e.g., OX40.21.

In certain embodiments, the agonistic antibodies that bind to an immunostimulatory receptor comprise a modified heavy chain constant region that alters the properties of the antibody. For instance, the agonistic antibodies may comprise a modified heavy chain constant region that alters the activity of the antibodies relative to antibodies having a non-modified heavy chain constant region. Accordingly, in some embodiments, the agonistic antibodies have modifications in the heavy chain constant region that enhance effector function. In other embodiments, the agonistic antibodies have modifications in the heavy chain constant region that reduce effector function. Modifications in the Fc region can be made to, for example, (a) increase or decrease antibody-dependent cell-mediated cytotoxicity (ADCC), (h) increase or decrease complement mediated cytotoxicity (CDC), (c) increase or decrease affinity for C1q and/or (d) increase or decrease affinity for a Fc receptor relative to the parent Fc. Specific modifications (e.g., amino acid substitution(s)) that can be made to generate variant Fc regions having these features are well known in the art, and summarized in, e.g., WO2016/196228.

In some embodiments, the agonistic antibodies that bind to the immunostimulatory receptor are human, humanized, or chimeric antibodies.

In some embodiments, the agonistic antibodies that bind to the immunostimulatory receptor are bispecific antibodies.

In some embodiments, the agonistic antibodies that bind to the immunostimulatory receptor are immunoconjugates that are conjugated to a moiety, such as a detectable label (e.g., radioisotopes, fluorescent labels, enzymes, and other suitable antibody tags) or an anti-cancer agent (e.g., antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents). In some embodiments, the immunoconjugate is an antibody-drug conjugate (ADC).

III. Compositions

Also provided herein are compositions, e.g., a pharmaceutical compositions, containing an agonistic antibody that binds to an immunostimulatory receptor (e.g., OX40), formulated together with a pharmaceutically acceptable carrier, for use in the methods described herein.

Pharmaceutical compositions described herein can be administered as monotherapy or as combination therapy, e.g., the combination therapies described herein. For example, the combination therapy can include administration of an agonistic antibody that binds to an immunostimulatory receptor combined with at least one other anti-cancer and/or T-cell stimulating (e.g., activating) agent. Examples of therapeutic agents that can be used in combination therapies are described in detail supra.

As used herein, "pharmaceutically acceptable carriers" include any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compositions described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutical compositions described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition may comprise a preservative or may be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof.

The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals. Suitable dosages of the agonistic antibodies that bind to immunostimulatory receptors (e.g., anti-OX40 antibodies) can be determined using the methods described herein.

For administration of an anti-OX40 antibody (e.g., OX40.21), the dosage ranges from about 0.0001 to 100 mg/kg, about 0.01 to 10 mg/kg, about 0.01 to 5 mg/kg, about 0.1 to 1 mg/kg, about 0.1 to 0.5 mg/kg, or about 0.5 to 0.8 mg/kg of the host body weight. For example, dosages can be 0.2 mg/kg body weight, 0.3 mg/kg body weight, 0.5 mg/kg body weight, 1 mg/kg body weight, 3 mg/kg body weight, 5 mg/kg body weight or 10 mg/kg body weight or within the range of 1-10 mg/kg. In certain embodiments, the dosage is 0.2 mg/kg. In some embodiments, the dosage is 0.25 mg/kg. In other embodiments, the dosage is 0.5 mg/kg.

In certain embodiments, for combination treatment with an anti-OX40 antibody and anti-PD-1 or anti-CTLA-4 antibody, the antibodies can be administered at a fixed dose. Accordingly, in some embodiments, the anti-OX40 antibody is administered at a fixed dose of about 25 to about 320 mg, for example, about 25 to about 160 mg, about 25 to about 80 mg, about 25 to about 40 mg, about 40 to about 320 mg, about 40 to about 160 mg, about 40 to about 80 mg, about 80 to about 320 mg, about 30 to about 160 mg, or about 160 to about 320 mg. In one embodiment, the anti-OX40 antibody is administered at a dose of 20 mg or about 20 mg. In another embodiment, the anti-OX40 antibody is administered at a dose of 40 mg or about 40 mg. In another embodiment, the anti-OX40 antibody is administered at a dose of 80 mg or about 80 mg. In another embodiment, the anti-OX40 antibody is administered at a dose of 160 mg or about 160 mg. In another embodiment, the anti-OX40 antibody is administered at a dose of 320 mg or about 320 mg. An exemplary treatment regime entails administration once per week, once every two weeks, once every three weeks, once every four weeks, once a month, once every 3 months, once every 4 months, or once every three to 6 months.

In some embodiments, the anti-PD-1 antibody is administered at a fixed dose of about 100 to 300 mg. For example, the dosage of the immuno-oncology agent can be 240 mg or about 240 mg, 360 mg or about 360 mg, or 480 mg or about 480 mg. In certain embodiments, the dose of the anti-PD1 antibody ranges from about 0.0001 to 100 mg/kg, and more usually 0.01 to 5 mg/kg, of the host body weight. For example dosages can be 0.3 mg/kg body weight or about 0.3 mg/kg body weight, 1 mg/kg body weight or about 1 mg/kg body weight, 3 mg/kg body weight or about 3 mg/kg body weight, 5 mg/kg body weight or about 5 mg/kg body weight, or 10 mg/kg body weight or about 10 mg/kg body weight, or within the range of 1-10 mg/kg. In some embodiments, the dosage of the anti-PD-1 antibody is 240 mg or about 240 mg administered once every 2 weeks (Q2W). This dosage can be adjusted proportionately (at 120 mg per week) for longer or shorter periods, e.g., 360 mg administered once every 3 weeks (Q3W) or 480 mg administered once every 4 weeks (Q4W).

In some embodiments, for combination treatment with an anti-OX40 antibody and anti-PD-1 antibody, the antibodies can be administered at a fixed dose. In one embodiment, the anti-OX40 and anti-PD-1 antibodies are administered for at least one administration cycle, wherein the cycle is a period of 12 weeks, wherein for each of the at least one cycles, at least one dose of the anti-OX40 antibody is administered at a fixed dose of about 1, 3, 10, 20, 40, 50, 80, 100, 130, 150, 180, 200, 240 or 280 mg and at least 3 doses of the anti-PD-1 antibody are administered at fixed dose of about 50, 80, 100, 120, 150, 180, 200, 240, 480, 720, or 960 mg. In one embodiment, for each of the at least one cycles, one dose of the anti-OX40 antibody is administered at a fixed dose of about 20, 40, or 80 mg and 3 doses of the anti-PD-1 antibody are administered at fixed dose of about 480 mg. In one embodiment, for each of the at least one cycles, one dose of the anti-OX40 antibody is administered at a fixed dose of about 20 mg and 3 doses of the anti-PD-1 antibody are administered at fixed dose of about 480 mg. In one embodiment, for each of the at least one cycles, one dose of the anti-OX40 antibody is administered at a fixed dose of about 40 mg and 3 doses of the anti-PD-1 antibody are administered at fixed dose of about 480. In one embodiment, for each of the at least one cycles, one dose of the anti-OX40 antibody is administered at a fixed dose of about 80 mg and 3 doses of the anti-PD-1 antibody are administered at fixed dose of about 480. In one embodiment, the anti-PD-1 antibody is administered on Days 1, 29, and 57 of each cycle. In one embodiment, the anti-OX40 antibody is administered on Day 1 of each cycle. In one embodiment, the anti-PD-1 antibody is administered on Days 1, 29, and 57 of each cycle and the anti-OX40 antibody is administered on Day 1 of each cycle. In one embodiment, 12-week administration cycle can be repeated, as necessary. In one embodiment, the administration consists of up to 9 cycles. In one embodiment, the administration consists of 1, 2, 3, 4, 5, 6, 7, 8, or 9 cycles. In one embodiment, the anti-OX40 antibody comprises heavy chain CDR1, CDR2, and CDR3 sequences comprising SEQ ID NOs: 5-7, respectively, and light chain CDR1, CDR2, and CDR3 sequences comprising SEQ ID NOs: 8-10, respectively. In one embodiment, the OX-40 antibody comprises OX40.21. In one embodiment, the anti-PD-1 antibody comprises nivolumab.

In some embodiments, the anti-CTLA-4 antibody is administered at a dose of about 0.1 mg/kg to about 10 mg/kg. For example, dosages can be 1 mg/kg or about 1 mg/kg or 3 mg/kg or about 3 mg/kg, of the host body weight.

In certain embodiments, when administered on the same day, the anti-OX40 antibody is administered before the anti-PD-1 or anti-CTLA-4 antibody. In certain embodiments, when administered on the same day, the anti-OX40 antibody is administered after the anti-PD-1 or anti-CTLA-4 antibody. In certain embodiments, when administered on the same day, the anti-OX40 antibody is administered simultaneously with the anti-PD-1 or anti-CTLA-4 antibody.

In some cases, two or more monoclonal antibodies with different binding specificities are administered simultaneously, such that the dosage of each antibody administered falls within the ranges above. In addition, the antibodies usually are administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Antibodies can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

"Therapeutically effective dosages" of the antibodies described herein preferably results in a decrease in severity of disease symptoms, an increase in frequency and duration of disease symptom-free periods, or a prevention of impairment or disability due to the disease affliction. In the context of cancer, a therapeutically effective dose preferably results in increased survival, and/or prevention of further deterioration of physical symptoms associated with cancer. Symptoms of cancer are well-known in the art and include, for example, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

A therapeutically effective dose may prevent or delay onset of cancer, such as may be desired when early or preliminary signs of the disease are present. Laboratory tests utilized in the diagnosis of cancer include chemistries, hematology, serology and radiology. Accordingly, any clinical or biochemical assay that monitors any of the foregoing may be used to determine whether a particular treatment is a therapeutically effective dose for treating cancer. One of ordinary skill in the art would be able to determine such amounts based on such factors as the subject's size, the severity of the subject's symptoms, and the particular composition or route of administration selected.

Antibodies and compositions described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, the antibody can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Antibody compositions can be administered with medical devices known in the art. For example, in one embodiment, the composition is administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use in administering the antibodies include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the agonistic antibodies that bind to immunostimulatory receptors are formulated to ensure proper distribution in vivo. For example, the blood-brain barrier (BBB) excludes many highly hydrophilic compounds. To ensure the antibodies cross the BBB (if desired, e.g., for brain cancers), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

IV. Kits and Unit Dosage Forms

Also provided herein are kits which include a pharmaceutical composition containing an agonistic antibody that binds to an immunostimulatory receptor (e.g., anti-OX40 antibody) and a pharmaceutically-acceptable carrier, in an amount determined using the methods described herein for use in, e.g., treating cancer. The kit can further contain at least one additional agent (e.g., an agent suitable for a combination therapy described herein, such as another therapeutic agent). The kits optionally also can include instructions, e.g., comprising administration schedules, to allow a practitioner (e.g., a physician, nurse, or patient) to administer the composition contained therein to administer the composition to a patient having cancer (e.g., a solid tumor). The kit also can include a syringe.

Optionally, the kits include multiple packages of the single-dose pharmaceutical compositions each containing an effective amount of the antibody for a single administration in accordance with the methods provided above. Instruments or devices necessary for administering the pharmaceutical composition(s) also may be included in the kits. For instance, a kit may provide one or more pre-filled syringes containing an amount of the antibody.

Kits typically include a label indicating the intended use of the contents of the kit. The term label includes any writing, or recorded material supplied on or with the kit, or which otherwise accompanies the kit.

EXAMPLES

Figure 30:
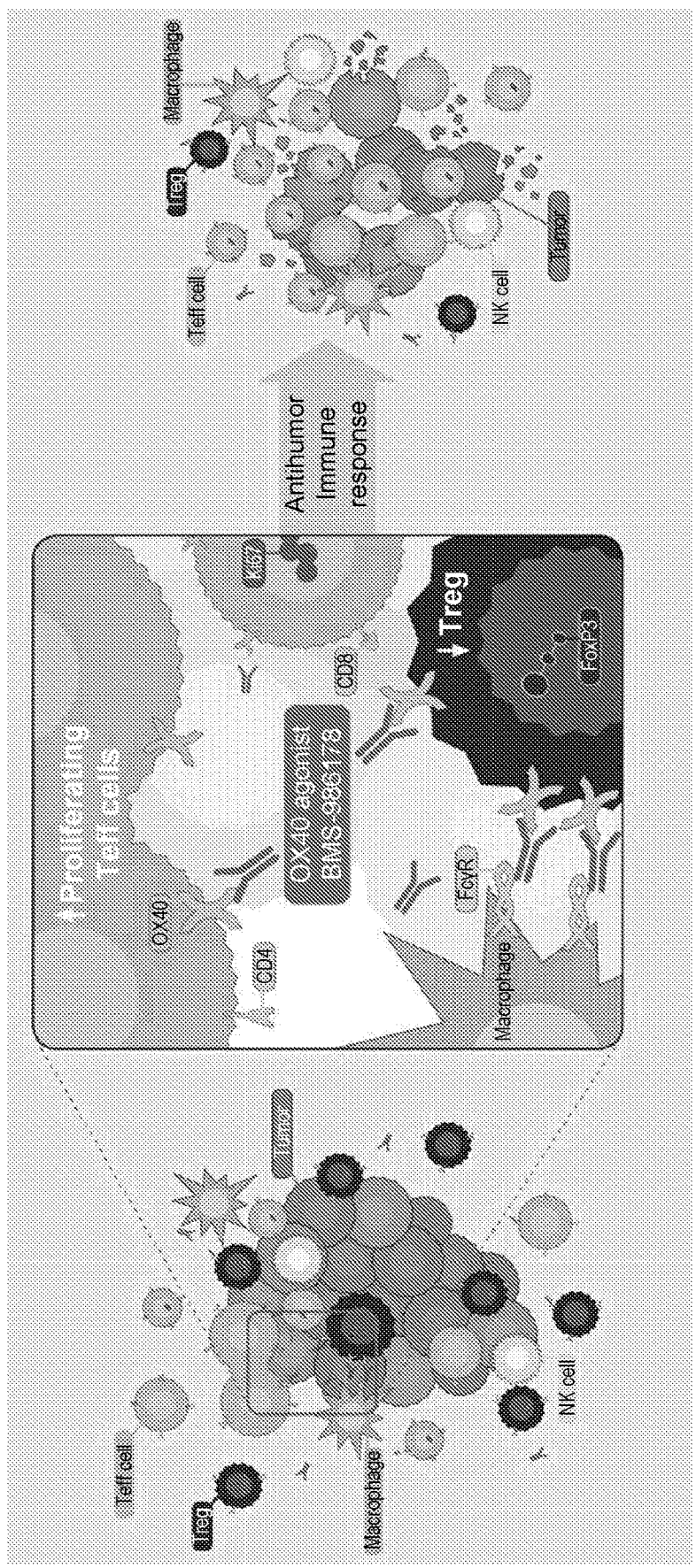
FIG. 30 demonstrates a mechanism of action of OX-40 agonist antibody (BMS-986178 surrogate mouse antibody) against OX-40. FcγR=Fcγ receptor; FoxP3=forkhead box protein P3; NK=natural killer; BMS-986178: OX40 monoclonal antibody.

OX-40 is a costimulatory receptor upregulated upon T cell activation. It increases activation, proliferation, and survival of $CD4^+$ and $CD8^+$ effector T cells (Teff) while inhibiting T cell (Treg) suppression. Described herein are examples of a fully human IgG1 agonistic monoclonal antibody that binds with high affinity to OX-40, enhancing Teff proliferation and inhibiting Treg suppression. FIG. 30 provides a depiction of the mechanism of action by the agonistic monoclonal antibody with OX-40.

Example 1: Anti-Tumor Activity of Various Doses of Ligand Blocking and Ligand Non-Blocking Anti-OX40 Antibodies This Example describes the effects of OX40.23-mIgG1 (ligand blocker agonistic antibody) and OX40.3-mIgG1 (ligand non-blocker) at various doses in the CT26 mouse tumor model.

BalbC mice were implanted with $1 \times 10^6$ CT26 cells. On day 6 post implantation, mice with established CT26 tumors (75-150 $mm^3$) were treated with OX40.23 mIgG1 or OX40.3 mIgG1 at doses of 0.03, 0.1, 0.3, 1, 3, and 10 mg/kg (Q7Dx2, d6).

Mean and median tumor growth curves per treatment group are shown in FIG. 1A (IgG control and OX40.23) and FIG. 1B (OX40.3), and mean and median tumor volumes for OX40.23-mIgG1 and OX40.3-mIgG1 treated mice are shown in FIGS. 2A-2D. Mean and median tumor volumes, TGI, and the number of tumor-free mice at the end of the study per treatment group are summarized in Table 3.

TABLE 3

Summary of Tumor Volume, TGI and Number of Tumor-Free Mice by Treatment Groups for OX40.23 and OX40.3 as Monotherapy

| Group | Treatment | Day 20 Mean TV (mm³) | Day 20 Median TV (mm³) | Day 20 Mean TGI (%) | Day 20 Median TGI (%) | Day 66 Tumor-free Mice | P value |
|---|---|---|---|---|---|---|---|
| 1 | Isotype | 2121.1 | 1787.0 | NA | NA | 0/10 | NA |
| 2 | OX40.3-mIgG1 0.03 mg/kg | 2042.9 | 1579.8 | −4 | 4 | 0/10 | 0.9997 |
| 3 | OX40.3-mIgG1 0.1 mg/kg | 1290.2 | 716.1 | 37 | 63 | 0/10 | 0.1202 |
| 4 | OX40.3-mIgG1 0.3 mg/kg | 1550.4 | 1076.0 | 30 | 54 | 1/10 | 0.5159 |
| 5 | OX40.3-mIgG1 1 mg/kg | 771.6 | 609.7 | 67 | 76 | 1/10 | 0.0010 |
| 6 | OX40.3-mIgG1 3 mg/kg | 465.2 | 216.3 | 78 | 93 | 2/10 | 0.0001 |
| 7 | OX40.3-mIgG1 10 mg/kg | 483.2 | 124.7 | 80 | 98 | 6/10 | 0.0001 |
| 8 | OX40.23-mIgG1 0.03 mg/kg | 2927.3 | 2295.0 | −40 | −8 | 0/10 | 0.1422 |
| 9 | OX40.23-mIgG1 0.1 mg/kg | 2555.2 | 1817.3 | −22 | 24 | 0/10 | 0.8167 |
| 10 | OX40.23-mIgG1 0.3 mg/kg | 1168.0 | 873.1 | 47 | 59 | 2/10 | 0.0484 |
| 11 | OX40.23-mIgG1 1 mg/kg | 279.2 | 235.9 | 89 | 91 | 1/10 | 0.0001 |
| 12 | OX40.23-mIgG1 3 mg/kg | 462.9 | 342.0 | 81 | 88 | 3/10 | 0.0001 |
| 13 | OX40.23-mIgG1 10 mg/kg | 1067.0 | 603.1 | 55 | 73 | 3/10 | 0.0205 |

Abbreviations:
TGI, tumor growth inhibition;
TV, tumor volume

OX40.3, dosed at 1 mg/kg, 3 mg/kg and 10 mg/kg, demonstrated signification tumor inhibition on day 20, resulting in 76%, 93% and 98% median TGI respectively, compared to the isotype control treated group, as well as 1/10, 2/10 and 6/10 tumor-free mice, respectively, at the end of study (Day 66). OX40.23, dose at 0.3 mg/kg, 1 mg/kg, 3 mg/kg, and 10 mg/kg, demonstrated signification tumor inhibition on day 20, resulting in 59%, 91%, 88% and 73% median TGI respectively, compared to the isotype control treated group, as well as 2/10, 1/10, 3/10 and 6/10 tumor-free mice, respectively, at the end of study (Day 66). Although all groups which received doses at 0.3 mg/kg and above of OX40.23 had reduced tumor volume, treatment at 10 mg/kg was less active compared to at 1 mg/kg and 3 mg/kg. The diminished antitumor activity at the high dose (10 mg/kg) ("hook" effect) was not observed in groups treated by OX40.3, which showed maximal TGI and the greatest number of tumor-free mice at the highest dose. Since OX40.23 but not OX40.3 blocks the OX40-OX40L interaction, these data suggested that engagement of OX40L may contribute to the attenuated antitumor efficacy by OX40.23 at high dose.

Figure 3A:
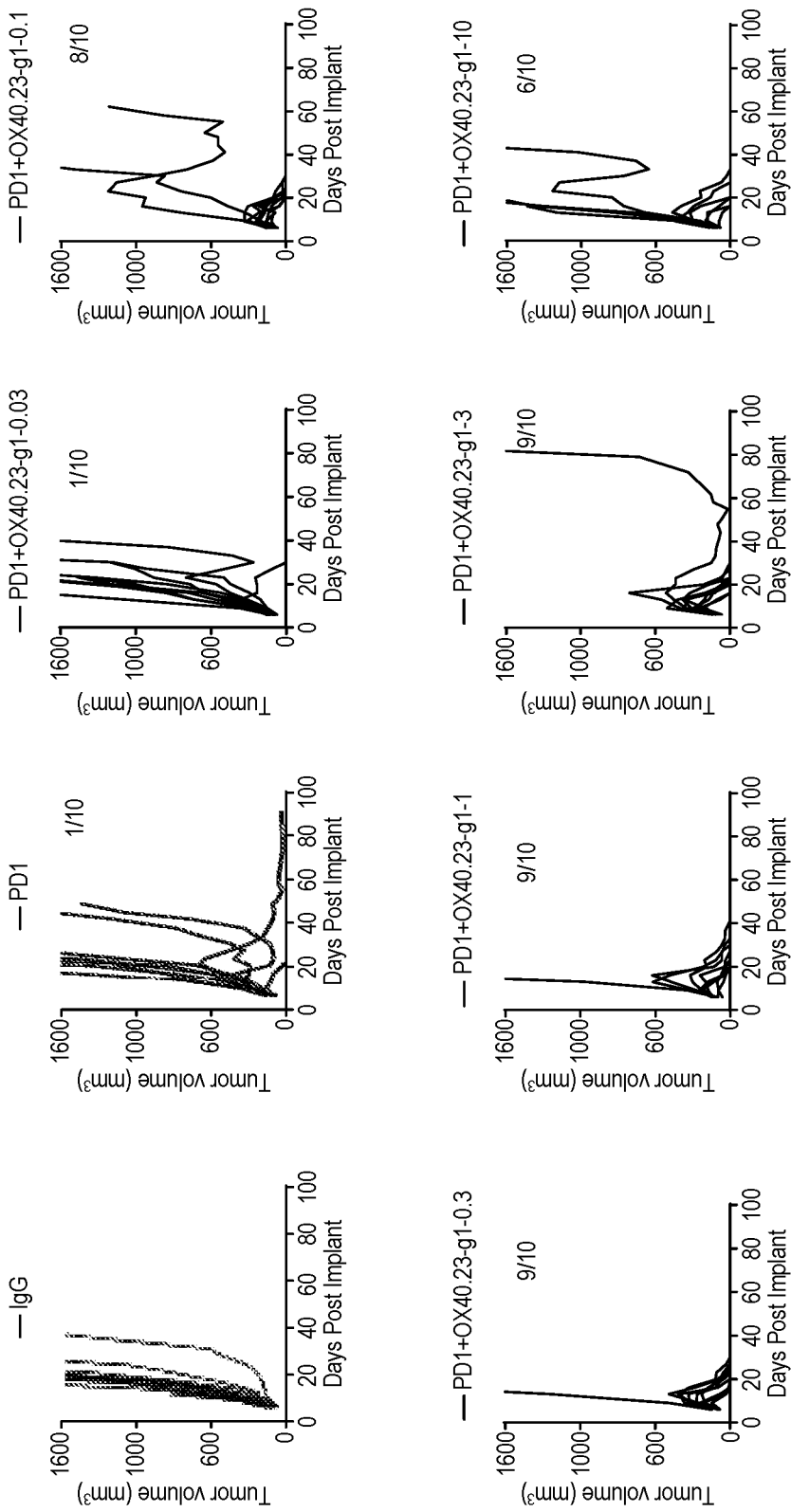
FIG. 3A is a series of tumor growth curves of a CT26 mouse tumor model treated with the combination of OX40.23+anti-PD1 antibody.
Figure 3B:
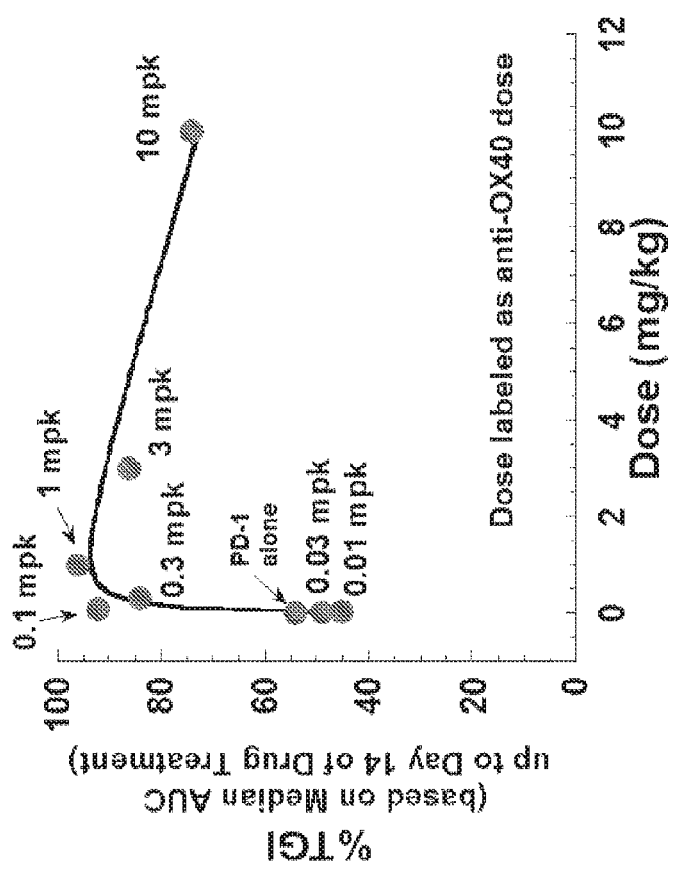
FIG. 3B is a graph showing percent tumor growth inhibition of the combination treatment at various doses of the OX40.23 antibody.
Figure 4:
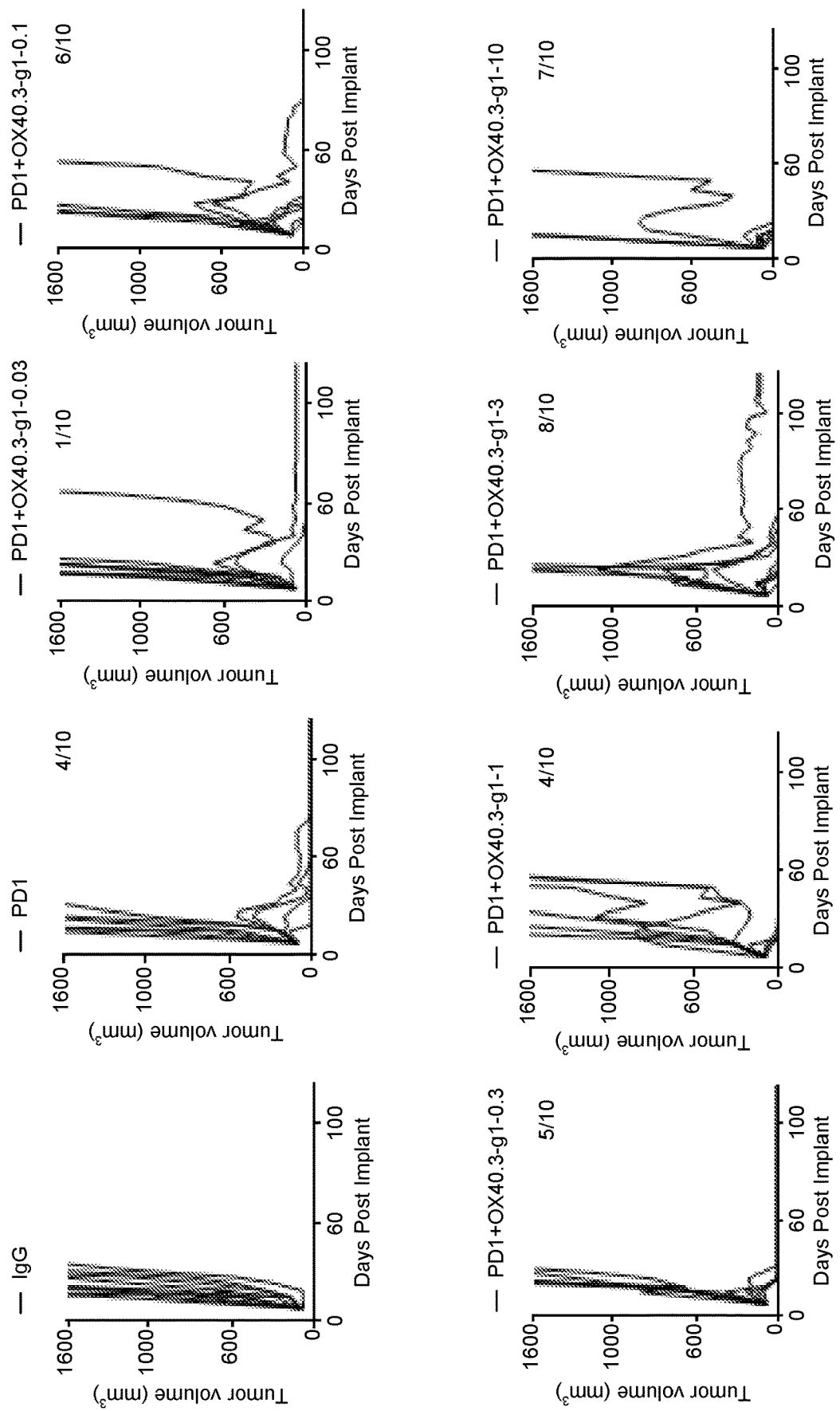
FIG. 4 is a series of tumor growth curves of a CT26 mouse tumor model treated with the combination of OX40.3+anti-PD1 antibody.

Example 2: Shift in Anti-Tumor Efficacy with Anti-OX40 Antibody+Anti-PD1 Antibody Combination Therapy This Example describes the effects of various doses of OX40.23-mIgG1 in combination with an anti-PD1 antibody. Experimental conditions were essentially the same as those described in Example 1. Individual tumor growth curves for OX40.23 (Q7D×2)+anti-PD1 antibody (IgG1 D265A; Q4D×3) treated mice are shown in FIGS. 3A and 3B, and curves for OX40.3+anti-PD1 antibody treated mice are shown in FIG. 4. Mean and median tumor volumes, TGI, and the number of tumor-free (TF) mice at the end of the study per treatment group for OX40.23+anti-PD1 treated mice are summarized in Table 4, and that for OX40.3+anti-PD1 treated mice are summarized in Table 5.

TABLE 4

Summary of tumor volume, TGI and number of tumor-free mice by treatment groups for OX40.23 in Combination with Anti-PD-1 antibody

| Group | Treatment | Day 19 Mean TV (mm³) | Day 19 Median TV (mm³) | Day 19 Mean TGI (%) | Day 19 Median TGI (%) | Day 91 Tumor-free Mice | P value |
|---|---|---|---|---|---|---|---|
| 1 | Isotype | 1639.7 | 1768.3 | NA | NA | 0/10 | NA |
| 2 | Anti-PD-1 | 809.9 | 691.5 | 55 | 65 | 1/10 | NA |
| 3 | Anti-PD-1 + OX40.23-mIgG1 0.03 mg/kg | 794.1 | 791.9 | 56 | 63 | 1/10 | 0.9999 |
| 4 | Anti-PD-1 + OX40.23-mIgG1 0.1 mg/kg | 170.1 | 47.4 | 96 | 103 | 8/10 | 0.0001 |

TABLE 4-continued

Summary of tumor volume, TGI and number of tumor-free mice by treatment groups for OX40.23 in Combination with Anti-PD-1 antibody

| Group | Treatment | Day 19 Mean TV (mm³) | Day 19 Median TV (mm³) | Day 19 Mean TGI (%) | Day 19 Median TGI (%) | Day 91 Tumor-free Mice | P value |
|---|---|---|---|---|---|---|---|
| 5 | Anti-PD-1 + OX40.23-mIgG1 0.3 mg/kg | 38.7 | 44.3 | 103 | 103 | 9/10 | 0.0001 |
| 6 | Anti-PD-1 + OX40.23-mIgG1 1 mg/kg | 62.2 | 38.3 | 102 | 103 | 9/10 | 0.0001 |
| 7 | Anti-PD-1 + OX40.23-mIgG1 3 mg/kg | 86.0 | 48.9 | 101 | 103 | 9/10 | 0.0001 |
| 8 | Anti-PD-i + OX40.23-mIgG1 10 mg/kg | 507.5 | 133.8 | 78 | 100 | 6/10 | 0.2086 |

TABLE 5

Summary of Tumor Volume, TGI and Number of Tumor-Free Mice by Treatment Groups for OX40.3 in Combination with Anti-PD-1 Antibody

| Group number | Treatment | Day 19 Mean TV (mm³) | Day 19 Median TV (mm³) | Day 19 Mean TGI (%) | Day 19 Median TGI (%) | Day 124 Tumor-free Mice | P value |
|---|---|---|---|---|---|---|---|
| 1 | Isotype | 1353.2 | 1126.5 | NA | NA | 0/10 | NA |
| 2 | Anti-PD-1 | 989.9 | 695.6 | 11 | 32 | 4/10 | NA |
| 3 | Anti-PD-1 + OX40.3-mIgG1 0.03 mg/kg | 990.1 | 964.8 | −1 | −31 | 1/10 | 0.9999 |
| 4 | Anti-PD-1 + OX40.3-mIgG1 0.1 mg/kg | 615.5 | 302.0 | 42 | 80 | 6/10 | 0.4596 |
| 5 | Anti-PD-1 + OX40.3-mIgG1 0.3 mg/kg | 826.6 | 468.8 | 16 | 64 | 5/10 | 0.9678 |
| 6 | Anti-PD-1 + OX40.3-mIgG1 1 mg/kg | 547.0 | 321.7 | 53 | 71 | 4/10 | 0.2918 |
| 7 | Anti-PD-1 + OX40.3-mIgG1 3 mg/kg | 436.5 | 226.0 | 65 | 88 | 8/10 | 0.1165 |
| 8 | Anti-PD-1 + OX40.3-mIgG1 10 mg/kg | 105.7 | 0.0 | 97 | 109 | 7/10 | 0.0046 |

As shown in Table 4, when combined with anti-PD1 antibody, OX40.23 at dosage between 0.1 mg/kg and 3 mg/kg demonstrated significant improvement of antitumor efficacy, with more than 80% tumor-free mice at the end of the study, compared to anti-PD-1 antibody monotherapy, which led to 1/10 tumor-free mice. However, at the highest dose of OX40.23 (10 mg/kg), both mean and median tumor volumes were higher than the lower dose groups, and only 6 of 10 mice were tumor-free at the end of study, suggesting reduced antitumor activity at high doses, similar to the phenomena ("hook" effect), which was observed in OX40.23 monotherapy in Example 1.

The efficacious dose of OX40.23-mIgG1 in combination with anti-PD1 antibody was 0.1-0.3 mg/kg, which is about 10 times lower than the efficacious dose of OX40.23-mIgG1 monotherapy (1-3 mg/kg).

As shown in Table 5, OX40.3, dosed at 3 mg/kg and 10 mg/kg in combination with anti-PD1 antibody, resulted in 8/10 and 7/10 TF mice at the end of study (day 124), respectively, and more potently inhibited the growth of CT26 tumors with more than 70% median TGI on day 19, compared to anti-PD1 antibody monotherapy, which led to 4/10 TF mice on day 124 and 32% median TGI on day 19. A similar fold-shift in efficacy with a lower dose when combined with anti-PD1 antibody as seen with OX40.23 was also observed with OX40.3 (FIG. 4).

Example 3: Anti-Tumor Activity with Concurrent or Sequential Dosing of Anti-OX40 and Anti-PD1 Antibodies This Example describes a comparison of concurrent versus sequential dosing of anti-OX40 and anti-PD1 antibodies on anti-tumor activity.

The mouse tumor model used in this experiment was essentially as described in Examples 1 and 2. OX40.23 was administered to mice at 0.03 mg/kg, 0.3 mg/kg, or 3 mg/kg on Day 5 and 12 after tumor implantation, followed by either concurrent anti-PD-1 administered on Day 5, 9 and 13, or delayed anti-PD-1 administered on Day 10, 14 and 18, which provided sequential treatment.

Figure 5:
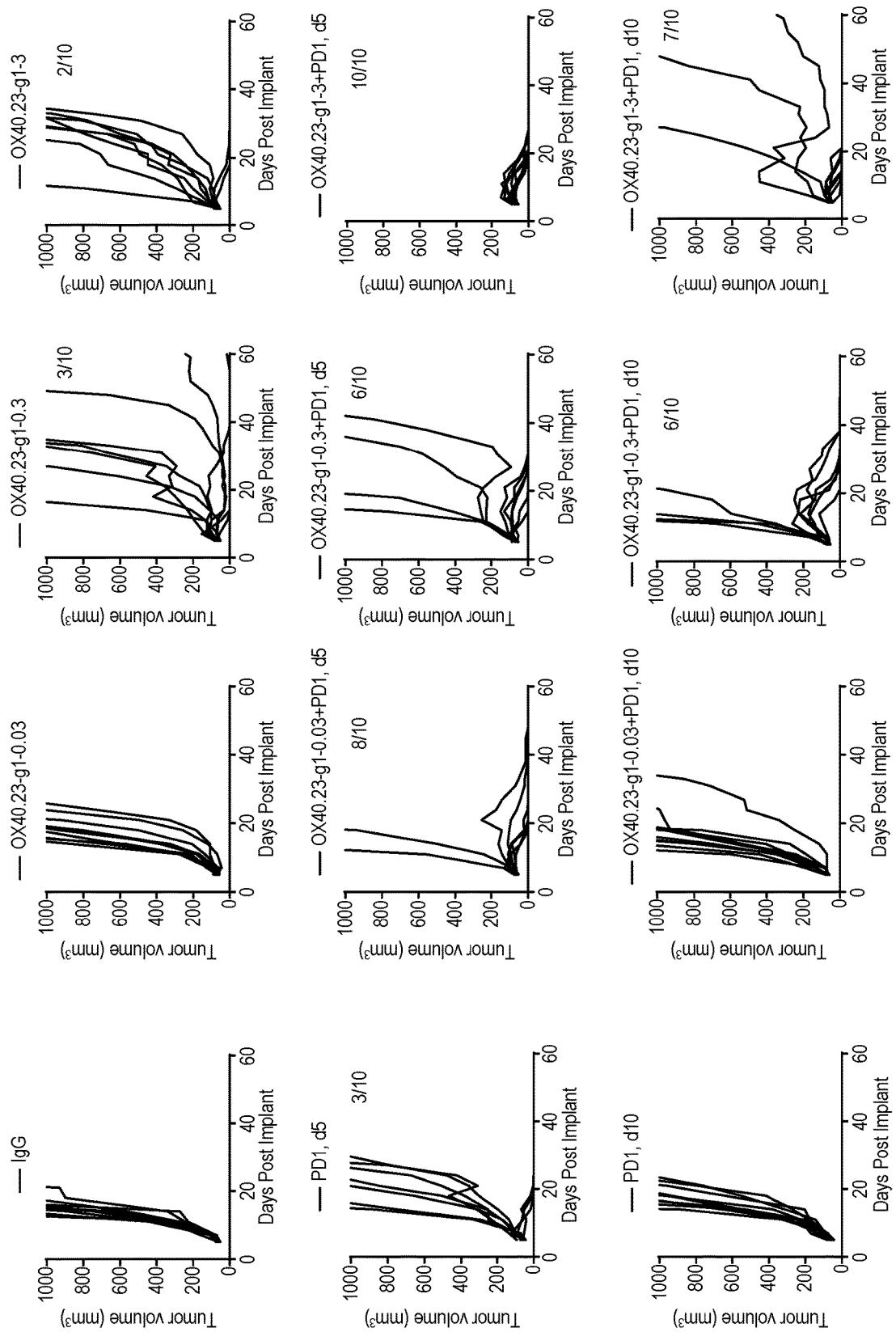
FIG. 5 is a series of tumor growth curves of a CT26 mouse tumor model treated OX40.23 on days 5 and 12 after tumor implantation at the indicated concentrations concurrently or sequentially (delayed) with an anti-PD-1 antibody. For concurrent administration, anti-PD1 antibody was administered on days 5, 9, and 13. For delayed administration, anti-PD1 antibody was administered on days 10, 14, and 18.

As shown in FIG. 5, due the fast progression of CT26 tumors, delayed anti-PD-1 antibody alone started on Day 10 showed less activity with no regression tumors, compared to the treatment that started on Day 5, which led to 3 of 10 tumor-free mice. OX40.23 plus concurrent anti-PD-1 antibody treatment resulted in significant improvements in anti-tumor activity, with 8/10, 6/10, and 10/10 tumor-free mice at 0.03 mg/kg, 0.3 mg/kg, and 3 mg/kg of OX40.23, respectively. OX40.23 plus delayed anti-PD-1 led to comparable antitumor activity as concurrent treatment, with 6/10 and 7/10 tumor-free mice at 0.3 mg/kg and 3 mg/kg of OX40.23. The combination of OX40.23 at 0.03 mg/kg with delayed anti-PD-1 treatment did not show better antitumor activity compared to the corresponding OX40.23 or anti-PD-1 monotherapy. These results suggest that concurrent dosing was similar to sequential dosing in terms of anti-tumor activity.

In addition, anti-OX40 agonist combined with anti-PD-1 or anti-CTLA-4 was tested in the same mouse tumor model used in this experiment was essentially as described in Examples 1 and 2. BMS-986178 was administered to mice either alone or concurrently with anti-PD1 or anti-CTLA.

Figure 38:
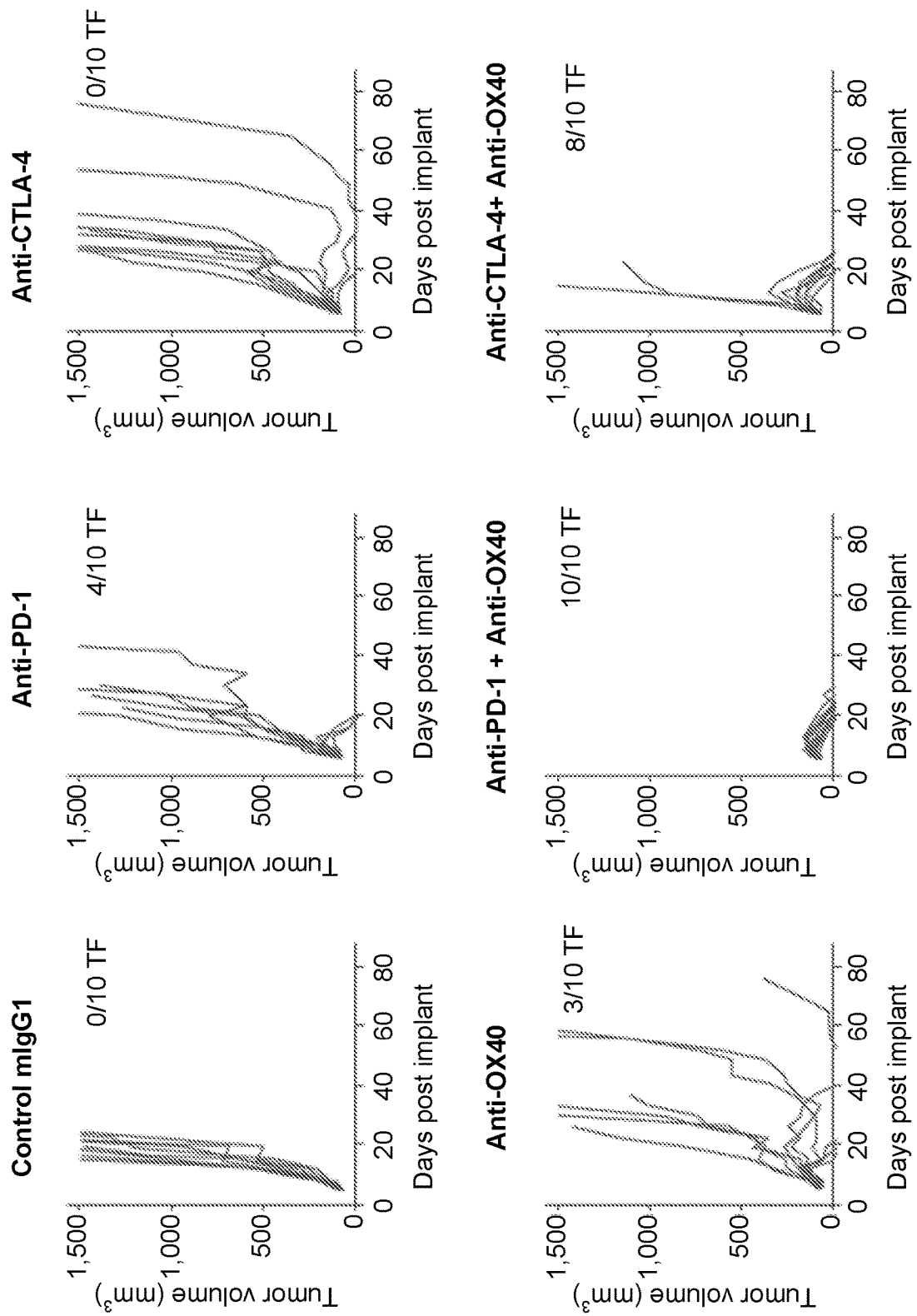
FIG. 38 shows tumor volume and number of mice that were tumor free in a CT26 mouse tumor model treated with control monoclonal antibody (mIgG1), BMS-986178 (BMS-986178 surrogate mouse antibody), anti-PD-1, anti-CTLA-4, a combination of BMS-986178 (BMS-986178 surrogate mouse antibody) and anti-PD-1 or a combination of BMS-986178 (BMS-986178 surrogate mouse antibody) and anti-CTLA-4. mIgG=mouse immunoglobulin G; TF=tumor free; anti-PD-1=4H2 mIgG1 D265A, anti-CTLA-4=9D9 mIgG2b Tumor volumes±standard deviation were measured twice weekly starting at day 6 post-implantation (start of treatment).

As shown in FIG. 38, anti-OX40 agonist combined with anti-PD-1 or anti-CTLA-4 showed enhanced antitumor activity. 10 of 10 mice treated with anti-PD-1 and BMS-986178 were tumor-free, and 8 of 10 mice treated with anti-CTLA-4 and BMS-986178 were tumor-free.

Collectively, Examples 1-3 demonstrate that maximal activity of OX40.23 (a ligand blocking agonistic antibody) was achieved at 3 mg/kg in monotherapy and at 0.3 mg/kg as combination therapy with anti-PD1 antibody. Similar fold-shifts in efficacy to lower doses were observed with the ligand non-blocking antibody OX40.3, with maximal activity achieved at 10 mg/kg in monotherapy and at 3 mg/kg as combination therapy with anti-PD1 antibody. A "hook" effect (diminished activity) was observed when OX40.23 was administered at 10 mg/kg in both monotherapy and combination therapy. However, this "hook" effect was not observed in mice treated with OX40.3 either alone or in combination with anti-PD-1 antibody, indicating that the diminished efficacy at higher doses observed with the OX40.23 was dependent on the OX40L-OX40 interaction. Furthermore, for combination treatment, concurrent dosing resulted in comparable anti-tumor activity to a staggered regimen.

Example 4: Receptor Occupancy of OX40.23 Administered as Single Agent or in Combination with Anti-PD1 Antibody To gain a better understanding of the potential mechanism(s) underlying the "hook" effect in anti-tumor efficacy observed in mice administered a high dose (10 mg/kg) of anti-OX40 antibody in monotherapy or combination therapy with anti-PD1 antibody, OX40 receptor occupancy (RO) and expression of OX40 on CD4+ T cells in the blood and tumor microenvironment were assessed.

The dosing and sampling schedule is shown in FIG. 6A. Briefly, BalbC mice were implanted with $1 \times 10^6$ CT26 cells. On day 6 post implantation, mice with established CT26 tumors (75-150 mm³) were treated with the indicated monotherapy or combination therapy at the indicated doses, with anti-PD1 antibody administered at 10 mg/kg.

Receptor occupancy in tumors and blood on Days 8 and 13 post-implantation was assessed to evaluate kinetic changes of OX40 receptor occupancy and OX40 surface expression in CD4 subsets by OX40.23 monotherapy and in combination with an anti-PD-1 antibody. Blood was obtained via cardiac puncture into syringes containing ethylenediaminetetraacetic acid (EDTA). Viable white blood cells were recovered by Histopaque®-1083 (Sigma-Aldrich) gradient separation. 2 ml of Histopaque-1083 was added into a 15 ml conical centrifuge tube, and anticoagulated whole blood was carefully layered onto the top of histopaque medium. During the centrifugation, erythrocytes and neutrophils were aggregated by polysucrose and rapidly sediment. PBMCs remained at the plasma-Histopaque 1083 interface. Most extraneous platelets were removed by low speed centrifugation during the washing steps. Tumors were removed, weighed, and processed on a gentleMACS Octo Dissociator™ (Miltenyi); a mouse tumor dissociation kit (Miltenyi) was used for tumor processing. After dissociation, cells suspension was washed, filtered and counted.

Single cell suspensions from blood and tumors of individual mice were duplicated into two plates to test occupied and total receptors separately. To test total receptors, excess OX40.23-Biotin antibody prepared in FACS buffer (2% FBS and 2 mM EDTA in PBS) was added at the final concentration of 10 µg/ml, and stained for 30 min at 4° C. Samples were then washed 3 times with FACS buffer, followed by PE-Streptavidin staining at 0.5 µg/ml for 30 min. To test occupied receptors, only PE-Streptavidin was added and stained at 0.5 µg/ml for 30 min. Both total and occupied samples were then washed three times and stained for immune cell markers using flow cytometry antibodies. DAPI at 1 µg/ml was added to distinguish live and dead cells before running flow cytometry. Antibody fluorescence was detected by flow cytometry on the Fortessa (BD Biosciences), and the results were analyzed using FlowJo software (FlowJo, LLC). Receptor occupancy was calculated for each animal according to the following equation: % RO=([ΔMFI of Test]/[ΔMFI of Total])×100 where test is the amount of receptors occupied by the OX40.23 when assessed directly ex vivo and total is the total amount of receptor present as determined from the addition of excess OX40.23-Biotin added to that sample.

As shown in FIG. 6B, receptor occupancy was antibody dose-dependent, with similar occupancies observed at higher doses in tumors and peripheral blood. Receptor occupancy profiles were similar between monotherapy and combination therapy. Moreover, compared to Day 8, OX40 receptor occupancy decreased in peripheral blood, but increased in tumors, especially at 3 mg/kg and 10 mg/kg doses on Day 13, suggesting clearance of anti-OX40 antibody in the blood and accumulation of anti-OX40 antibody in the tumor.

Figure 6C:
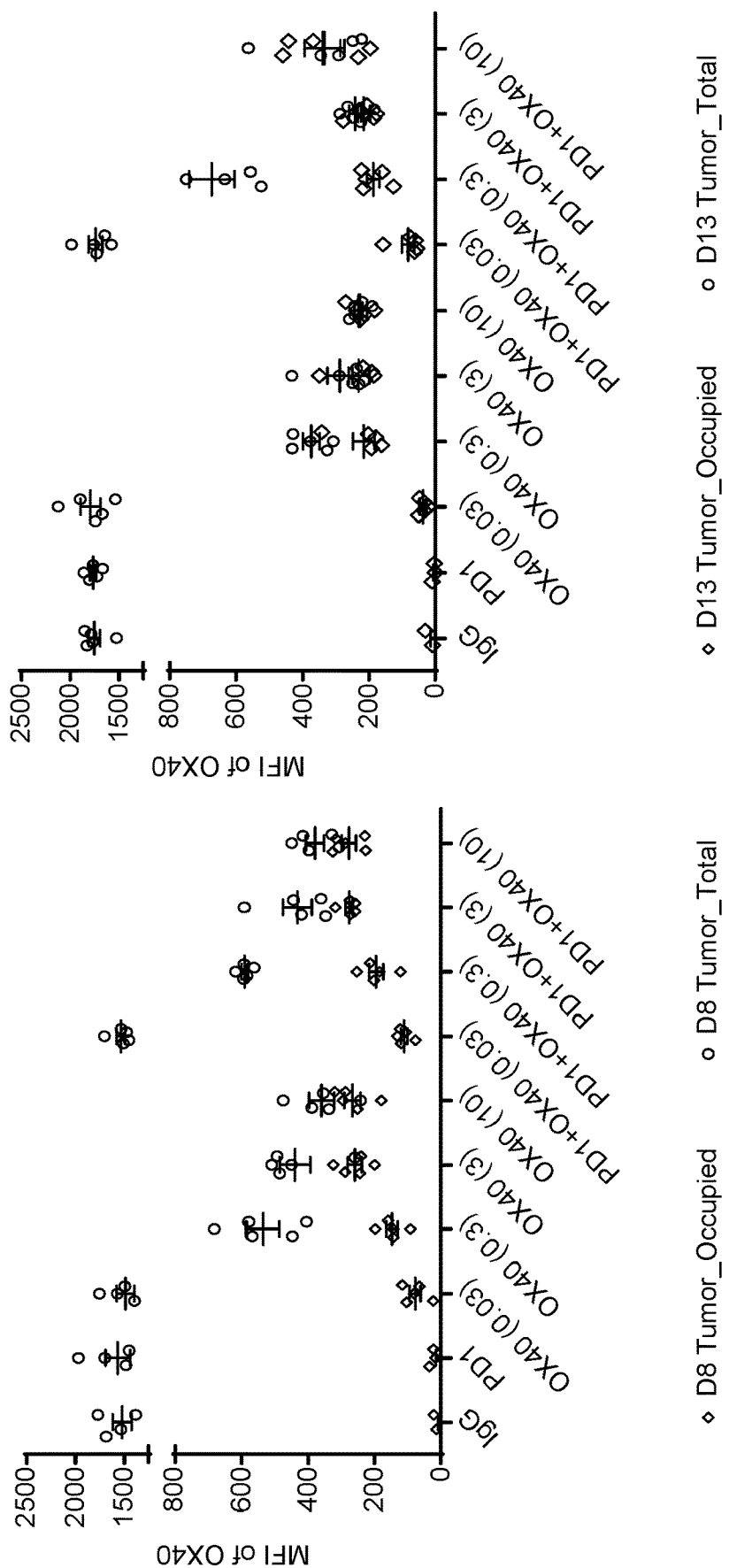
FIG. 6C shows graphs of total and occupied levels of OX40 receptor in tumors on days 8 and 13.

To further examine the regulation of the OX40 receptor occupancy, total and occupied levels of OX40 receptor were assessed independently. Across the dose escalation, the fraction of occupied OX40 receptors on cell surface continued to increase, and did not display a clear difference between day 8 and day 13 (FIG. 6C). However, the total amount of OX40 receptors present on the cell surface showed rapid downregulation at and above the 0.3 mg/kg dose (about 40% receptor occupancy at 0.3 mg/kg) at Day 8 (two days post-dose), and remained low through Day 13 of the study. These data suggest the high calculated receptor occupancy observed at the 3 mg/kg and 10 mg/kg dose of OX40.23 is likely being driven by the downregulation of total OX40 receptors, as opposed to an increase in the number of occupied receptors.

Figure 6D:
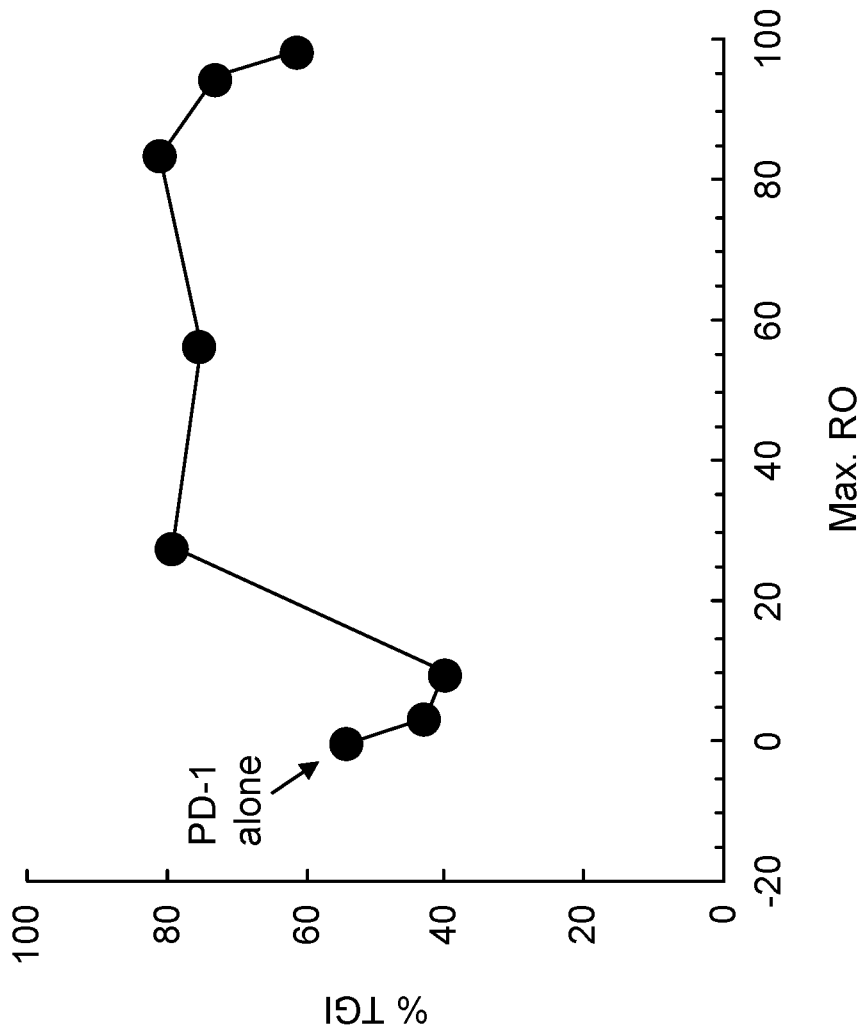
FIG. 6D is a graph showing percent tumor growth inhibition as a function of OX40 RO.

The relationship between percent tumor growth inhibition and OX40 receptor occupancy demonstrates the maximal tumor growth inhibition is achieved at between 20 and 80% receptor occupancy for the combination of OX40.23+anti- PD1, whereas a decreased tumor growth inhibition was observed when OX40 receptor occupancy exceed 80% (FIG. 6D).

In a similar experiment, CT26 tumor-bearing mice were treated with BMS-986178 or an isotype antibody IgG control. OX40 RO and total surface OX40 were assessed by flow cytometry in tumor samples at indicated timepoints after treatment.

Figure 34B:
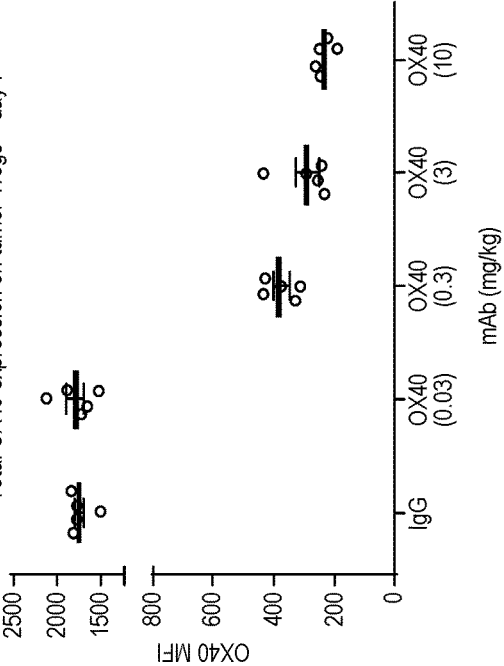
FIG. 34B is total OX40 RO expression as measured by mean fluorescence intensity on tumor Tregs 7 days after treatment with 0.03 mg/kg, 0.3 mg/kg, 3.0 mg/kg, 10 mg/kg of BMS-986178 (BMS-986178 surrogate mouse antibody) or a control IgG.
Figure 34D:
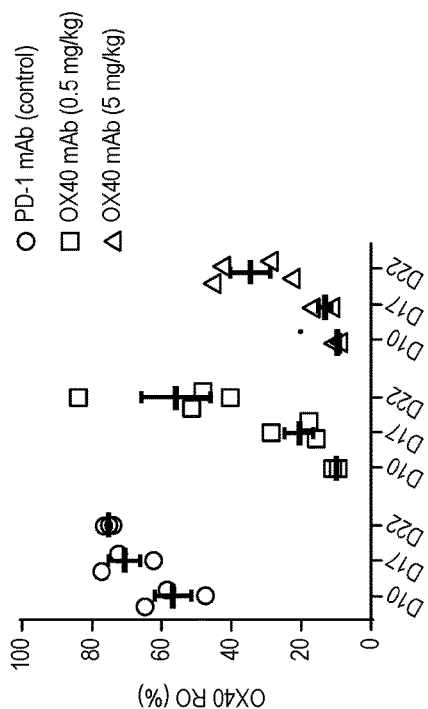
FIG. 34D is total OX40 RO expression as measured by mean fluorescence intensity on tumor Tregs at 10 days, 17 days, and 22 days after treatment with 0.5 mg/kg BMS-986178 (BMS-986178 surrogate mouse antibody), 5 mg/kg BMS-986178 (BMS-986178 surrogate mouse antibody), or control PD-1 monoclonal antibody.
Figure 34A:
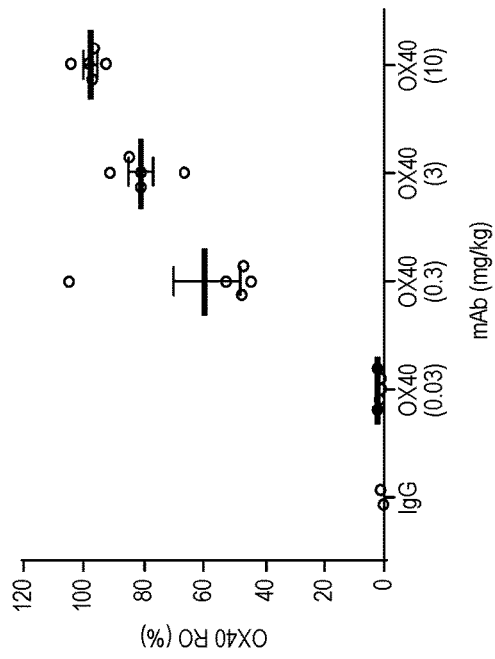
FIG. 34A is OX40 RO expression on tumor Tregs 7 days after treatment with 0.03 mg/kg, 0.3 mg/kg, 3.0 mg/kg, 10 mg/kg of BMS-986178 (BMS-986178 surrogate mouse antibody) or a control IgG.
Figure 34C:
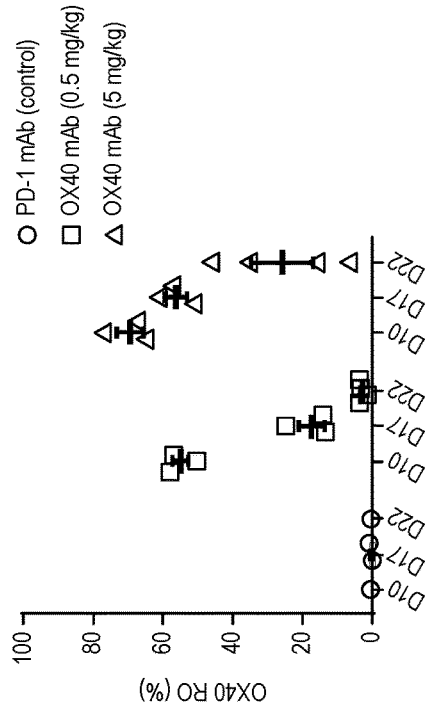
FIG. 34C is OX40 RO expression on tumor Tregs at 10 days, 17 days, and 22 days after treatment with 0.5 mg/kg BMS-986178

As shown in FIGS. 34A-34D, tumor samples from CT26 tumor-bearing mice 7 days after BMS-986178 treatment showed that OX40 RO on tumor Tregs correlated with dose of BMS-986178 (FIG. 34A), whereas the total OX40 expression on tumor Tregs decreased at doses ≥0.3 mg/kg BMS-986178 (FIG. 34B). And, as mAb-occupied OX40 decreased over time (day 10 and onward after BMS-986178treatment; FIG. 34C), OX40 surface expression was restored (FIG. 34D). Thus, OX40 expression on tumor Tregs decreased with higher doses of anti-BMS-986178 in a CT26 mouse model.

Taken together, these data demonstrate that the combination of an agonistic anti-OX40 antibody with an anti-PD1 antibody led to a significant enhancement in therapeutic efficacy over anti-PD-1 antibody monotherapy, with maximal anti-tumor activity of the combination being achieved well below 100% OX40 receptor occupancy. As receptor occupancy approached approximately 40%, a profound downregulation of surface OX40 was observed at 2 days-following antibody dosing, and was maintained through at least 7 days post-dose. This downregulation of OX40 may explain the lower therapeutic activity of the combination at the 10 mg/kg anti-OX40 dose. Thus, the proper selection of antibody dose and frequency of application is needed to minimize or prevent the diminished the anti-tumor activity at high doses of agonistic anti-OX40 antibodies (e.g., 10 mg/kg).

Example 5: Receptor Occupancy, Surface Expression of OX40, and Drug Exposure in Human Patients Administered OX40.21

This Example demonstrates the correlation between loss of surface expression of OX40 as receptor occupancy increases in human patients.

Figure 7A:
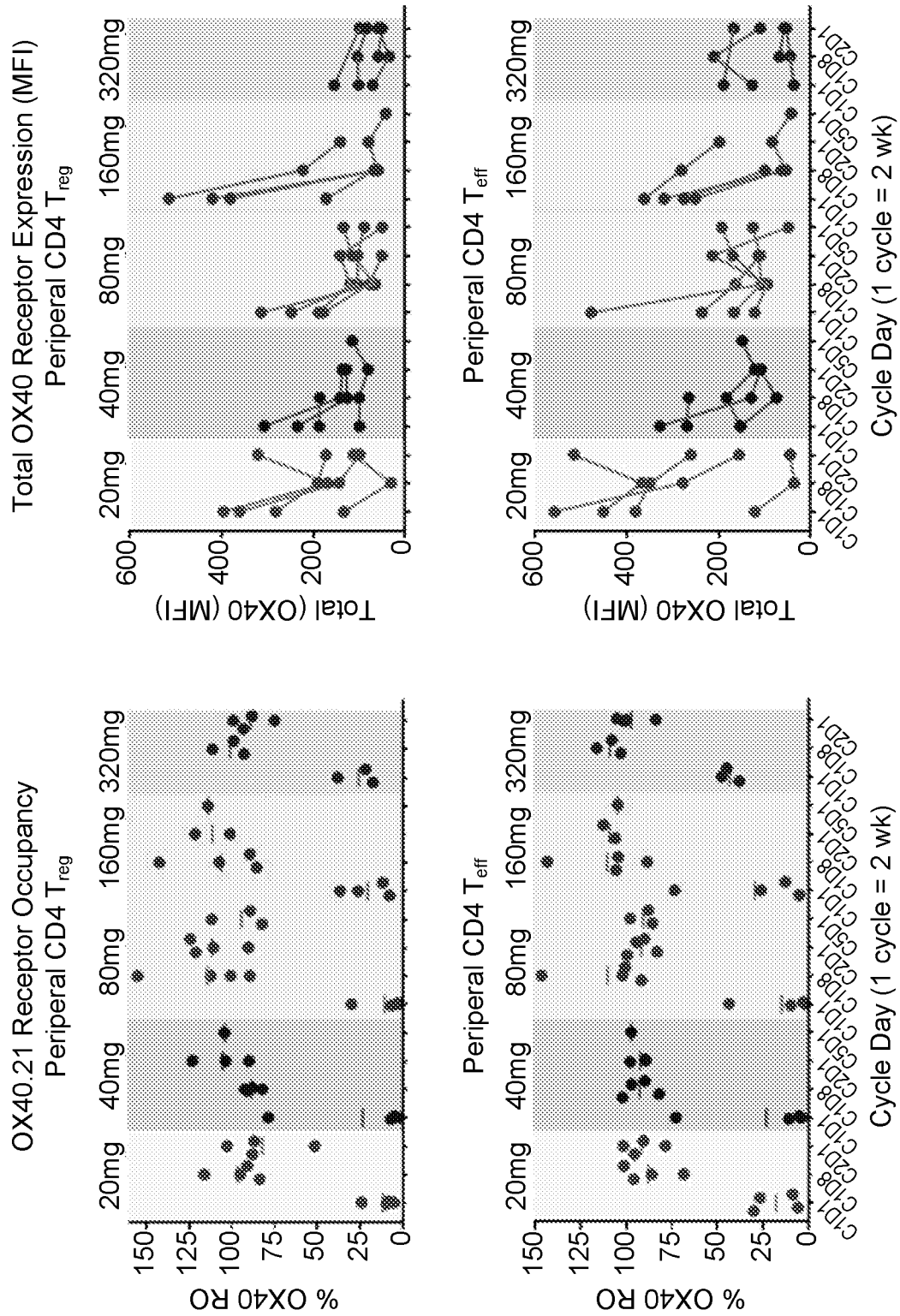
FIG. 7A is a series of graphs showing % OX40 RO in peripheral CD4+ T cells and Treg cells from human patients administered OX40.21 at 20 mg, 40 mg, 80 mg, 160 mg, and 320 mg. RO was measured on C1D1, C1D8, and C2D1 of a 2-week cycle. Observed peripheral OX40 RO in CD4+ Tregs was 80% at 20 mg and was saturated at doses ≥40 mg.

Receptor occupancy and surface OX40 expression in CD4+ T cells or Tregs were determined in human patients administered OX40.21 (an agonistic anti-OX40 antibody) at 20 mg, 40 mg, 80 mg, 160 mg, or 320 mg using the method described in Example 4 (test vs. total based equation for determining RO is the same as in Example 4, but adapted to the calculation of OX40.21 RO in human patients). Receptor occupancy was between 80 and 100% in CD4+ T cells and Tregs for each of the dose cohorts at cycle 1 day 8 and cycle 2 day 1. As shown in FIG. 7A, and consistent with the results from Example 4, surface expression of OX40 tended to decrease as receptor occupancy of OX40.21 increased in human patients. Similar receptor occupancies, as with CD4+ T cells and Tregs, were observed in peripheral blood across cohorts, with >80% receptor occupancy observed at doses >20 mg and a plateau post first dose of the second cycle (C2D1).

Figure 7B:
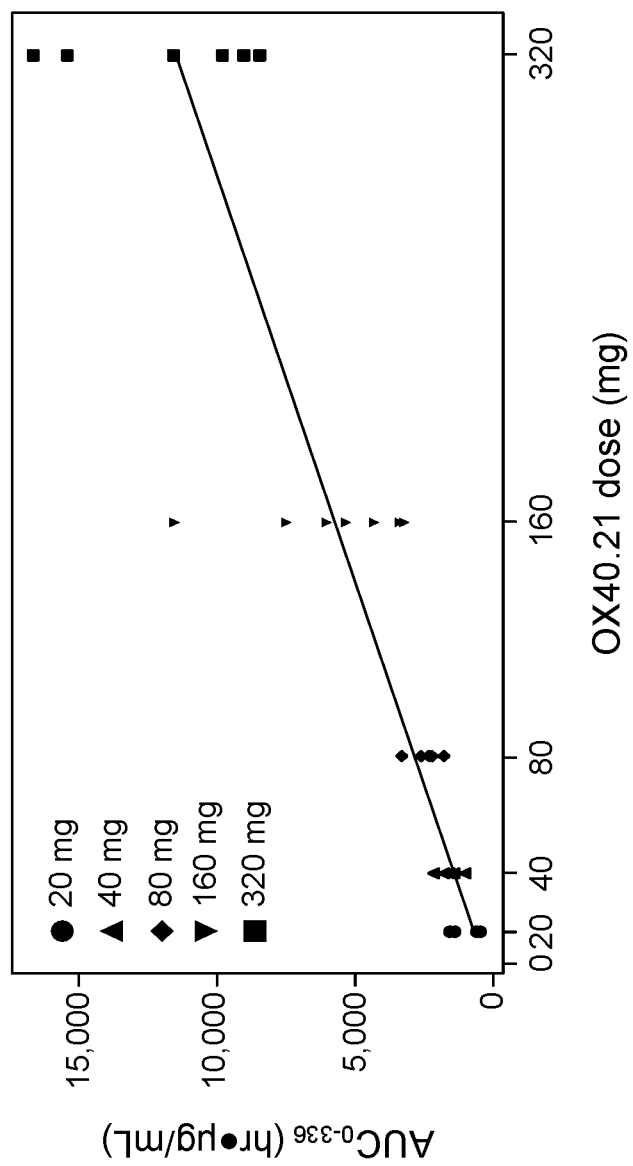
FIG. 7B is a graph showing exposure of OX40.21 in combination with nivolumab in OX40.21 doses ranging from 20 mg to 320 mg.

With respect to drug exposure, as shown in FIG. 7B, OX40.21 in combination with nivolumab showed linear PK with a dose-related increase in exposure in the 20-320 mg range.

Figures 8A, 8B:
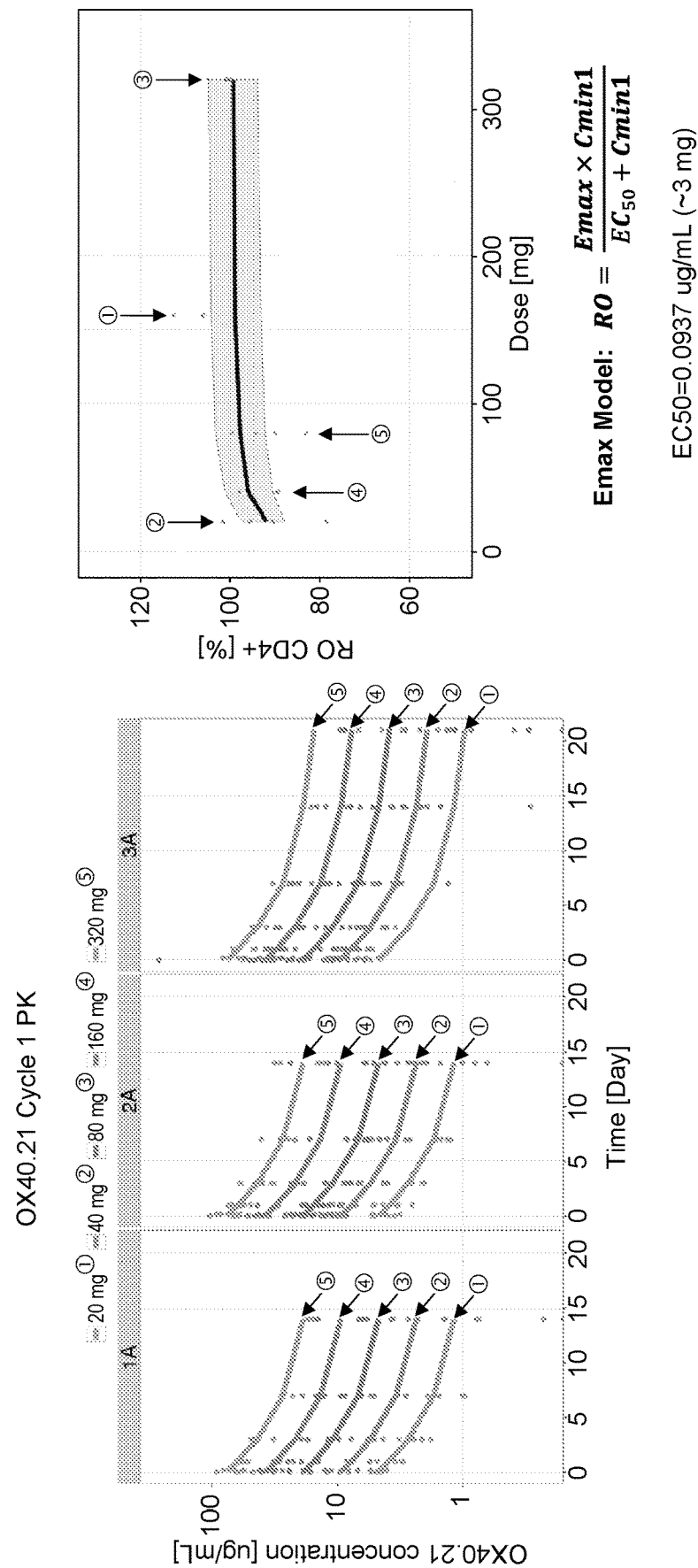
FIG. 8A is a population PK (PPK) model to describe observed OX40.21 concentration data.
FIG. 8B is a mathematical PK-PD model to describe the relationship between drug concentrations (Cmin1: trough concentration after 1st dose) and peripheral blood RO on CD4+ T cells at C2D1 from human patients treated with OX40.21, with median (line) and 95% confidence interval (shaded area) of RO.
Figure 9:
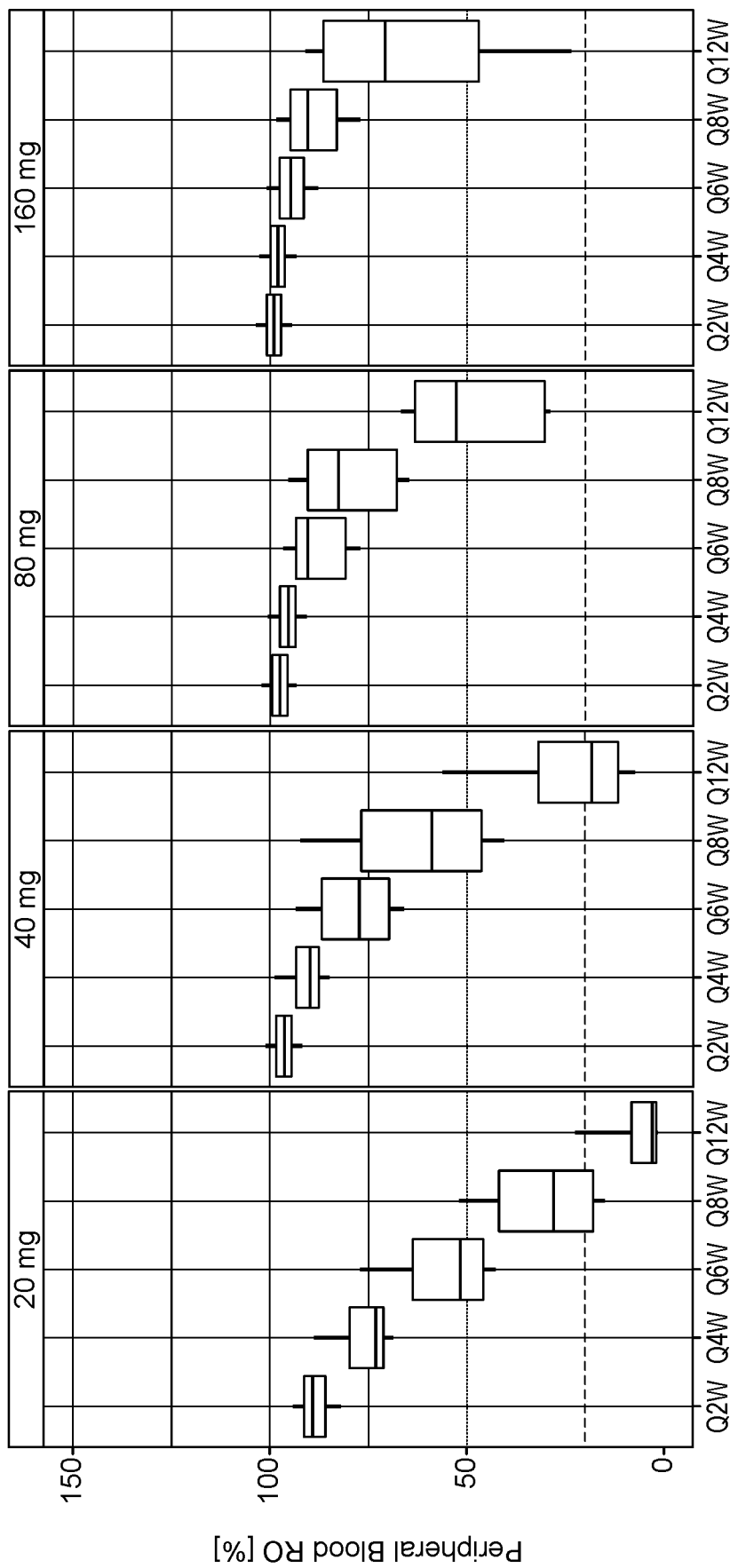
FIG. 9 shows the predicted blood RO on CD4+ T cells (median and 90% prediction interval) at various OX40.21 doses and frequencies.
Figure 40:
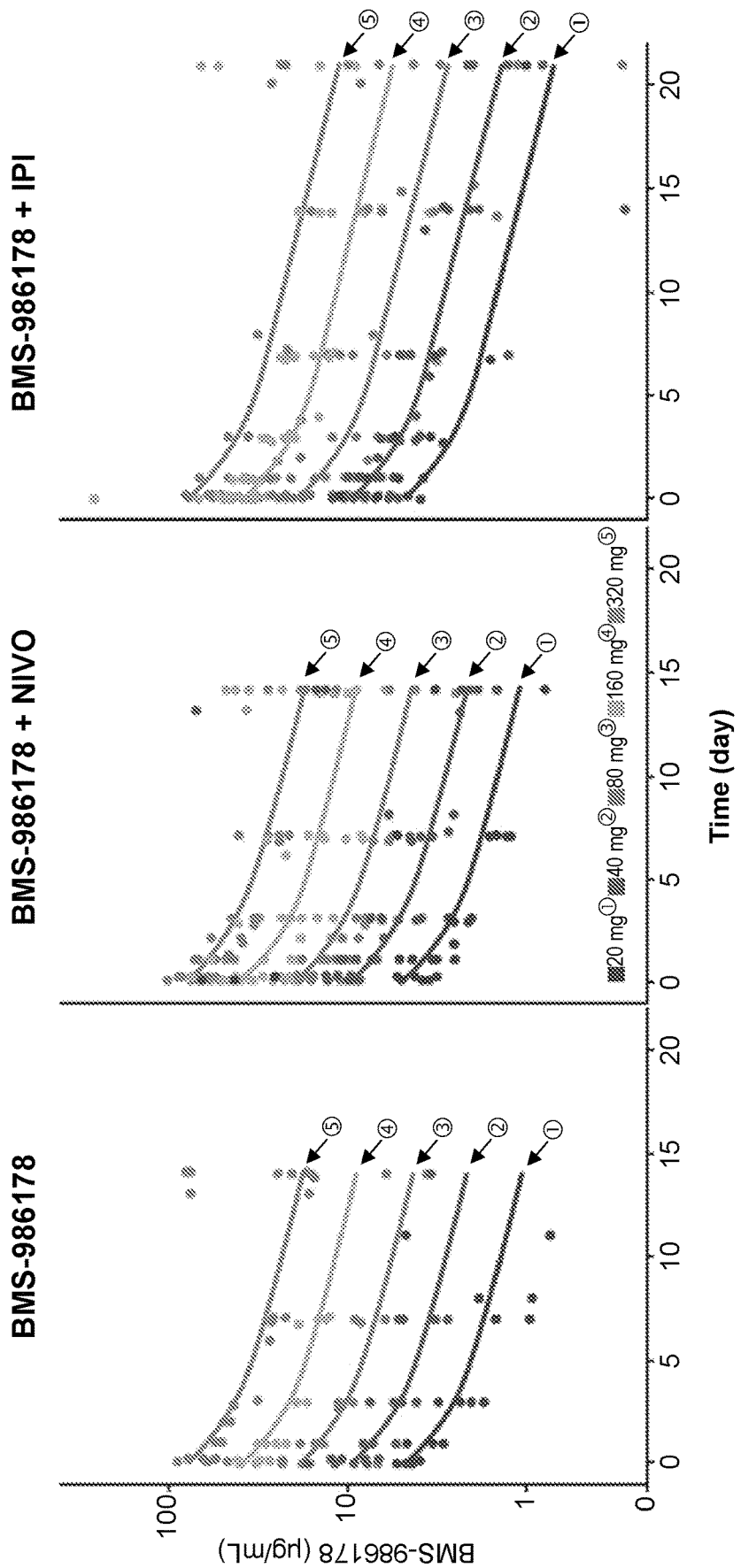
FIG. 40 shows the pharmacokinetics in BMS-986178±nivolumab or ipilimumab.

Example 6: PK-PD Model for Predicting Receptor Occupancy in Alternative Dosing Schedules This Example describes a PK-PD model for predicting receptor occupancy in human patients. The drug concentration-time profile was described by a linear two-compartment PK model using population PK analysis. As shown in FIGS. 8A and 40, the PPK model appears to provide reasonable description of observed concentration data. The individual drug exposure (Cmin1: trough concentration after first dose) in the alternative dose schedule was predicted based on the PPK model, which was used in subsequent PK-PD model development. An Emax model (equation provided below) was used to describe the relationship between drug concentrations (Cmin1: trough concentration after first dose) and blood RO at C2D1, based on RO data from 16 cancer patients administered OX40.21 at a dose range of 20-320 mg.

$$RO = \frac{RO_{max} \times \text{Drug Concentration}}{EC_{50} + \text{Drug Concentration}}$$

wherein drug concentration is Cmin1, the trough concentration after first dose, $RO_{max}$ is the maximum percentage of blood RO and $EC_{50}$ is the drug concentration corresponding to 50% of $RO_{max}$. From this analysis, the drug $EC_{50}$ was estimated to be 0.094 µg/mL (FIG. 8B). The trial stimulation was conducted to predict blood RO at alternative dosing schedules by using the established PK-PD relationship (Emax model), as well as taking into account inter-subject variability of PK and PD (FIG. 9).

Tumor RO was also predicted (FIGS. 10A and 10B) based on data generated from human tumor biopsy samples (N=5) across different cancer types (head and neck, cervical, urothelial, and colorectal cancer), where the total drug and total OX40 concentrations in tumor homogenates were measured at OX40.21 doses of 20-320 mg. The following assumptions were made to predict tumor RO at various doses and dosing regimens: 1) tumor RO EC50 is the same as that in serum; 2) tumor drug levels are at equilibrium with that in serum; 3) the mean observed tumor-to-serum concentration ratio is 0.20 (range=0.07-0.47); and 4) the mean observed OX40 level is 0.15 nM (range=0.02-0.47 nM). The predicted tumor RO (FIG. 10A) was consistent with blood RO under the scenario used. However, tumor RO deviated from blood RO when a high OX40 level of 0.47 nM, and a low tumor drug penetration ratio of 0.07, was used for tumor RO prediction (FIG. 10B).

Model-based simulations showed that the exposure generated from OX40.21 doses of 40 mg q4w, 40 mg q8w, 40 mg q12w, and 80 mg q12w may result in wide range of receptor occupancy in both blood (e.g., RO of about 20% to about 90%, FIG. 9) and tumor (e.g., RO of about 10% to about 90%, under a mean target level of 0.15 nM and mean tumor penetration ratio of 0.20, FIGS. 10A and 10B), therefore providing an opportunity to understand whether equivalent or superior PD responses may be achieved with less frequent dosing.

Example 7: In Vitro Assessment of Relationship Between OX40.21 Concentration and Receptor Occupancy This Example describes the assessment of receptor occupancy based on differing concentrations of OX40.21 in vitro in T cells.

Briefly, total T cells were purified from human whole blood using Ficoll gradient centrifugation. CD4+ T cells were isolated from PBMCs using the Miltenyi CD4+ isolation kit. Isolated T cells were cultured in the presence of irradiated CHO-OKT3-CD32A (artificial antigen presenting cells) and in the presence of serial dilutions of OX40.21 or isotype control. Receptor occupancy was determined as the ratio of bound OX40 antibody to total surface OX40 using flow cytometry. Bound antibody was assessed by adding fluorescent conjugated anti-human Fc after washing the T cells. Total OX40 was determined by adding a saturating amount of OX40 antibody to the T cells. Following incubation, cells were washed and stained by adding fluorescent conjugated anti-human FC.

Figure 11A:
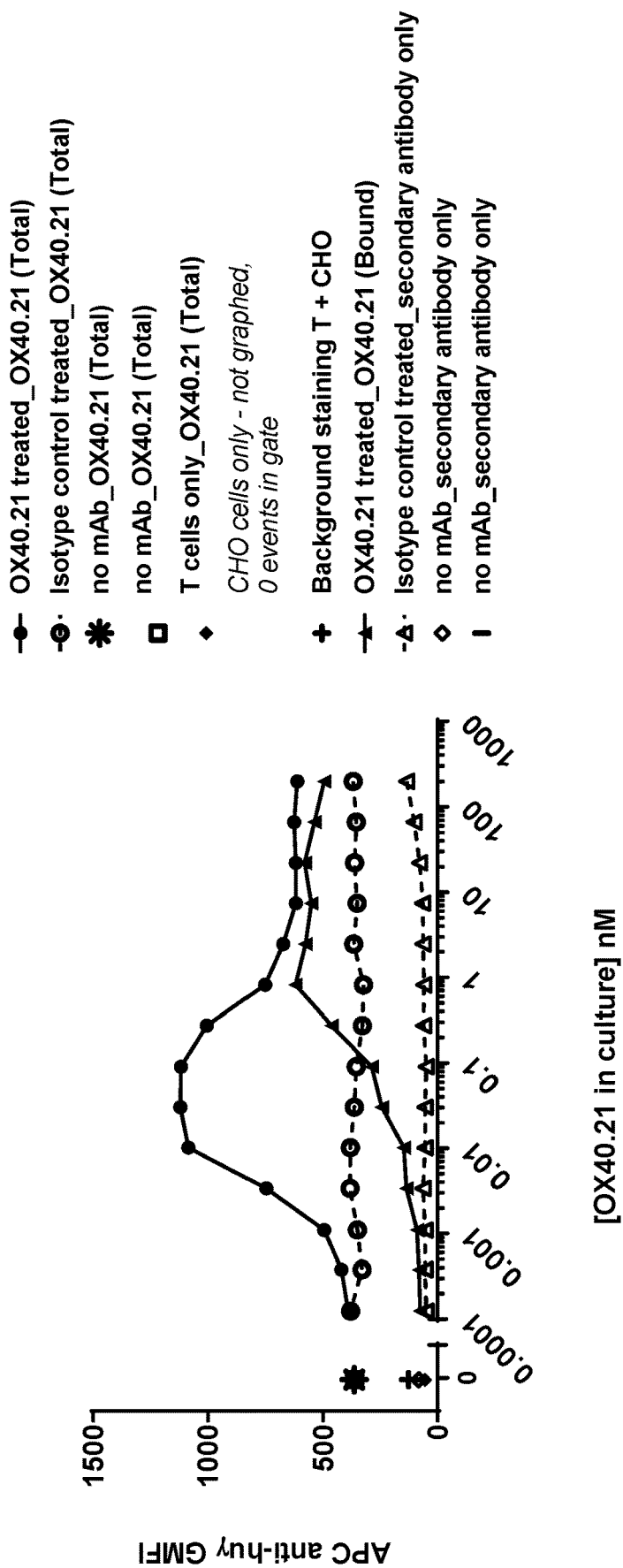
FIG. 11A is a graph showing the effects of different concentrations of OX40.21 on receptor occupancy (OX40.21 (bound)) on surface expression of OX40 (OX40.21 (total)).
Figure 11B:
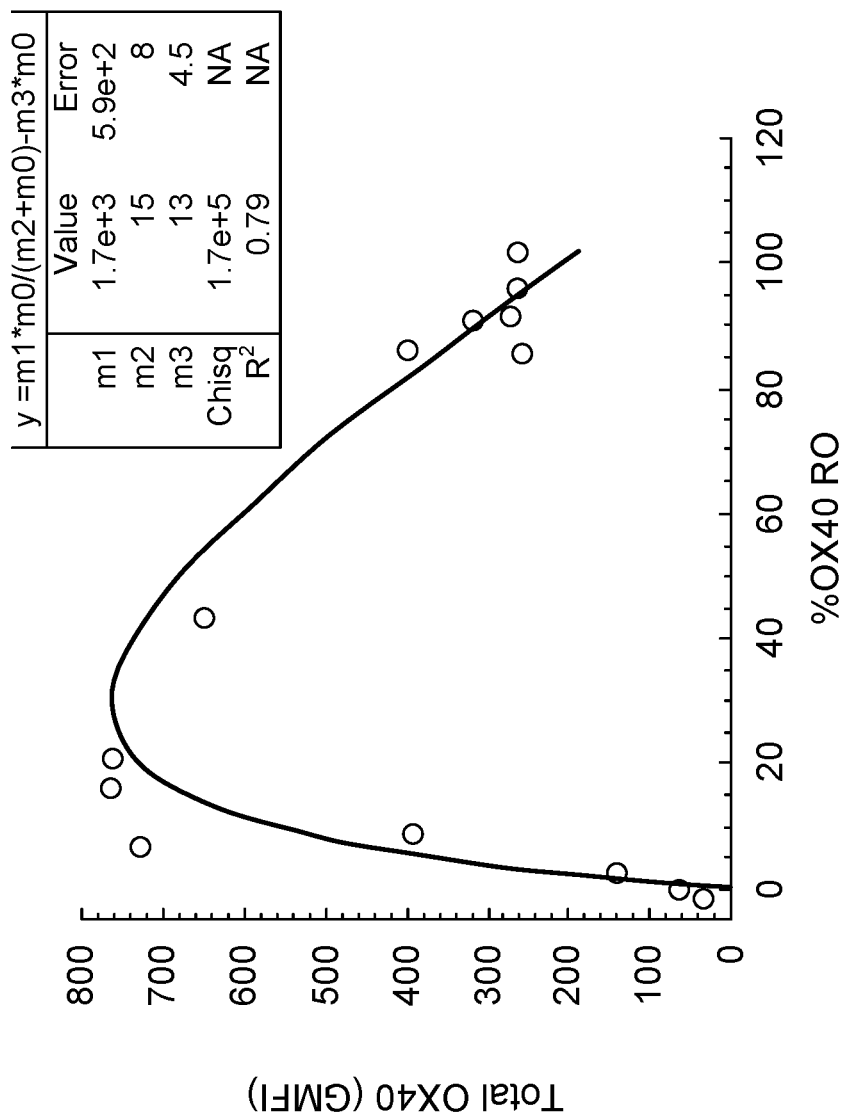
FIG. 11B is a graph summarizing the impact of % OX40 RO on total surface expression of OX40.
Figure 12B:
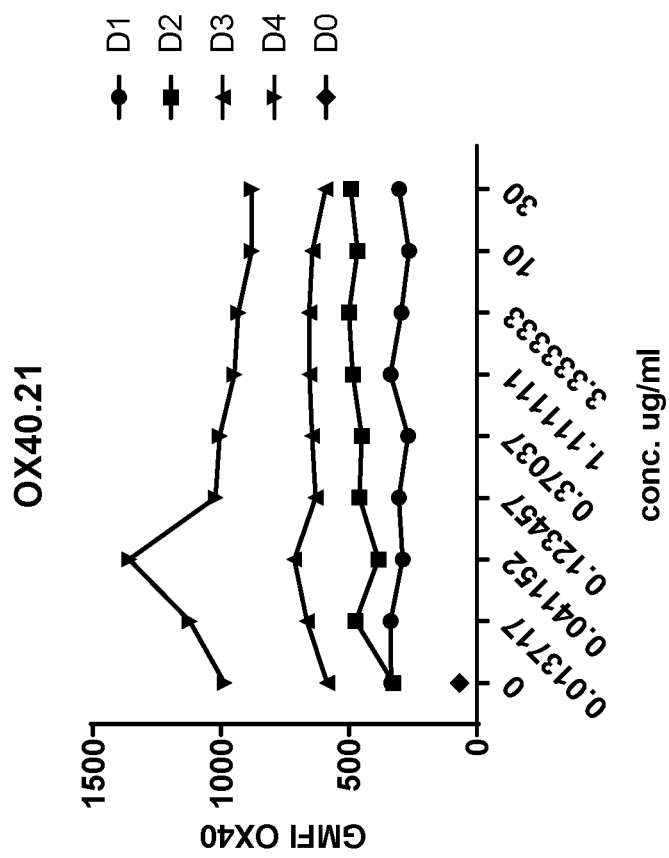
FIGS. 12A and 12B are graphs showing a time course of OX40 surface expression on various days (days 1, 2, 3, and 4) at the indicated concentrations of the isotype and OX40.21 antibodies, respectively.
Figure 12A:
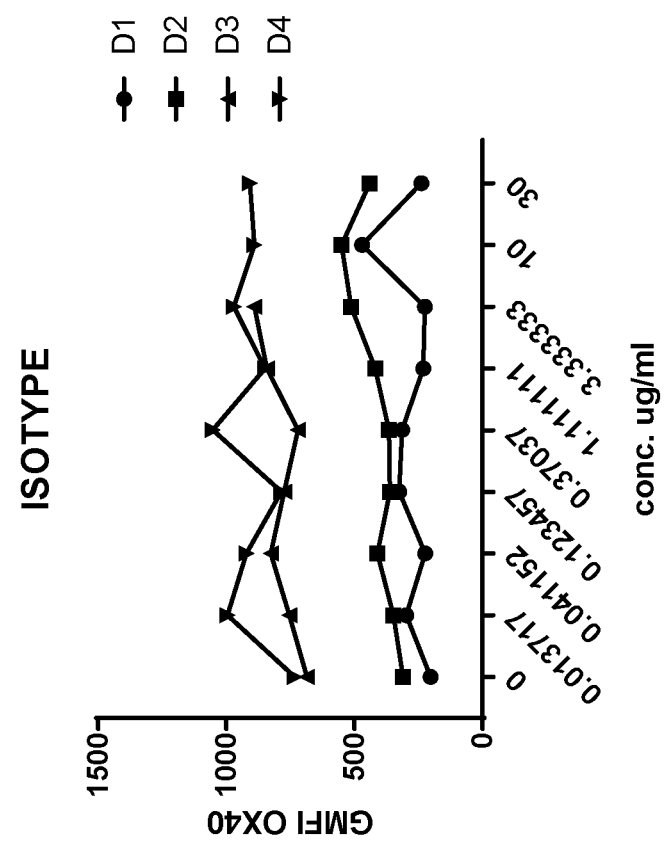
Figure 13B:
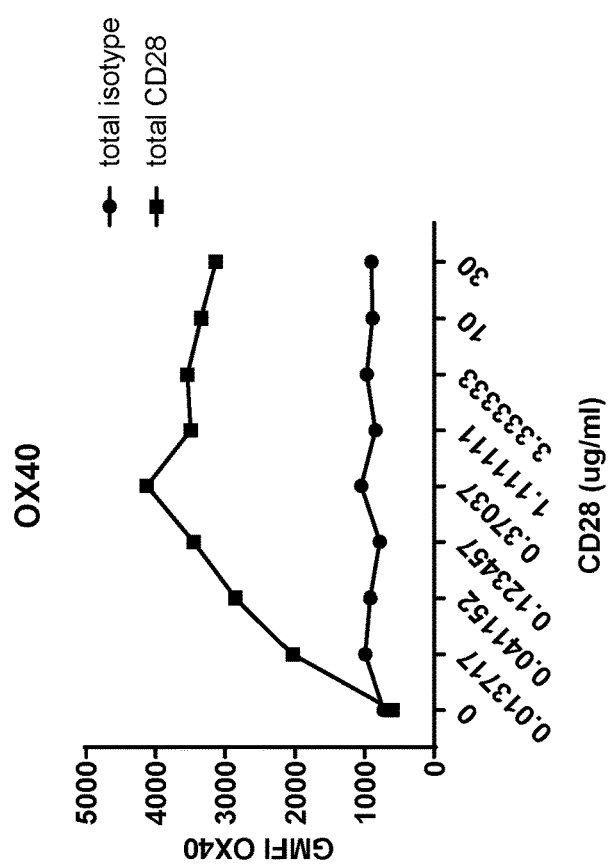
FIGS. 13A and 13B are graphs showing the effects of OX40.21 (FIG. 13A) or CD28 (FIG. 13B) concentration on total surface OX40 expression.
Figure 13A:
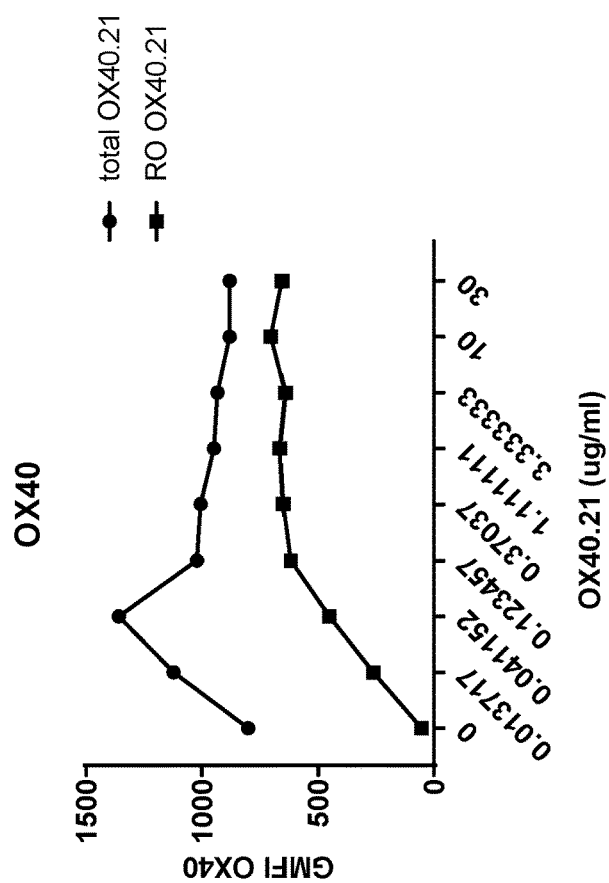

As shown in FIGS. 11A and 11B, complete receptor occupancy correlated with the downregulation of total surface OX40 (at >1 nM of OX40.21), reflecting the "hook" effect. Increasing concentrations of OX40.21 also induced OX40 on the surface of CD4+ T cells, with higher concentrations downregulating OX40. A time course of OX40 surface expression showed that the "hook" effect induced by OX40.21 correlated with the highest levels of OX40 expression on day 4 (FIG. 12A (isotype control) and FIG. 12B (OX40.21)).

To determine whether the effect was specific to OX40.21, the effect of CD28 antibody on the levels of surface OX40 was also assessed. Briefly, total T cells were purified from human whole blood using Ficoll gradient centrifugation. CD4 T cells were isolated from PBMC using Miltenyi CD4+ isolation kit. Isolated T cells were cultured in presence of irradiated CHO-OKT3-CD32A (artificial antigen presenting cells) and in presence of a serial dilution of agonistic anti-OX40 antibody, isotype control, or anti-CD28 antibody (clone CD28.2). Receptor occupancy was determined by total surface OX40 to the bound OX40 antibody by flow cytometry. Bound antibody was assessed by adding fluorescent conjugated anti-human Fc after washing the T cells. Total OX40 was determined by adding saturating amount of anti-OX40 antibody to the T cells. Following incubation, cells were washed and stained by adding fluorescent conjugated anti-human FC.

As shown in FIGS. 13A, 13B, 32A, and 32B, the effect of OX40.21 on total surface OX40 expression was specific to OX40.21, since co-stimulation of T cells with an anti-CD28 antibody induces high levels of OX40 expression which is not lost at higher concentrations. Here, monoclonal antibodies against CD137 (FIGS. 13A and 32A) and CD28 (FIGS. 13B and 32B) demonstrated no downregulation of total surface OX40 associated with the "hook" effect. Here, no loss in OX40 surface expression was observed when CD4+ T cells were treated with other costimulatory agonist antibodies.

A further experiment was performed to assess interferon-gamma (IFN-γ) secretion (a readout for T cell activation) and its relationship with receptor occupancy. Experimental conditions were the same as described above, except that, following culturing of cells for 4 days, supernatant were collected. The secretion of IFN-γ was quantified using a standard ELISA (BD Biosciences) or homogeneous time resolved fluorescence (HTRF) (Cisbios).

Figure 14:
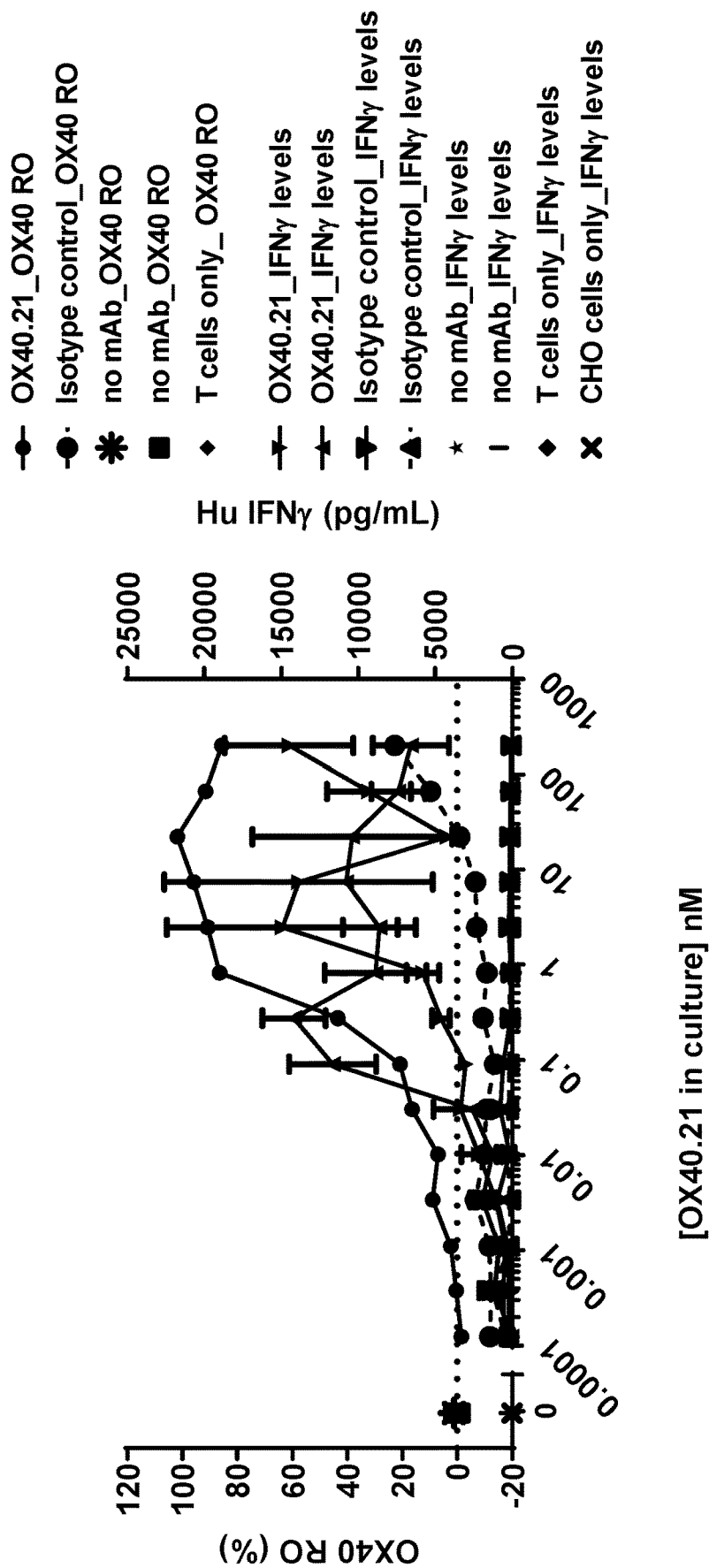
FIG. 14 is a graph showing the activation of T cells, as reflected by IFN-γ levels, as a function of OX40 RO (y-axis), and OX40.21 concentration (x-axis).

As shown in FIG. 14, OX40.21 induced T cell activation, as reflected by secretion of IFN-γ. Maximal IFN-γ was obtained at a receptor occupancy of about 20%. Consistent with the "hook" effect, IFN-γ secretion was reduced at 100% receptor occupancy.

The relationship between T cell proliferation and receptor occupancy was also assessed. Experimental conditions were the same as described above, except that, following culture of cells for 4 days, cell proliferation was tested by adding 3[H]-thymidine incorporation to the cells for 16 hours and scintillation was counted.

Figure 15A:
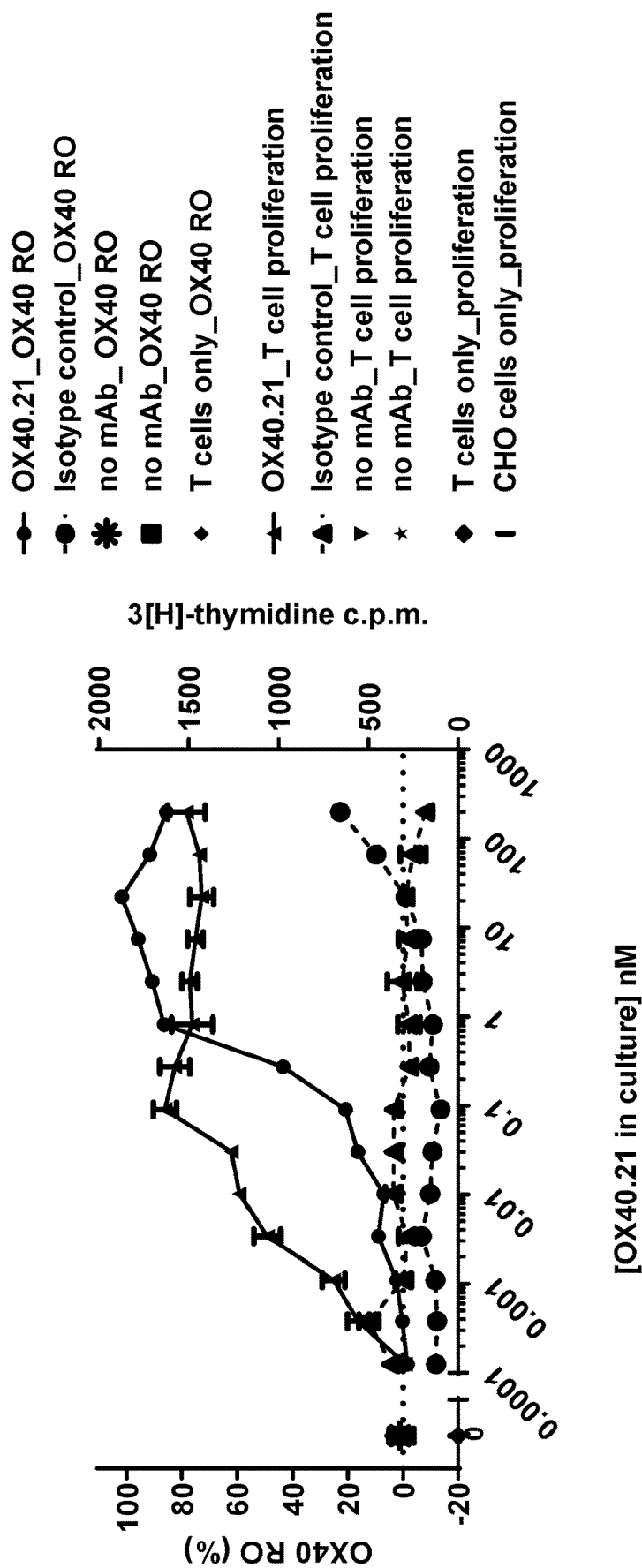
FIG. 15A is a graph showing the proliferation of T cells, as reflected by 3 [H]-thymidine incorporation, as a function of OX40 RO (y-axis), and OX40.21 concentration (x-axis).
Figure 15C:
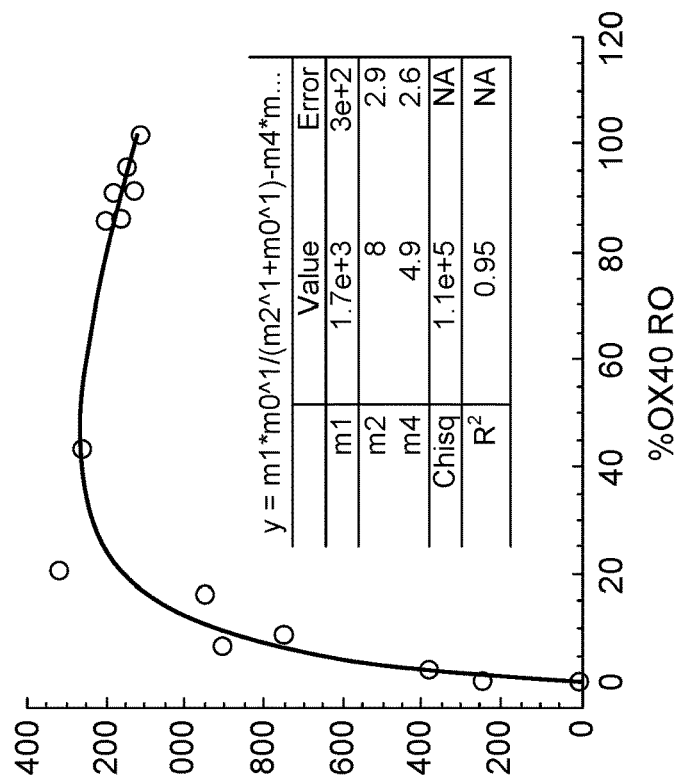
FIGS. 15B and 15C are graphs showing the number of CD25+ T cells and proliferating T cells as a measure of % OX40 RO, respectively.
Figure 15B:
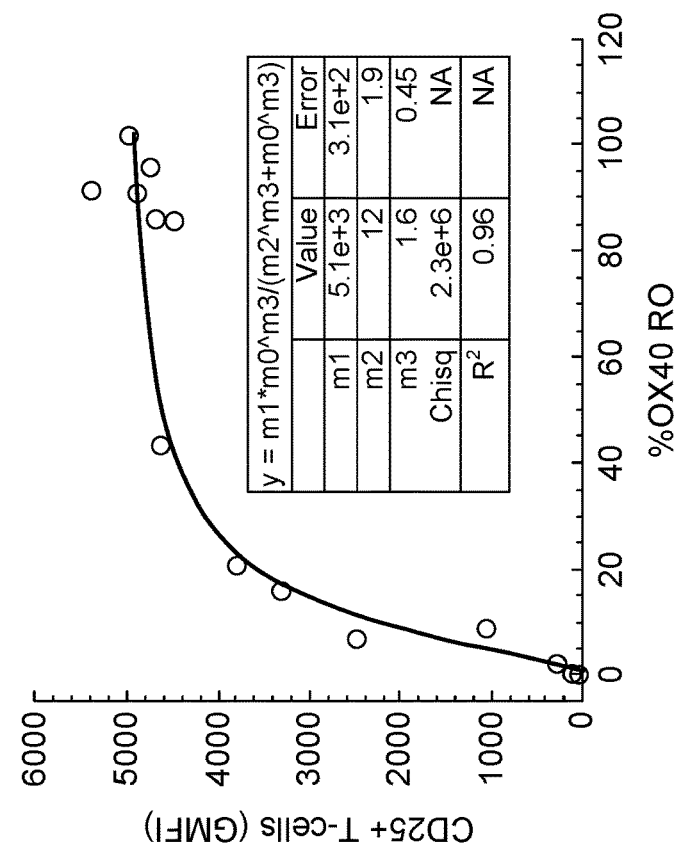
Figure 31:
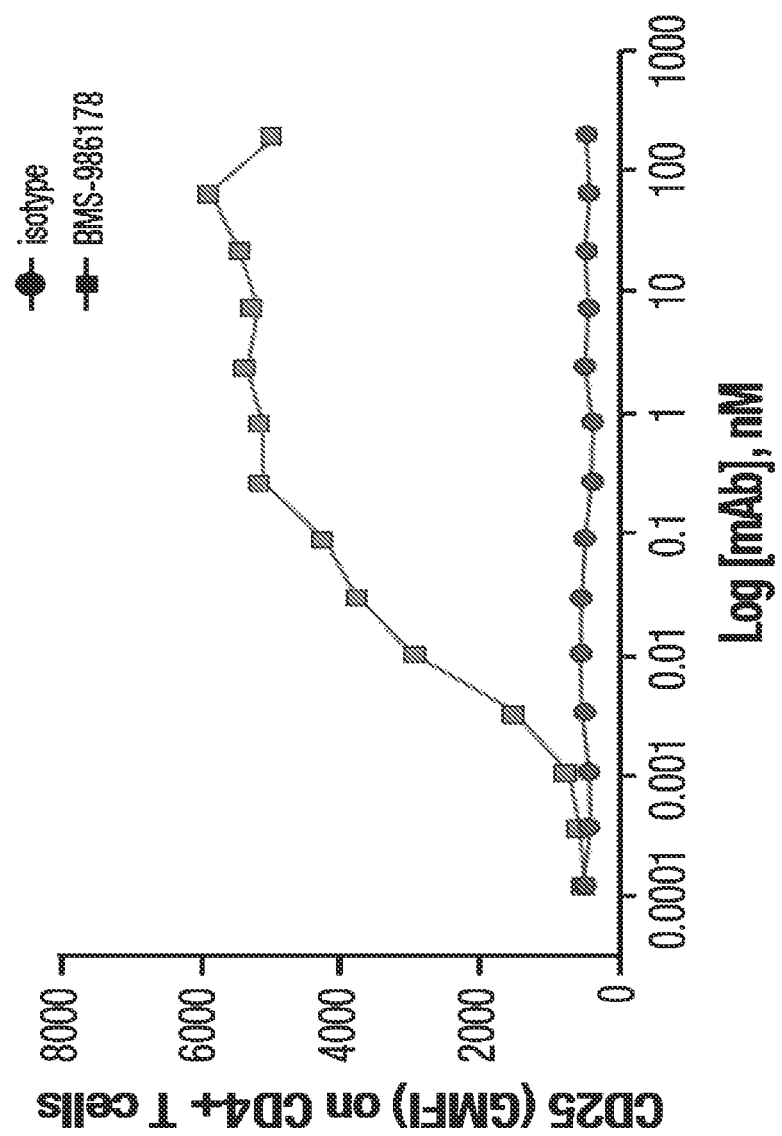
FIG. 31 shows T cell activation as measured by geometric mean fluorescence intensity [GMFI] of CD25 on CD4+ T cells treated with OX-40 agonist antibody (BMS-986178 surrogate mouse antibody) or an isotype antibody.
Figures 32A, 32B:
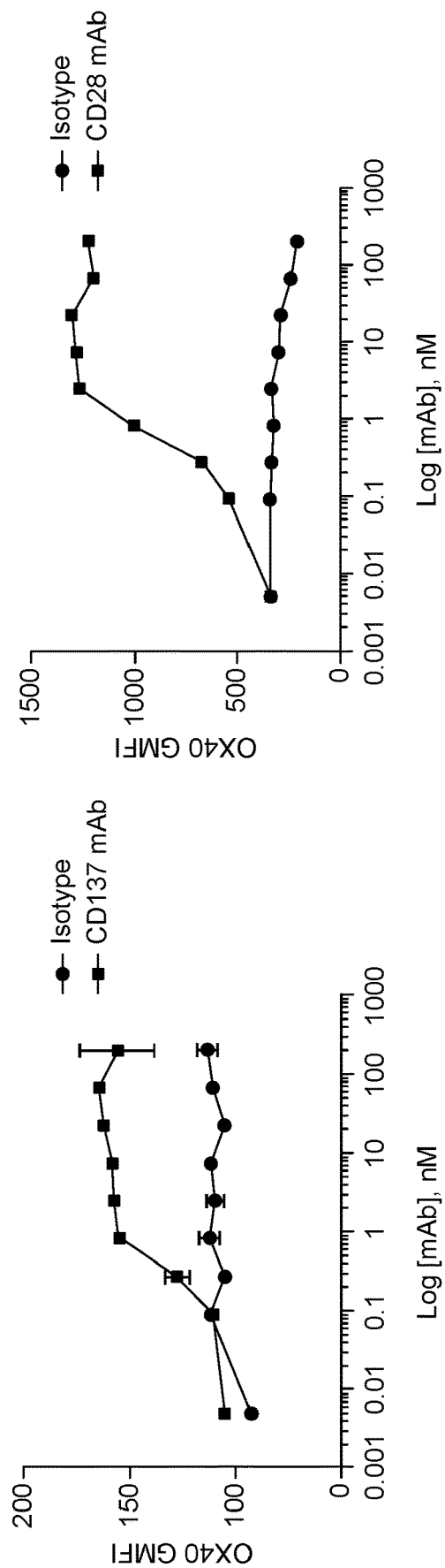
FIGS. 32A and 32B are graphs summarizing the impact of % OX40 RO on total surface expression of OX40 after treatment of CHO cells with CD137 monoclonal antibody (FIG. 32A) or CD28 monoclonal antibody (FIG. 32B) compared to an isotype antibody control.

As shown in FIGS. 15A-15C, OX40.21 induced T cell proliferation, with maximal proliferation obtained between 20-50% receptor occupancy. T-cell activation (as measured by geometric mean fluorescence intensity [GMFI] of CD25 on CD4+ T cells) was achieved at the lowest doses of BMS-986178 and plateaued at 40% OX40 RO. FIG. 31. Collectively, these data suggest that maximum activity of OX40.21 in terms of OX40 surface expression, T cell proliferation, and cytokine production, is obtained from around 20% receptor occupancy. At 100% receptor occupancy, the "hook" effect is observed in which the functionality/activation of T cells is reduced.

Figure 33A:
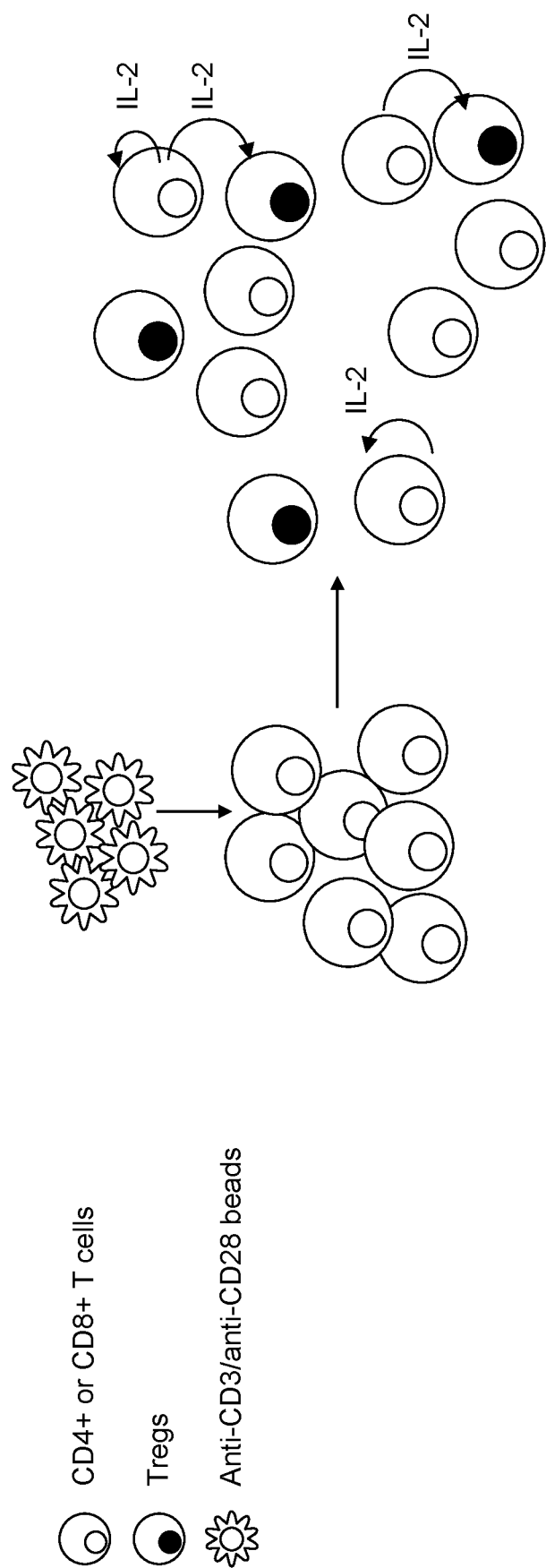

A further experiment was performed to assess suppression of Tregs in T cells treated with BMS-986178. Human CD4+ T cells were differentiated into Tregs and expanded using Dynabeads (αCD3/αCD28; Thermo Fisher Scientific), rapamycin, and interleukin (IL)-2. FIG. 33A depicts the Treg suppression assay. The Treg phenotype was confirmed by flow cytometry as described herein. Purified CD4+ T cells and CD8+ T cells were cultured±Tregs (5:1)+BMS-986178. Then, IL-2 secretion was measured by cytometric bead array assay.

As shown in FIGS. 33B and 33F, BMS-986178-treated $CD4^+$ and $CD8^+$ T cells produced IL-2 in the presence of Tregs, demonstrating that OX40 agonism via BMS-986178 relieved Treg suppression. IL-2 production by $CD4^+$ T cells (FIG. 33B) or $CD8^+$ T cells (FIG. 33F) in the presence of Tregs demonstrated a hook effect. On the other hand, OX40 expression on Tregs from the corresponding cultures (FIGS. 33D and 33H) reached a maximum at approximately 1 μg/mL BMS-986178 and >1 μg/mL of BMS-986178 resulted in reduced OX40 surface expression.

In addition, IL-2 production by stimulated $CD4^+$ T cells alone (FIG. 33C) also demonstrated a hook effect. Also, $CD4^+$ T cells (FIG. 33E) and CD8+ T cells (FIG. 33I) cultured alone exhibited maximal OX40 surface expression at 0.37 μg/mL of BMS-986178, and reduced OX40 expression at >1 μg/mL of BMS-986178. On the other hand, stimulated $CD8^+$ T cells showed maximal IL-2 production regardless of BMS-986178 dose (FIG. 33G).

These data demonstrate that BMS-986178 relieved Treg suppression of $CD4^+$ and $CD8^+$ T cells with a hook effect versus dose.

Figure 16:
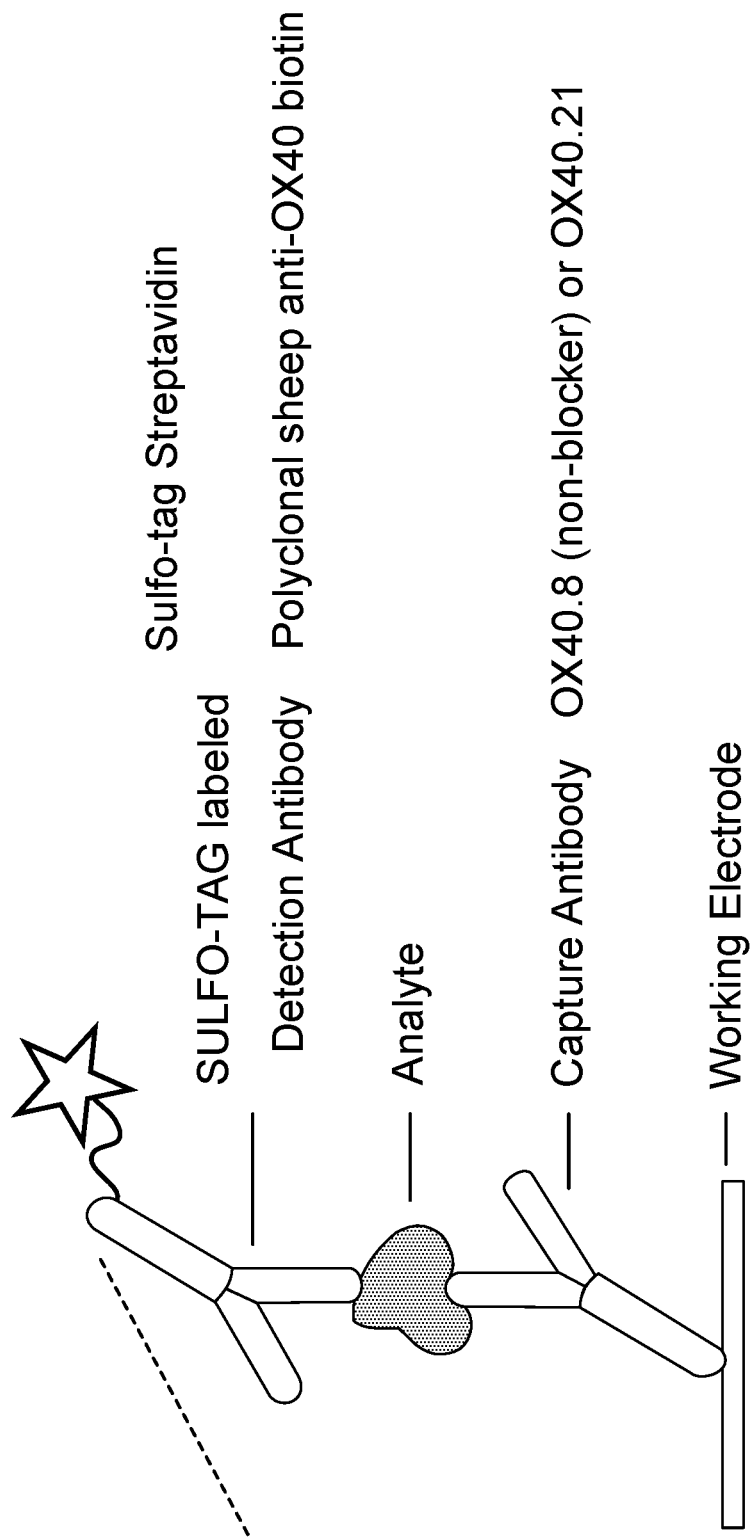
FIG. 16 is a schematic of an ELISA for measuring soluble OX40 (sOX40) levels.

Example 8: In Vitro Assessment of Relationship Between Soluble OX40 and Receptor Occupancy An ELISA specific for soluble OX40 (sOX40) was developed (FIG. 16). Briefly, in the assay, a non-blocking OX40 monoclonal antibody (OX40.8) is first immobilized onto a meso scale discovery (MSD) plate. After blocking the plate with PBS containing 0.5% BSA, the culture supernatant is applied to the plate and incubated. After washing, captured sOX40 is detected using a pre-optimized concentration of sheep polyclonal antibodies biotin conjugated against OX40 (R&D System). After incubation and washes, Sulfo-tag streptavidin is added to detect the sOX40-antibody complexes immobilized onto the plate by electrochemiluminescence. This assay was used to assess the relationship between sOX40 levels and receptor occupancy. Cells were cultured under the same conditions as those described in Example 7, except that, after 4 days of culture, supernatant was collected and sOX40 was quantified using the assay.

Figure 18:
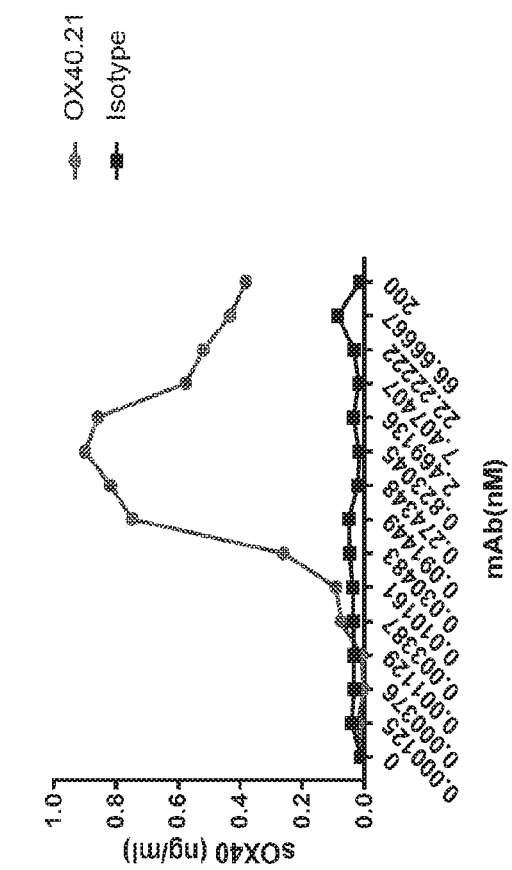
FIG. 18 is a graph showing the levels of soluble OX40, when cells were treated with the indicated concentrations of OX40.21.
Figure 17:
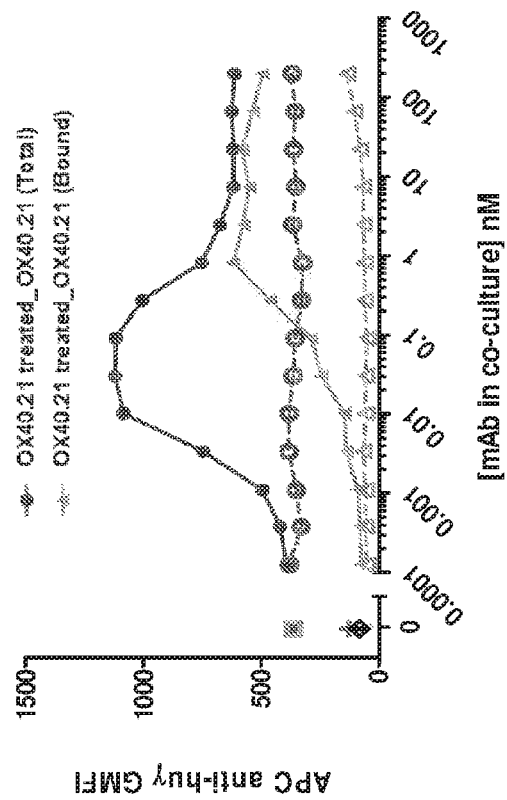
FIG. 17 is a graph showing the levels of surface OX40 expression on cells when cells were treated with the indicated concentrations of OX40.21.
Figure 19:
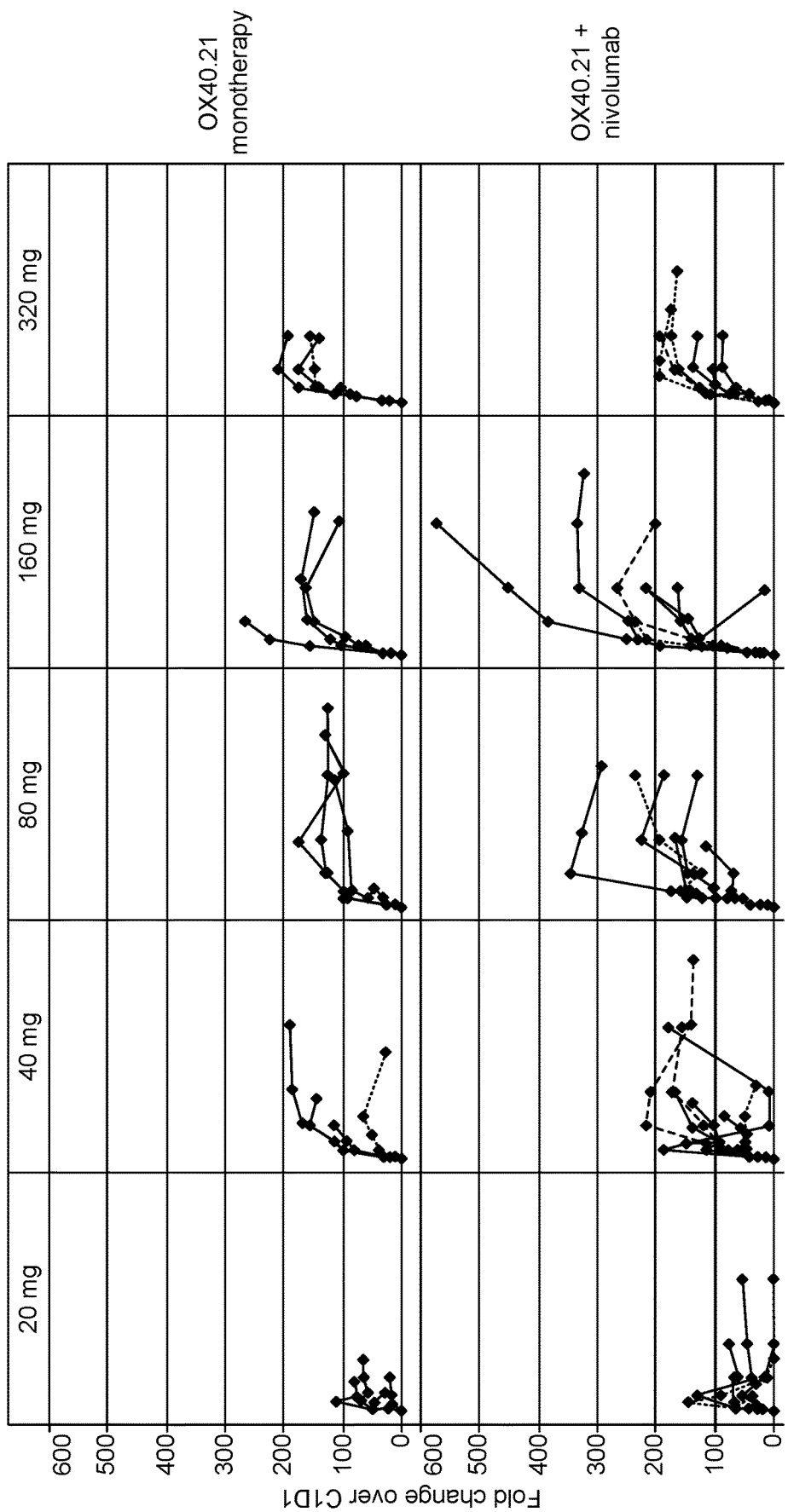
FIG. 19 is a series of graphs showing fold increase over C1D1 of sOX40 when human patients were treated with OX40.21 monotherapy or OX40.21+nivolumab combination therapy, with OX40.21 administered at 20 mg, 40 mg, 80 mg, 160 mg, and 320 mg.

As shown in FIGS. 17 and 18, increasing the concentration of OX40.21 induced OX40 expression on the surface of CD4+ T cells and sOX40 in the supernatant. Loss of sOX40 correlated with the loss of cells surface OX40 at 100% receptor occupancy ("hook" effect). This data suggests that sOX40 can be used as a readout for OX40 agonism and/or T cell activation. In human patients as well, sOX40 levels increased upon treatment with OX40.21 monotherapy and OX40.21+nivolumab (FIG. 19).

Figures 35A, 35B:
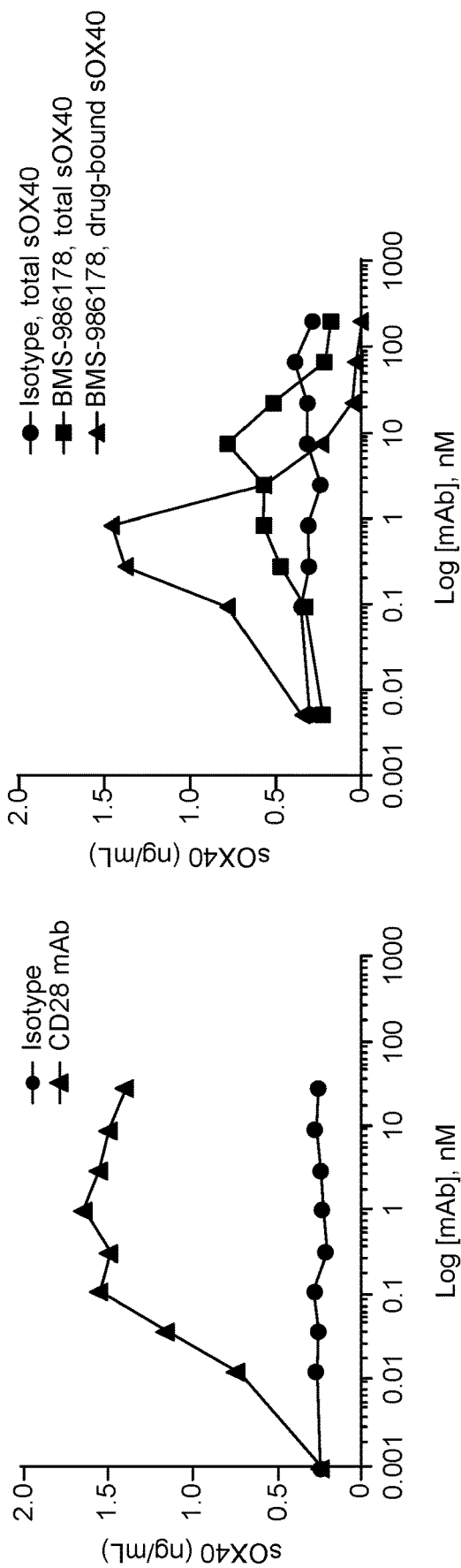
FIG. 35A is a graph showing the levels of soluble OX40, when cells were treated with the indicated concentrations of CD28 monoclonal antibody or an isotype antibody control.
FIG. 35B is a graph showing the levels of total and drug-bound soluble OX40, when cells were treated with the indicated concentrations of BMS-986178 (BMS-986178 surrogate mouse antibody).

Soluble OX40 (sOX40) released by anti-CD28-treated CD4+ T cells was measured using a custom-developed ELISA as described above. As shown in FIG. 35A, this hook effect observed in cells treated with BMS-986178 was unique, as anti-CD28 induced sOX40 release in a dose-dependent manner after reaching a maximum at higher doses. Further, as shown in FIG. 35B, the majority of sOX40 released by CD4+ T cells was bound to BMS-986178. Thus BMS-986178-mediated T-cell activation induced sOX40 release, which decreased as OX40 RO approached 100%.

Total sOX40 and sOX40 bound by OX40.21 were also determined. Briefly, total T cells were purified from human whole blood using Ficoll gradient centrifugation. CD4+ T cells were isolated from PBMC using Miltenyi CD4+ isolation kit. Isolated T cells were cultured in presence of irradiated CHO-OKT3-CD32A (artificial antigen presenting cells) and tested with serial dilution of an agonistic anti-OX40 antibody, isotype control, or anti-CD28 (clone 28.2). At pre-defined time points, supernatant were collected. Soluble OX40 was quantified using the ELISA described above.

As shown in FIGS. 20A and 20B, the levels of sOX40 correlated with the cell surface expression of OX40, cleavage of OX40 is cell activation-dependent but not specific to OX40 agonist, and complete sOX40 bound to OX40.21 correlates with the decrease in level of total soluble OX40 (i.e., 100% sOX40 bound when the "hook" effect on sOX40 is detected).

Next, the ability of anti-CD28 antibody to rescue the OX40.21-mediated "hook" effect on sOX40 levels was tested. Total T cells were purified from human whole blood using Ficoll gradient centrifugation. CD4+ T cells were isolated from PBMC using Miltenyi CD4+ isolation kit. Isolated T cells were cultured in presence of irradiated CHO-OKT3-CD32A and in presence of a serial dilution of an agonistic anti-OX40 antibody, isotype control alone or in combination with anti-CD28 antibody (clone CD28.2) at a constant concentration. In another instance, anti-CD28 antibody at a constant concentration was used alone and serial dilutions of OX40.21 or isotype control were added 72 hours (3D) later for 18 hours. Supernatant was collected at a pre-defined time (D4). Soluble OX40 was quantified using the MSD ELISA described above.

Figure 21B:
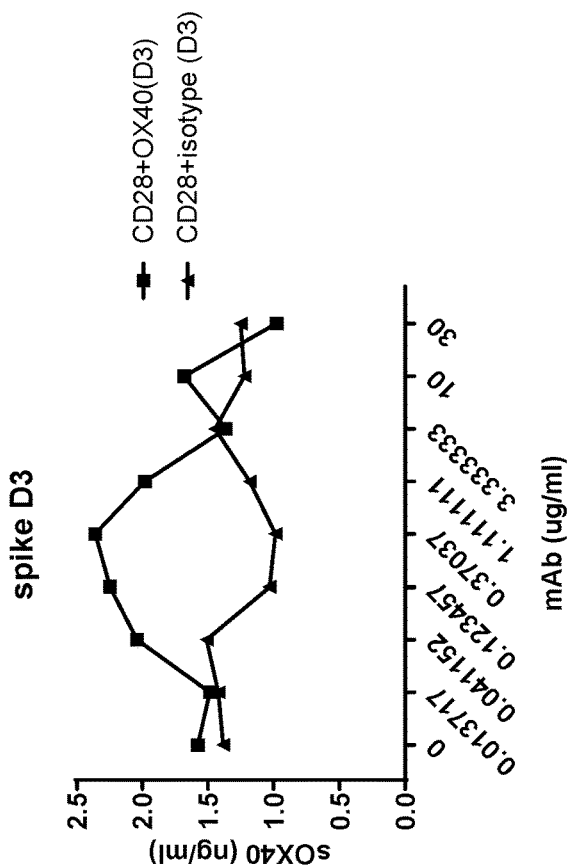
FIG. 21B is a graph showing the effects on day 4 sOX40 levels after OX40.21 is added to CD28 at day 3 in culture.
Figure 21A:
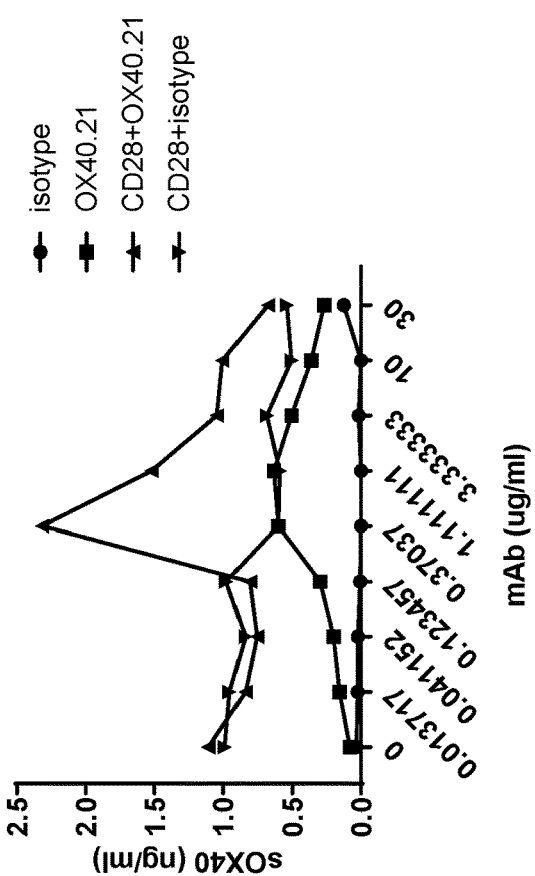
FIG. 21A is a graph showing the additive effects on sOX40 levels when co-stimulating cells with OX40.21 and an anti-CD28 antibody.

As shown in FIGS. 21A and 21B, co-stimulation of cells with OX40.21 and anti-CD28 antibody had an additive effect on sOX40 levels. However, CD28 co-stimulation did not rescue the OX40.21-induced "hook" effect on sOX40. Treatment of cells pre-activated by anti-CD28 antibody with OX40.21 was sufficient to induce sOX40 release and observe the "hook" effect on sOX40 levels. Taken together, this data indicates that sOX40 can be used as a biomarker of primary human T cell activation both in vitro and in patients treated with immunostimulatory agonists in combination with checkpoint blockade. Measurement of sOX40 may be used as a clinical biomarker to determine the optimal dose and schedule in patients receiving agonistic antibodies that bind to immunostimulatory receptors as monotherapy or in combination with checkpoint blockade. Furthermore, the generation of sOX40 is not a mechanism which can account for the loss of OX40 from the cell surface above 20-40% RO of OX40.21, since sOX40 is also lost at concentrations leading to RO above the optimal 20-80% range. This suggests that cell surface and sOX40 are regulated in a similar fashion.

Example 9: In Vitro Assessment of OX40 Internalization

This Example assessed the internalization of OX40 following treatment with blocking (OX40.21) and non-blocking (OX40.8) antibodies. A general schematic of the assay is shown in FIG. 22.

More specifically, in vitro generated CD4+ Tregs were activated for 48 hours with CD3/CD28 dynabeads. A serial dilution of OX40.21, the non-blocker OX40.8, and isotype control were incubated with the cells for 2 hours on ice followed by the addition of pH sensitive conjugated anti-human Fc for 2 hours at 37° C. After fixation, cells were analyzed by ArrayScan for internalization.

Figure 23:
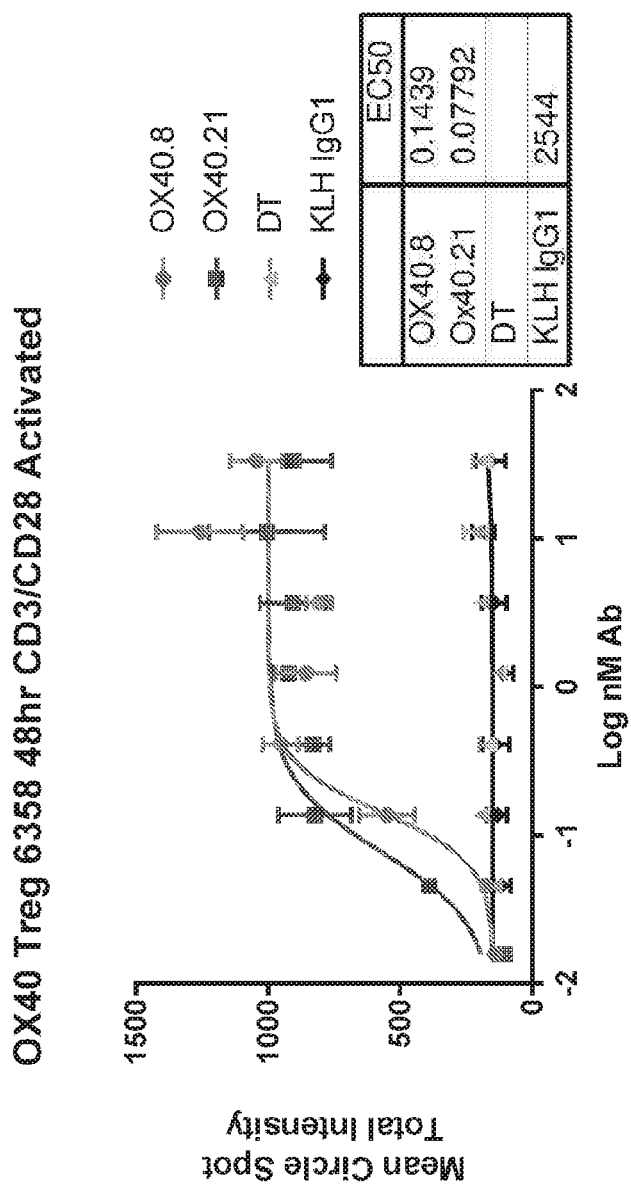
FIG. 23 is a graph showing internalization of OX40 in Tregs activated with CD3/CD28 and subsequently treated with IgG1, DT, OX40.21 (ligand blocking antibody), or OX40.8 (ligand non-blocking antibody).

As shown in FIG. 23, OX40.21 and OX40.8 were internalized upon cross-linking in Tregs.

In addition, internalization of OX40 in response to two different doses (0.01 nM and 100 nM) of BMS-986178 was measured. In this assay, activated Tregs or CD4+ T cells were incubated with an isotype control mAb or BMS-986178. Then, pH-sensitive dye (pHrodo)-conjugated anti-Fc was added. After, the cells were fixed for readout on ArrayScan VTI (Thermo Fisher Scientific).

As shown in FIG. 36, Tregs or CD4+ T cells treated with 0.01 or 100 nM of BMS-986178 internalized drug-bound OX40 in a BMS-986178 concentration-dependent manner.

Example 10: Effect of FcγR-Mediated Cross-Linking on Agonistic Activity of OX40.21

This Example demonstrates the effects of FcγR-mediated cross-linking on the agonistic activity of OX40.21. Briefly, CHO cells were engineered to express a cell membrane-bound scFv version of the anti-human agonist CD3 clone, OKT3, either with (+FcγR) or without (−FcγR) the H131 allele of human FcγRIIa (CD32a-H131) denoted as OKT3scFv and hFcγR, respectively. CHO cells were irradiated to limit their proliferation and placed in culture with primary human CD4 T cells with various amounts OX40.21. T cell proliferation and secretion of IFN-γ by primary human CD4 T cells was assessed over a 4 day period.

Figure 24:
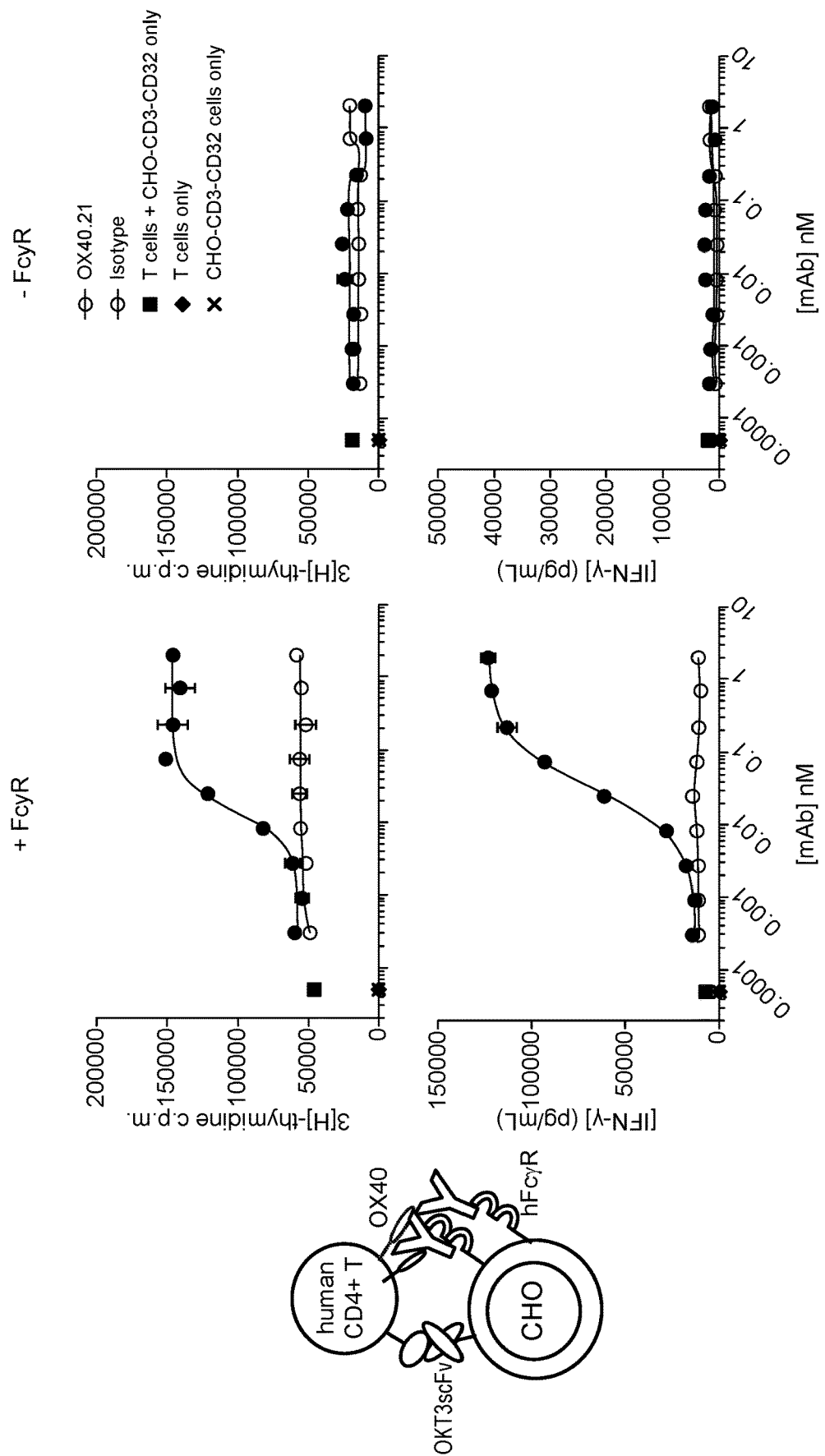
FIG. 24 is a series of graphs showing the effects of FcγR-mediated cross-linking on the agonistic activity of OX40.21.

As shown in FIG. 24, treatment with BMS-986178 induced CD4+ T cell proliferation and IFN-γ production in a dose-dependent and cross-linking dependent manner. FcγR-mediated crosslinking promoted BMS-986178-mediated increases in both IFN-γ secretion and T cell proliferation. However, proliferation and IFN-γ were absent when CHO cells lacked CD32a (CD32a-H131), suggesting that BMS-986178 activity requires FcγR-mediated cross-linking.

Example 11: Characterization of Peripheral Pharmacodynamics Markers Induced by Anti-OX40 Antibody Monotherapy and Anti-PD1 Combination Therapy This Example demonstrates the induction of certain pharmacodynamics markers in mice with OX40.23 monotherapy or with a combination of OX40.23 and an anti-PD1 antibody, and in human patients treated with OX40.21 in combination with anti-PD1 antibody (nivolumab).

Figure 25:
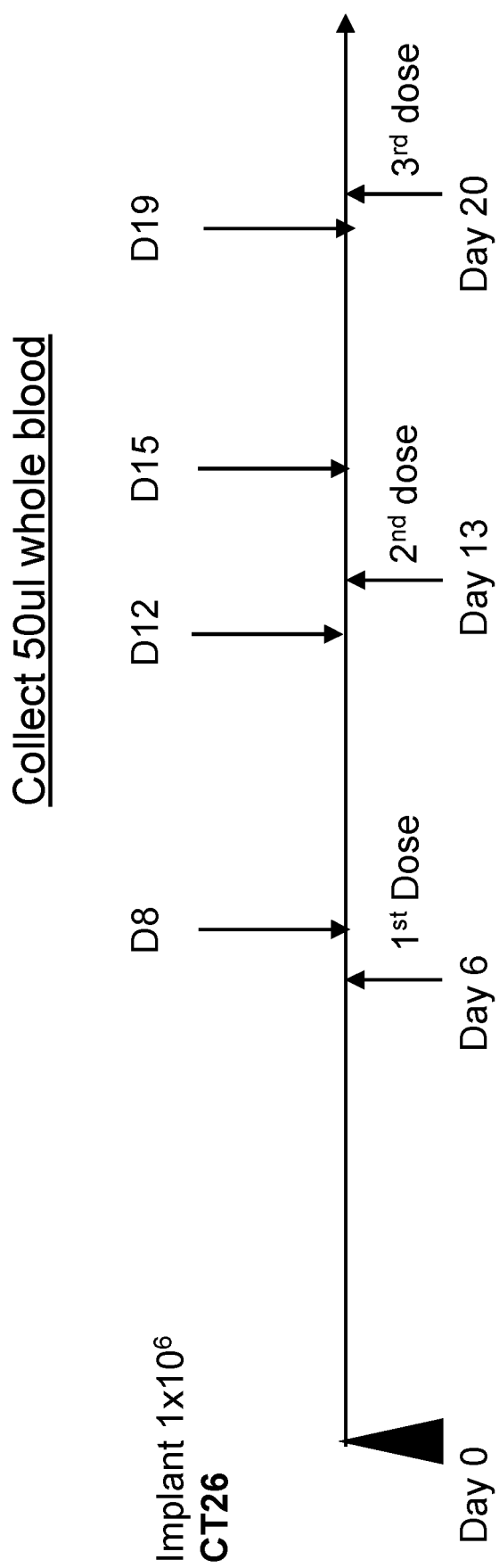
FIG. 25 is a schematic showing the dosing and sampling schedule for treatment of the CT26 mouse tumor model with OX40.23 as monotherapy or in combination with anti-PD1 antibody, for the assessment of peripheral pharmacodynamics markers.

Mice with established CT26 tumors were treated by either OX40.23 monotherapy or in combination with anti-PD-1 antibody. OX40.23 does escalation was started from 0.01 mg/kg with 3 fold of increase to 90 mg/kg. Anti-PD-1 antibody was dosed at 10 mg/kg (or 200 ug/mouse flat dose). OX40.23 and anti-PD1 antibody were administered in the same schedule on Day 6, 13 and 20. 50 ul of whole blood was collected from individual mice on Days 8, 12, 15 and 19. Flow analyses were performed to determine induction of peripheral pharmacodynamic markers (ICOS, FOXP3, Ki67, and CD44) in CD4+ and CD8+ T cells following treatment with OX40.23-mIgG1±anti-PD-1. FIG. 25 shows a schematic of the dosing schedule.

Figure 26A:
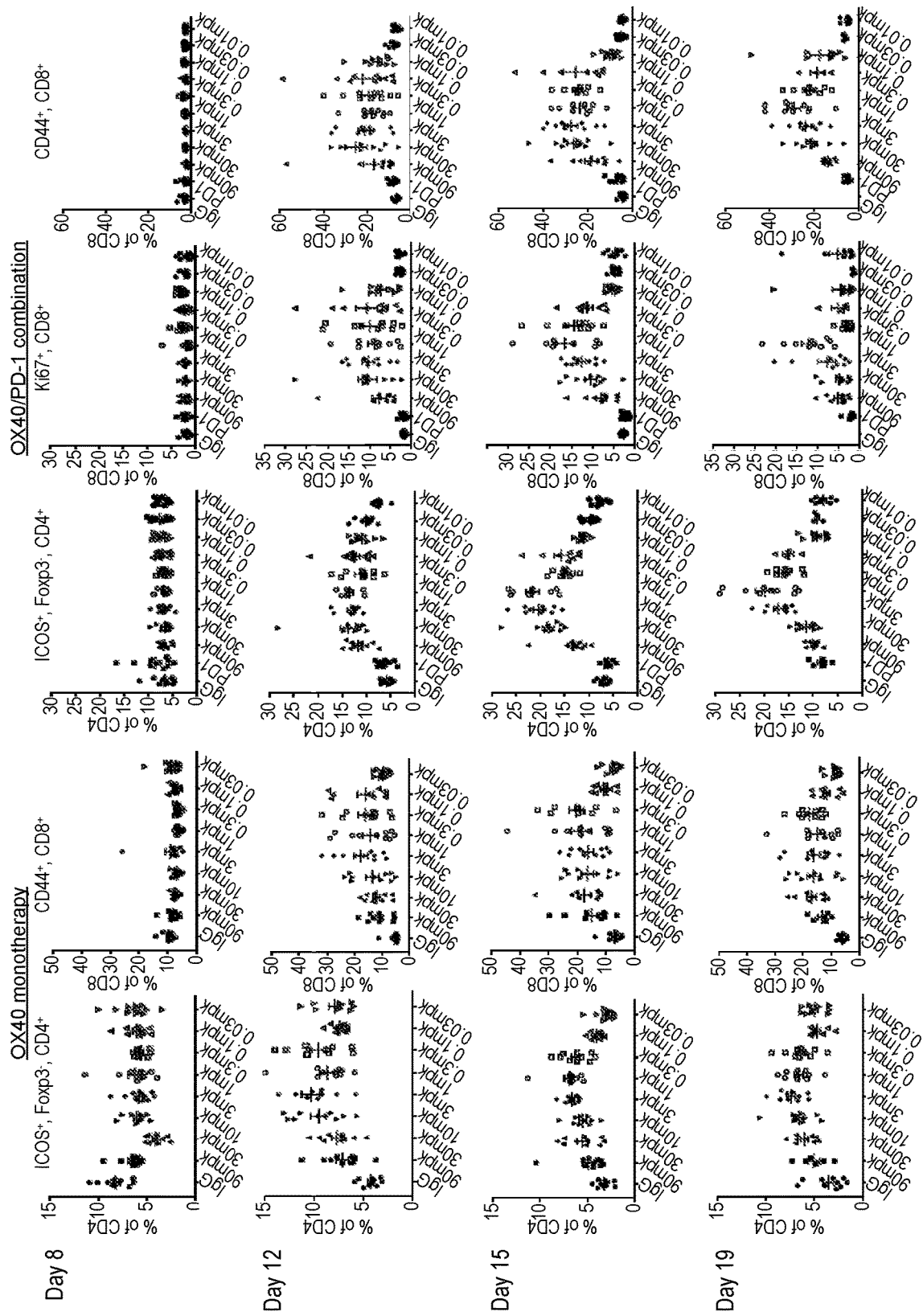
FIG. 26A is a series of graphs showing the effects of OX40.23 monotherapy or combination therapy with anti-PD1 antibody on levels of ICOS, Ki67, and CD44 in CD4+ T cells and CD8+ T cells. In the OX40 monotherapy panels, the x-axis labels, from left to right, are IgG, 90 mpk, 30 mpk, 10 mpk, 3 mpk, 1 mpk, 0.3 mpk, 0.1 mpk, and 0.03 mpk. In the OX40/PD-1 combination panels, the x-axis labels, from left to right, are IgG, PD1, PD1+90 mpk, PD1+30 mpk, PD1+10 mpk, PD1+3 mpk, PD1+1 mpk, PD1+0.3 mpk, PD1+0.1 mpk, PD1+0.03 mpk, and PD1+0.01 mpk.

As shown in FIG. 26A, both CD4+ T cells and CD8+ T cells showed dose-dependent upregulation of activation makers (ICOS, CD44, Ki67) on both CD4 effector T cells (Foxp3−) and CD8+ T cells, and downregulation at higher doses ("hook" effect).

Figures 26B, 26C:
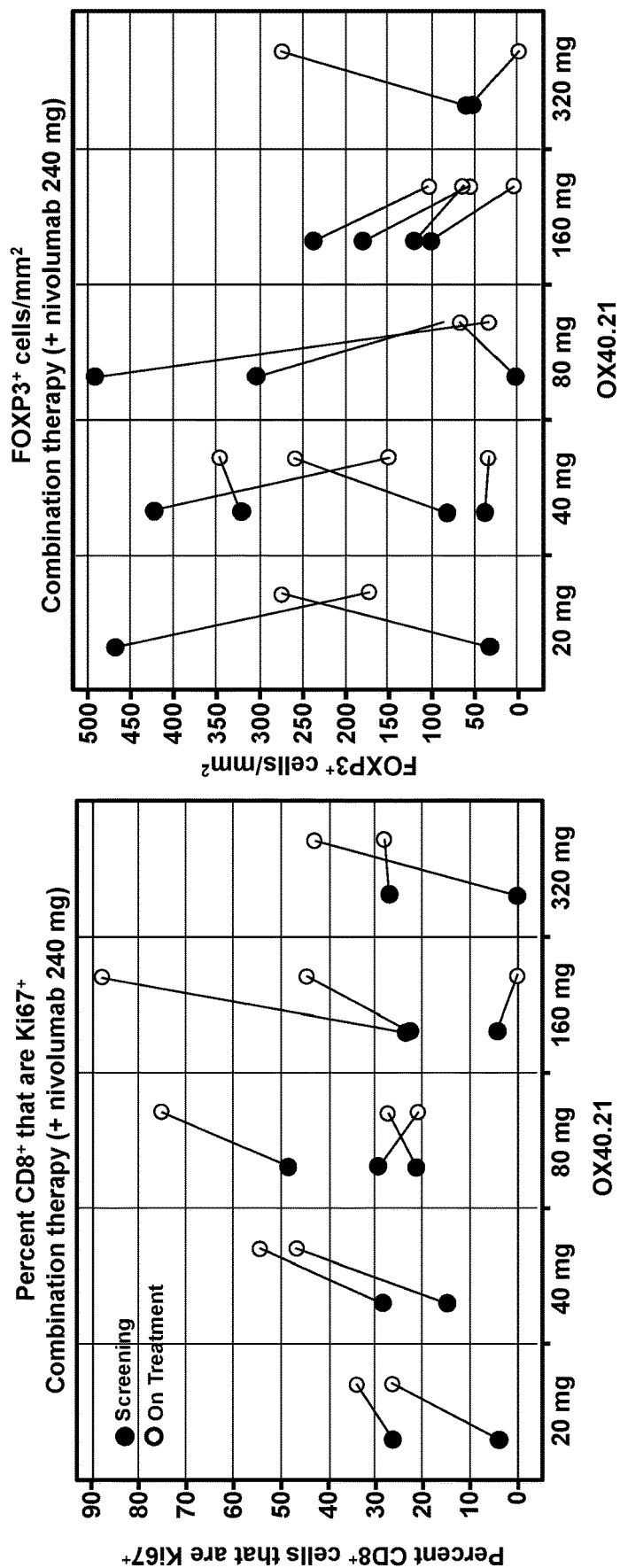
FIG. 26B shows the percentage of CD8+ cells that are Ki67+ in the tumor stroma of human patients treated with a combination of OX40.21 (20, 40, 80, 160, or 320 mg)+nivolumab.
FIG. 26C shows the percentage of FOXP3+ cells in the tumor stroma of human patients treated with OX40.21 (20, 40, 80, 160, or 320 mg)+nivolumab.

Similarly, in human patients treated with OX40.21+anti-PD1 antibody (nivolumab), the combination treatment increased proliferating (Ki67+) CD8+ T cells (FIG. 26B), and decreased FOXP3+ cells in tumor stroma (FIG. 26C).

Figure 26D:
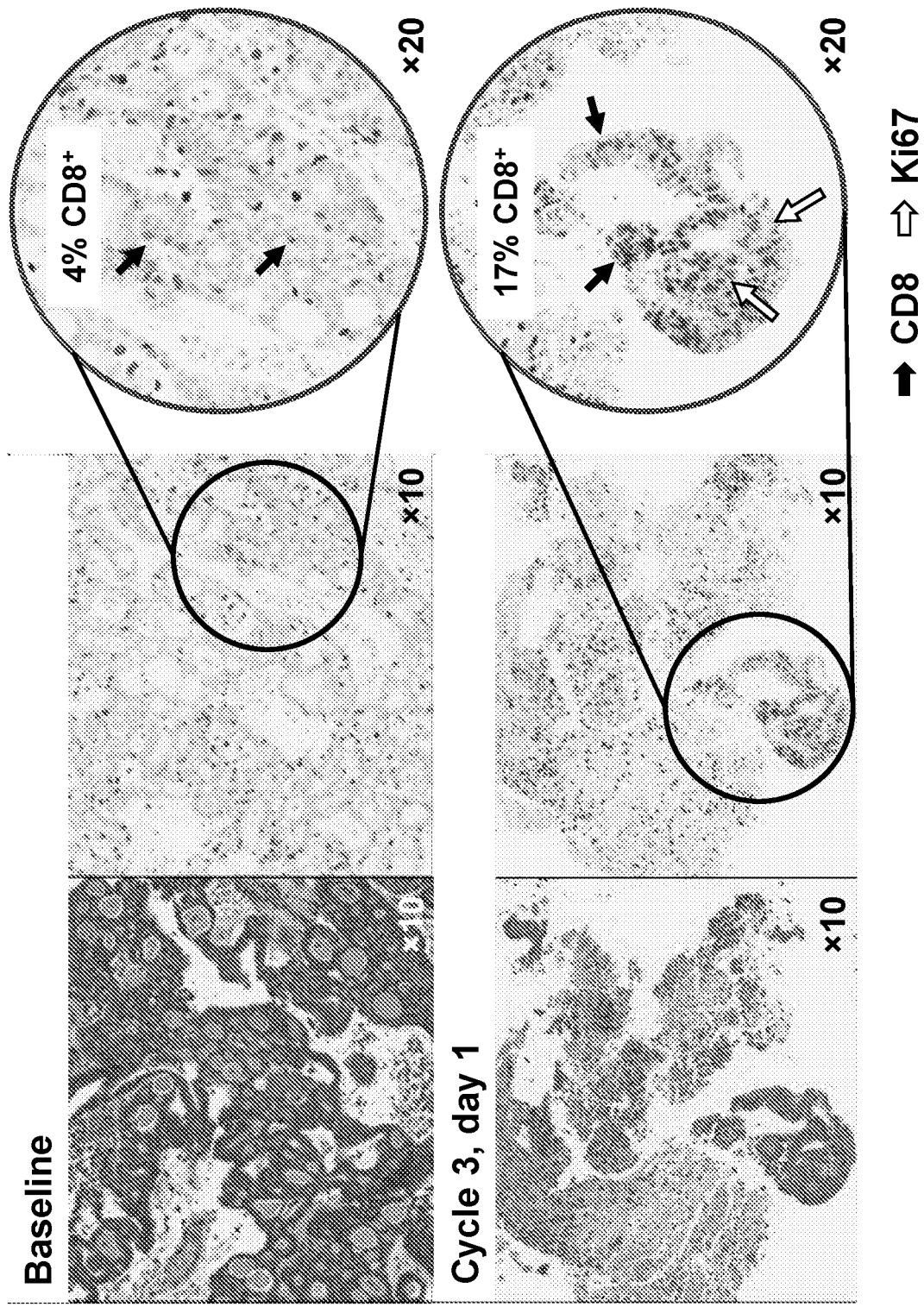
FIG. 26D shows an immunohistochemical analysis of Ki67+CD8+ T cells from tumor samples of a human patient with endometrial cancer treated with OX40.21 (320 mg)+nivolumab (240 mg).

Results from immunohistochemical analysis of patient tumor samples were consistent. For example, as shown in FIG. 26D, samples from a 68-year-old female patient with endometrial cancer, who had received 3 lines of prior therapy (medroxyprogesterone, letrozole, and carboplatin and paclitaxel) and had achieved a partial response with OX40.21 (320 mg)+nivolumab (240 mg), showed an increased number of Ki67+ CD8+ T cells. The combination therapy also decreased FoxP3+ cells in tumor samples from patients with ovarian cancer who had achieved stable disease. As shown in FIG. 26E, reduced FoxP3+ cells were observed in a 59-year-old female patient with ovarian serous cancer who had received prior surgery and chemotherapy (carboplatin and paclitaxel) (top panel), and a 72-year-old patient with ovarian adenocarcinoma who had received prior surgery and chemotherapy (carboplatin and paclitaxel) (lower panel).

Example 12: Correlation Between Early T Cell Activation Markers and Tumor Responses to Anti-OX40 and Anti-PD1 Combination Therapy This Example assessed the correlation between early T cell activation markers and tumor responses to anti-OX40 (OX40.23) and anti-PD1 combination therapy.

Mice were separated into two groups based on tumor progression status at Day 20. Mice with a tumor volume >100 mm$^3$ were considered non-responders, and those with a tumor volume ≤100 mm$^3$ were considered responders.

Figure 27B:
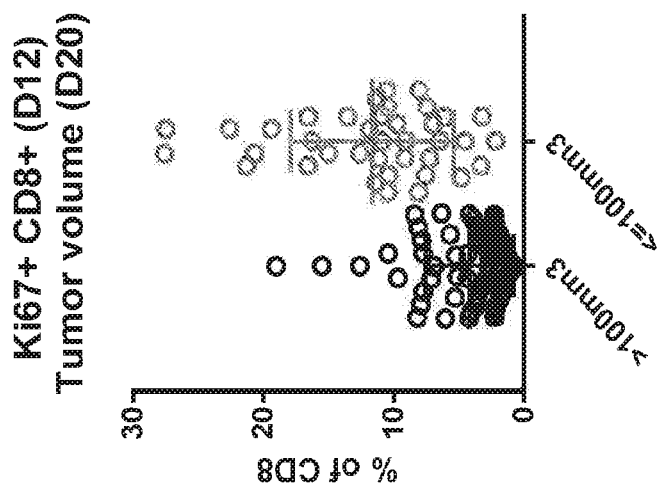
FIGS. 27A and 27B show graphs of the percentage of CD8+ T cells that are positive for CD44 (FIG. 27A) and Ki67 (FIG. 27B), based on non-responder (tumor volume >100 mm$^3$) or responder (tumor volume ≤100 mm$^3$) status.
Figure 27A:
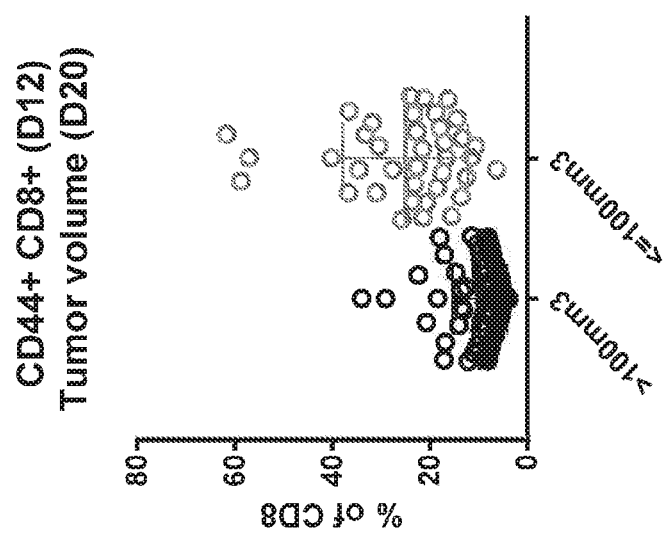
Figure 27C:
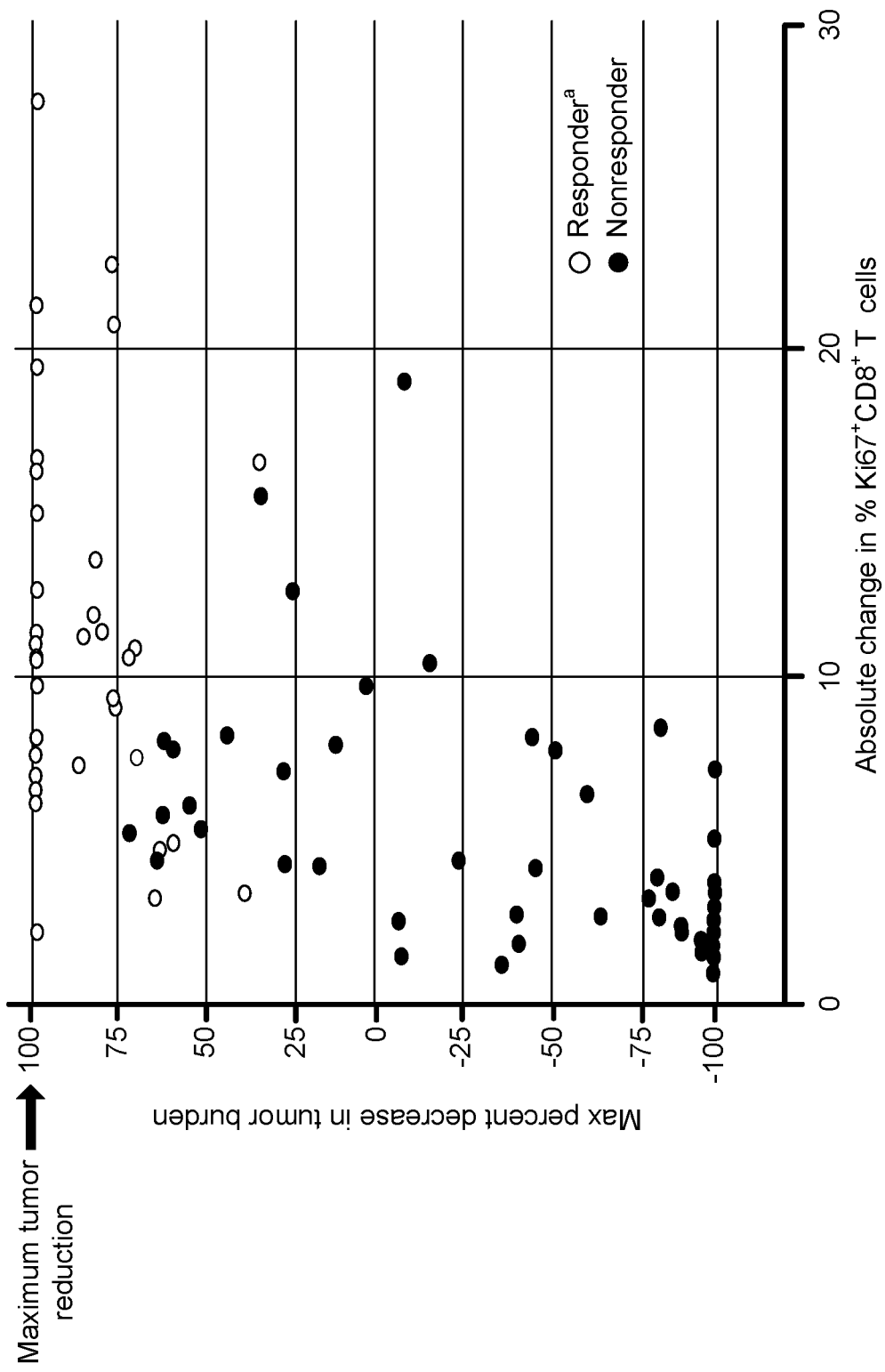
FIG. 27C is a graph showing the absolute change in % Ki67+CD8+ T cells by anti-tumor activity (max percent decrease in tumor burden).
Figure 27D:
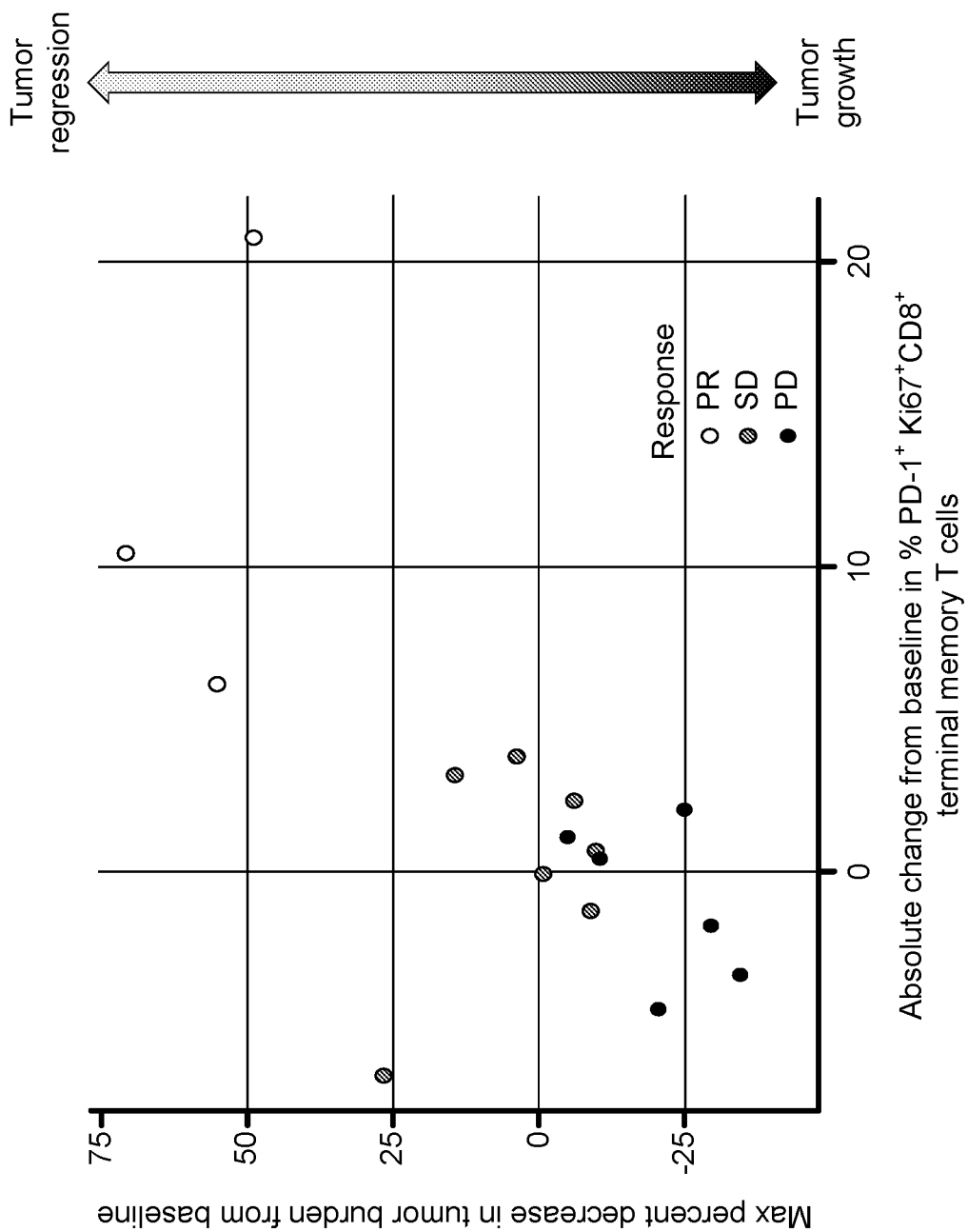
FIG. 27D is a graph showing changes in Ki67+CD8+ T cells by anti-tumor activity (percent decrease in tumor burden). PR: partial response, PD: progressive disease, SD: stable disease.

As shown in FIGS. 27A and 27B, the percentages of CD44+ CD8+ and Ki67+ CD8+ T cells at Day 12, when there was no clear separation of tumor volume, were positively correlated to the subsequent tumor response, which may allow for defining optimal dose and schedule for combination therapy. The data plotted as absolute change in % Ki67+CD8+ T cells by maximum % decrease in tumor burden also showed a positive correlation between reduction in tumor burden and proliferating CD8+ T cells (FIG. 27C). Similarly, in human patients treated with OX40.21+anti-PD1 antibody (nivolumab), anti-tumor activity was correlated with increased proliferating Ki67+CD8+ T cells (FIG. 27D).

Example 13: Effects of Increasing Doses of Anti-ICOS Antibody on Tumor Growth

This Example demonstrates that an agonistic anti-ICOS antibody exhibits reduced efficacy at higher doses (i.e., the "hook effect") in anti-ICOS+anti-PD1 combination therapy.

Briefly, mice (averaging about 20 mg in weight) with established CT26 tumors were treated by either anti-PD-1 monotherapy or in combination with anti-ICOS antibody. Anti-ICOS dose escalation was started from 0.1 mg/kg with 3 fold of increase to 10 mg/kg (or a maximum dose of approximately 200 μg/mouse flat dose). Anti-PD-1 antibody was dosed at 10 mg/kg (or a maximum dose of approximately 200 μg/mouse flat dose). Anti-ICOS and anti-PD1 antibodies were administered in the same schedule (i.e., every 4 days starting on day 7) following tumor implantation.

Figure 28:
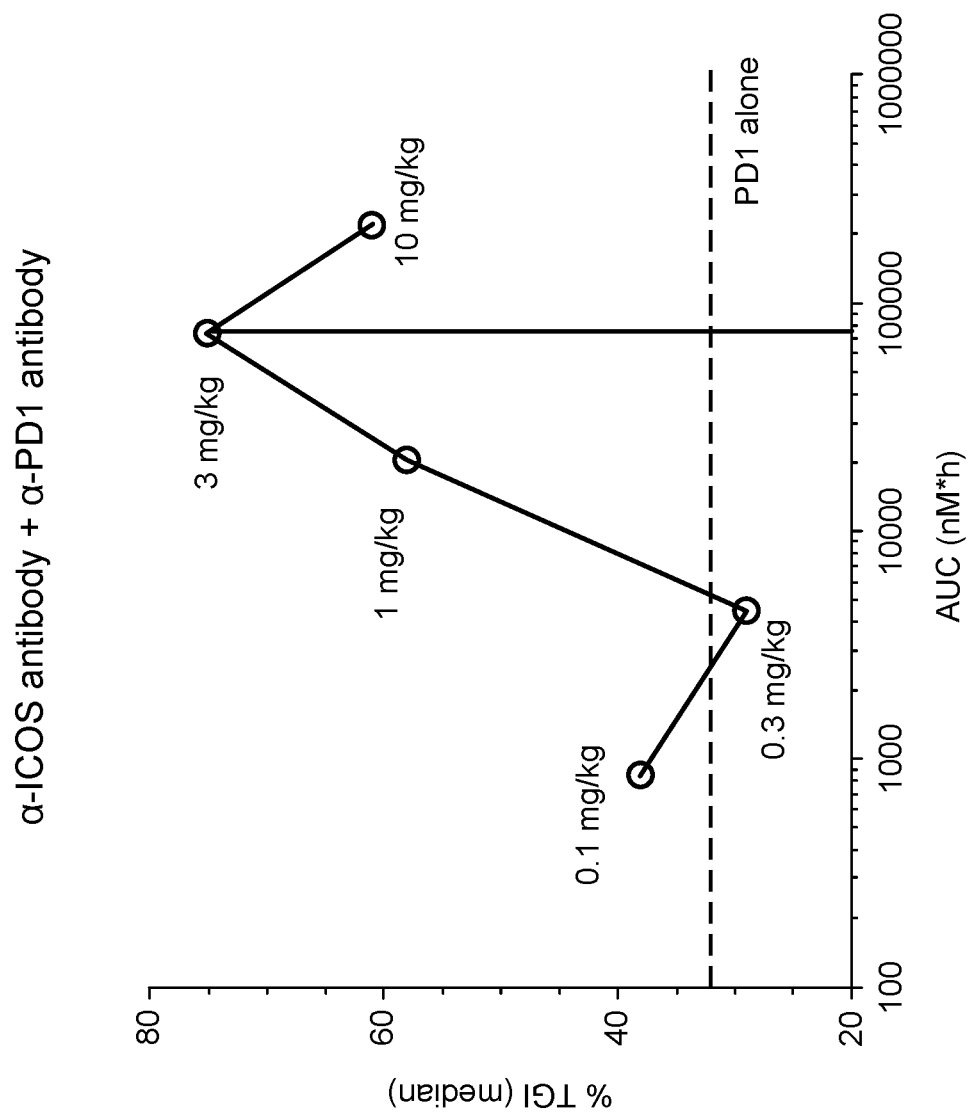
FIG. 28 is a graph showing the effects of increasing doses of an anti-ICOS antibody in anti-ICOS+anti-PD1 combination therapy on tumor growth inhibition in a mouse model.

As shown in FIG. 28, maximal tumor growth inhibition (TGI) in anti-ICOS+anti-PD1 combination therapy was observed at a lower dose of the anti-ICOS antibody (3 mg/kg) than the maximal dose tested (10 mg/kg), demonstrating a decrease in TGI at doses greater than 3 mg/kg. This suggests that, similar to agonistic anti-OX40 antibodies, agonistic antibodies that target other immunostimulatory receptors, such as ICOS, exhibit the "hook effect" and achieve maximal efficacy at sub-saturating doses.

Example 14: Selection of First-in-Human Starting Dose of OX40.21 Using a Pharmacokinetic/Pharmacodynamics (PK/PD)-Based Approach First-in-human (FIH) doses of oncologic agents are conventionally based on the International Conference on Harmonisation Guideline, which recommends the appropriate FIH starting dose to be 1/6 of the highest non-severely toxic dose (HNSTD) from non-rodents, or the minimal anticipated biological effect level (MABEL), for biopharmaceuticals with immune agonistic properties. However, MABEL-based approaches fail to offer clinical benefits to patients. This Example describes a PK/PD-based approach to select a FIH starting dose based on anti-tumor efficacy, i.e., the intended pharmacological effect.

Briefly, flow cytometry was used to determine in vitro binding half maximal effective concentration ($EC_{50}$) values in human and murine activated T cells. For PK/PD determination in mice, mouse surrogate antibodies (hamster anti-mouse OX40 agonist monoclonal antibodies reformatted as mouse IgG1 (mIgG1) and IgG2a (mIgG2a) isotypes) were used because OX40.21 does not bind to mouse OX40. For anti-tumor efficacy, percent tumor growth inhibition (% TGI) was determined from the median value of the area under tumor growth curves in treatment and control groups using mouse MC38 and CT26 colon adenocarcinoma models. PK studies were performed in cynomolgus monkeys using the surrogate antibodies and OX40.21. Human PK was predicted from monkey data using simple allometry, with a power exponent of 0.85 and 1 for the clearance and the steady-state volume of distribution (Vss), respectively. In vitro cytokine release was evaluated using a dry coat format (see, e.g., Finco et al. *Cytokine* 2014; 66:143-55). The adenovirus serotype 5-simian immunodeficiency virus (Ad5-SIV) vaccination study was performed with OX40.21 in cynomolgus monkeys, with dosing on day 1 and day 28. The 1-month repeat-dosing toxicology study was conducted in cynomolgus monkeys, with monkeys administered OX40.21 at 30 mg/kg, 60 mg/kg, and 120 mg/kg in a 30-minute intravenous (iv) infusion once per week for 5 weeks.

As shown in Table 6, mouse surrogate antibodies exhibited binding $EC_{50}$ values similar to that of OX40.21.

TABLE 6

Binding EC50 (pM) in activated T cells

| Antibody | Human T cells | Cynomolgus T cells | Mouse T cells |
|---|---|---|---|
| OX40.21 (human) | 72 | 68 | No binding |
| mIgG1 (mouse) | No binding | No binding | 130 |
| mIgG2a (mouse) | No binding | No binding | 220 |

Figure 29:
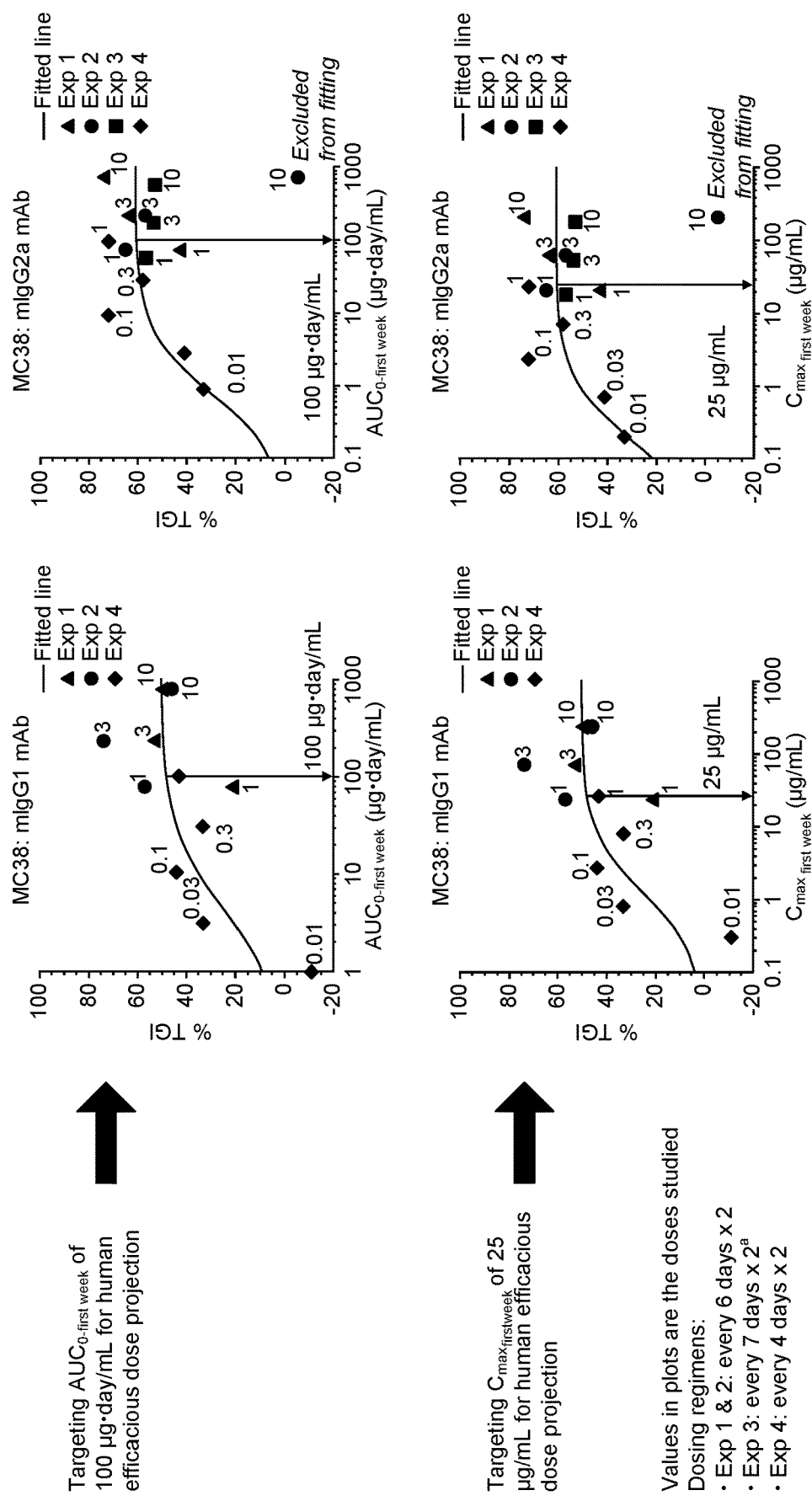
FIG. 29 is a series of graphs showing exposure-response relationships of mIgG1 and mIgG2a monoclonal anti-OX40 antibodies in a mouse MC38 tumor model.

Next, a PK/PD analysis was conducted to correlate the maximum drug concentration during the first week ($C_{max(first\ week)}$) or the area under the curve ($AUC_{0\text{-}first\ week}$) with anti-tumor efficacy. For the purpose of human efficacious dose projection and to be more conservative for a broad patient coverage, the analysis was centered on anti-tumor efficacy in the MC38 model due to less sensitivity to anti-OX40 treatment compared with the CT26 model. Because the PK of mouse surrogates was significantly affected by immunogenicity in the second week due to their hamster origin, the first-week $C_{max}$ and AUC data were simulated under various regimens used for efficacy testing, with the assumption that pharmacological action of an agonist is driven by the $C_{max}$ or initial drug exposure. Exposure-response relationships of mIgG1 and mIgG2 monoclonal antibodies in the mouse MC38 tumor model are shown in FIG. 29.

Corresponding PK experiments were also conducted in cynomolgus monkeys, the results of which are summarized in Table 7.

TABLE 7

| Dose, mg/kg | $AUC_{total}$, µg/mL × day | $T_{1/2}$, days | Clearance, mL/day/kg | Vss, mL/kg |
|---|---|---|---|---|
| 0.4 | 86 ± 5 | 5.6 ± 0.5 | 4.8 ± 0.2 | 36 ± 2 |
| 4 | 785 ± 138 | 6.2 ± 0.6 | 5.3 ± 1.0 | 49 ± 12 |

Based on the mouse and monkey data above, the predicted human $T_{1/2}$ was 9 days. By achieving the same $AUC_{0\text{-}first\ week}$ and $C_{max(first\ week)}$ in humans as those in mice, the human efficacious dose of OX40.21 was projected to be 1 mg/kg. The human starting dose was selected to be 4-fold below the efficacious dose projected (i.e., 0.25 mg/kg or 20 mg for a body weight of 80 kg) to reach the clinically relevant dose more efficiently.

Additional supporting data were obtained to inform FIH starting dose selection, as follows:

An Ad5-SIV vaccination study with OX40.21, when administered to monkeys on days 1 and 28, revealed a minimal enhancement of vaccine-induced T-cell response at an IV dose of 4 mg/kg.

OX40.21 did not induce cytokine release or increase activation of expression markers in human peripheral blood mononuclear cells using a dry-coat format at the highest concentration tested (10 µg/well or 33 µg/mL approximated using an incubation volume of 0.3 mL).

The HNSTD or the no-adverse-event level from a 1-month repeat-dose toxicology study in monkeys was determined to be 120 mg/kg/week, with the one-sixth HNSTD dose calculated be 17 mg/kg (exposure based) or 20 mg/kg (body weight based).

Clinical experience with another mouse anti-human OX40 agonist mAb reported in the literature showed no acute toxicity in patients with cancer, despite the fact that drug concentrations 40 µg/mL) in humans at the highest dose (2 mg/kg) tested were well maintained throughout the first week of dosing (see Curti et al., Cancer Res 2013; 73:7189-98). At 2 mg/kg, the human $C_{max}$ was about 80 µg/mL, or >1,500-fold over the in vitro binding $EC_{50}$ (48 ng/mL or 0.3 nM) reported.

Table 8 summarizes the $C_{max}$ margin at the PK/PD-based FIH stating dose and additional supporting data mentioned above.

TABLE 8

|  | PK/PD-based FIH starting dose | Toxicology based FIH starting dose (1/6 monkey HNSTD) | No effect level in dry-coat cytockine release assay[a] | Minimal vaccine-induced T-cell response in monkeys | Clinically tolerated exposure with previously reported anti-OX40 agonist |
|---|---|---|---|---|---|
| Dose, mg/kg | 0.25 | 17-20 | 1.3 | 4 | 2 |
| $C_{max}$, µg/mL | 6.3 | 425-500 | 33 | 78 | 80 |
| $C_{max}$ margin (vs PK/PD-based FIH starting dose) | NA | 68-80x | 5.3x | 13x | 2.5x[b] |

NA: not applicable
[a]Drug concentration in the dry-coat cytokine release assay was approximated using the incubation volume (0.3 mL), and the human dose was calculated by multiplying the no-effect drug level by the plasma volume of 40 mL/kg
[b]Margin was calculated after normalization with differences in binding $EC_{50}$ values In summary, a PK/PD-based approach, focused on anti-tumor efficacy as the intended pharmacological effect, was successfully used to select and justify the FIH starting dose of the agonistic anti-OX40 antibody, OX40.21. The selected FIH starting dose (20 mg assuming a body weight of 80 kg) was supported by preclinical in vitro and in vivo toxicology data. The PK/PD-based strategy for FIH starting dose selection, together with in vitro and in vivo toxicology findings, reflects the intent of ensuring adequate safety while minimizing the number of patients with cancer receiving sub-therapeutic doses.

Example 15: Patient Characteristics and Treatment-Related Adverse Events in OX40.21 Monotherapy and OX40.21+Nivolumab Dose-Escalation Trial This Example summarizes the baseline demographics, prior therapy, and tumor types of, and adverse events in, patients undergoing OX40.21 monotherapy (n=20) Q2W and OX40.21+nivolumab combination therapy (n=39) Q2W in a dose-escalation trial. Patient characteristics are summarized in Table 9, and adverse events are summarized in Table 10.

TABLE 9

| | | OX40.21 monotherapy | OX40.21 + nivolumab |
|---|---|---|---|
| Median age (range), years | | 61(24-80) | 61(32-82) |
| Gender, n | Male/Female | 13/7 | 20/19 |
| ECOG ps, n | 0-1 | 19 | 38 |
| | Not reported | 1 | 1 |
| Race, n | White | 16 | 38 |
| | Black | 2 | 0 |
| | All Others | 2 | 1 |
| No. of prior therapies, n | 0 | 0 | 4 |
| | 1 | 9 | 9 |
| | 2 | 3 | 8 |
| | ≥3 | 8 | 18 |
| Prior immunotherapy, n | Prior anti-PD-1/PD-L1 | 6 | 12 |
| | Prior anti-CTLA-4 | 4 | 4 |
| | Both | 4 | 4 |
| Tumor type, n | CRC | 7 | 8 |
| | Melanoma | 4 | 6 |
| | Pancreatic Cancer | 4 | 3 |
| | Other[a] | 5 | 22 |

[a]Includes breast cancer, bladder cancer, cervical cancer, endometrial cancer, gastric cancer, HCC, NSCLC, ovarian cancer, prostate cancer, RCC, and SCCHN
CRC = colorectal cancer; CTLA-4 = cytotoxic T lymphocyte antigen-4; ECOG PS = Eastern Cooperative Oncology Group performance status; HCC = hepatocellular carcinoma; NSCLC = non-small cell lung cancer; PD-L1 = programmed death ligand 1; RCC = renal cell carcinoma; SCCHN = squamous cell cancer of the head and neck

TABLE 10

| | OX40.21 | OX40.21 + nivolumab 240 mg | | | | | |
|---|---|---|---|---|---|---|---|
| | All Mono n = 20 | 20 mg n = 7 | 40 mg n = 8 | 80 mg n = 8 | 160 mg n = 8 | 320 mg n = 8 | Total n = 39 |
| Any TRAE, n | 5[a] | 4 | 3 | 3 | 6 | 4 | 20 |
| Grade 1 or 2 TRAEs in ≥2 patients in total combination cohort, n | | | | | | | |
| Fatigue | 0 | 0 | 1 | 1 | 3 | 0 | 5 |
| Pyrexia | 1 | 0 | 1 | 2 | 0 | 2 | 5 |
| Arthralgia | 0 | 0 | 1 | 1 | 2 | 0 | 4 |
| Chills | 0 | 1 | 0 | 0 | 1 | 0 | 2 |
| Diarrhea | 1 | 1 | 0 | 0 | 1 | 0 | 2 |
| Hypothyroidism | 0 | 0 | 1 | 0 | 0 | 1 | 2 |
| Nausea | 1 | 0 | 0 | 0 | 1 | 1 | 2 |
| Any grade 3/4TRAE | 1[b] | 0 | 0 | 0 | 1[c] | 0 | 1[c] |

Figure 39:
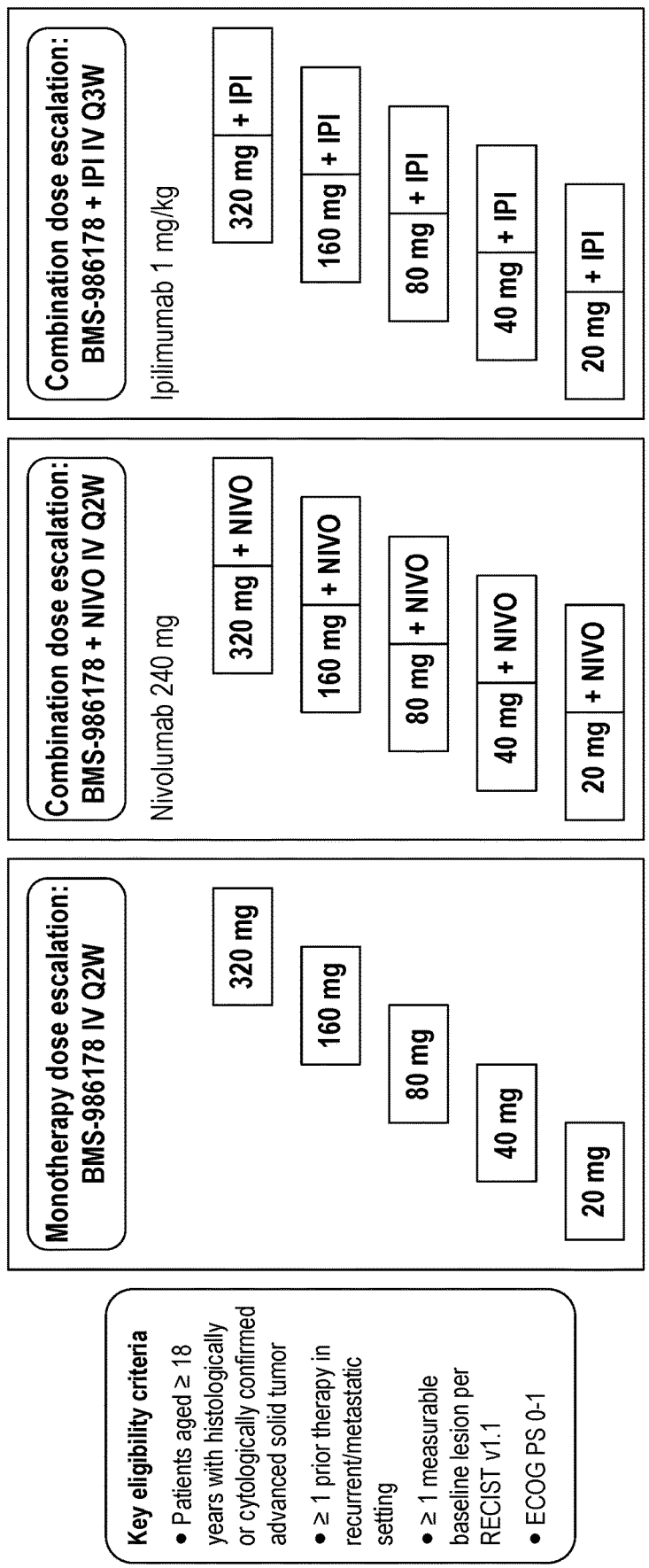
FIG. 39 shows the study design for the monotherapy dose escalation (BMS-986178 only) versus combination (BMS-986178 with either nivolumab or ipilimumab). DLT=dose-limiting toxicity; ECOG PS=Eastern Cooperative Oncology Group performance status; IV=intravenous; MTD=maximum tolerated; dose; Q2W=every 2 weeks; Q3W=every 3 weeks; RECIST=Response Evaluation Criteria in Solid Tumors; RP2D=recommended phase 2 dose.

One patient each experienced a serious adverse event,
[a]grade 2 pneumonitis (OX40.21 320 mg) and
[c]grade 3 pneumonitis, leading to discontinuation, which was considered a DLT;
[b]One patient experienced grade 3 fatigue.
TRAE: treatment-related adverse event The maximum-tolerated dose was not reached, and no treatment-related deaths occurred. The safety profile of OX40.21+nivolumab was similar to that of nivolumab monotherapy.
OX40 Receptor Modulation in a Phase 1/2a Study of the OX40 Costimulatory Agonist BMS-986178 f Nivolumab (NIVO) or Ipilimumab (IPI) in Patients with Advanced Solid Tumors Example 16: Pharmacokinetics of Monotherapy Compared to Combination Therapy The following Example follows the schematic of the study design as shown in FIG. 39. Humans were given a monotherapy dose of BMS-986178, a combination dose escalation of BMS-986178 and nivolumab (IV Q2W) at 240 mg, or a combination dose escalation of BMS-986178 and ipilimumab (IV Q3W) at 1 mg/kg. Patients who met the criteria in FIG. 39 were eligible for the study.

To assess the pharmacokinetics of monotherapy compared to combination therapy, patient blood samples were collected in the Cyto-Chex BCT (Streck). After red blood cell lysis, the cells were stained using fluorescently labeled antibodies specific for surface markers. After surface staining, the samples were fixed, permeabilized, and then stained with antibodies against intracellular markers. The stained samples were acquired on a Beckman Coulter CytoFlex S flow cytometer, and the resulting data were analyzed using FlowJo software.

In this study, 90 patients were treated (BMS-986178 monotherapy, n=20; BMS-986178+NIVO, n=38; BMS-986178+IPI, n=32). As shown in FIG. 40, PK of BMS-986178 alone or in combination with nivolumab or ipilimumab was linear for BMS-986178 doses of 20 to 320 mg. Thus, concentration-time profile of BMS-986178 was well described by a linear, 2-compartment, zero-order IV infusion model with first-order elimination.

Example 17: Whole-Blood OX40 Receptor Occupancy (RO) Assessment of Monotherapy and Combination (Agonist BMS-986178±Nivolumab (NIVO) or Ipilimumab (IPI)) Therapy To assess whole-blood OX40 receptor occupancy (RO) assessment, patient blood samples were incubated with a saturating dose of BMS-986178 to measure total OX40 expression or without BMS-986178 incubation to measure bound drug, followed by staining for surface markers C1D1, C1D8, C2D1, or C5D1 and flow cytometric analysis.

Figure 41:
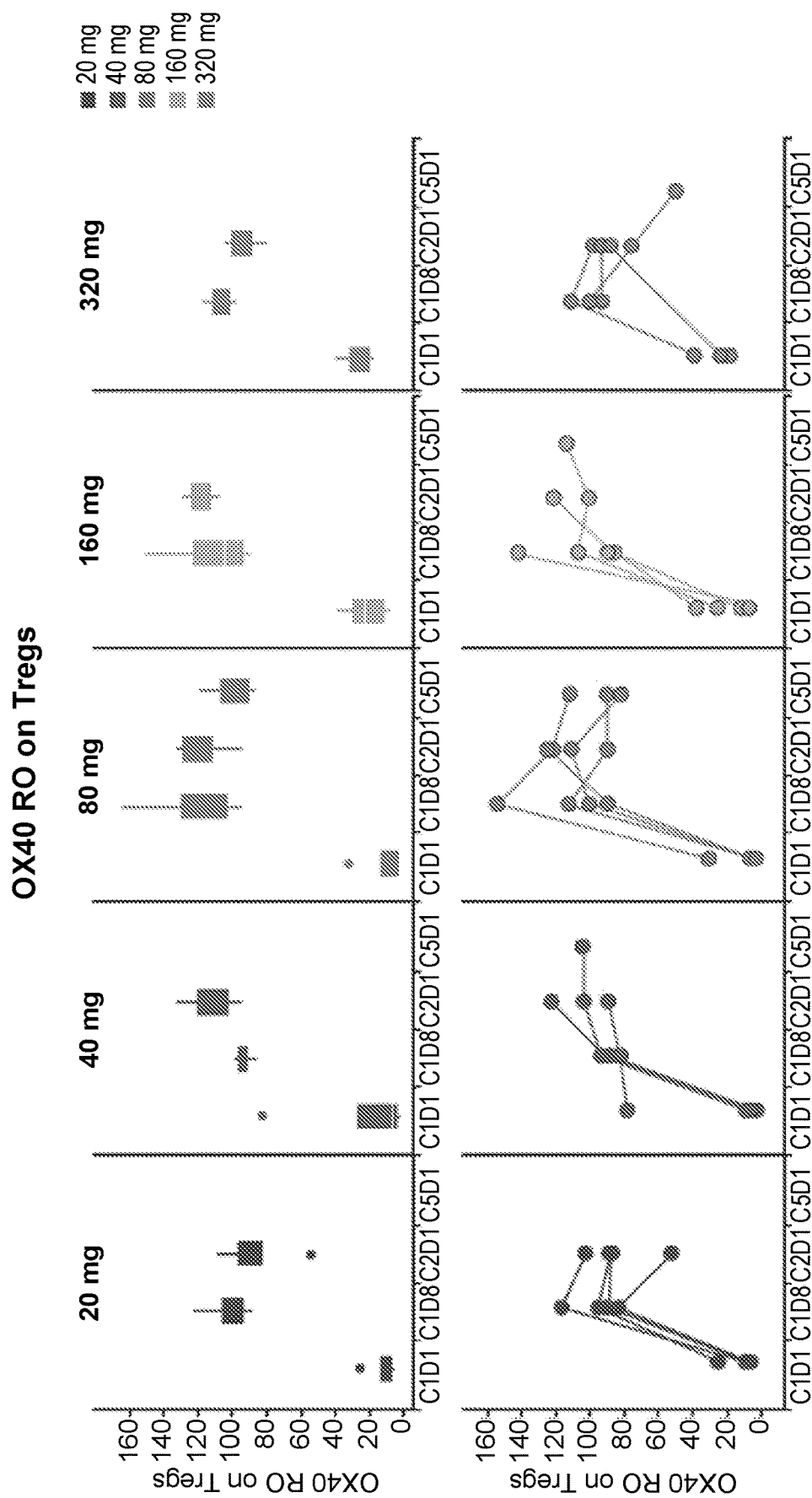
FIG. 41 shows the peripheral OX40 RO on peripheral Tregs using surface markers C1D1, C1D8, C2D1, or C5D1 after treatment with 20 mg, 40 mg, 80 mg, 160 mg or 320 mg of OX-40.21.

As shown in FIG. 41, peripheral OX40 RO on Tregs was approaching saturation in patients treated with BMS-986178 20 mg and was saturated at doses ≥40 mg.

Next, it was assessed whether there was downregulation of peripheral Tregs in patients treated with ≥40 mg BMS-986178. To test total OX40 in peripheral Tregs, an assay to measure total sOX40 in patient serum was developed and validated (fit for purpose) using the Meso Scale Discovery (MSD) platform. MSD Gold 96-well streptavidin plate was coated with a biotinylated capture antibody, followed by patient serum incubation. A ruthenylated detection antibody was used to detect the captured sOX40, and electrochemiluminescence was measured via the MSD SECTOR instrument.

Figure 42:
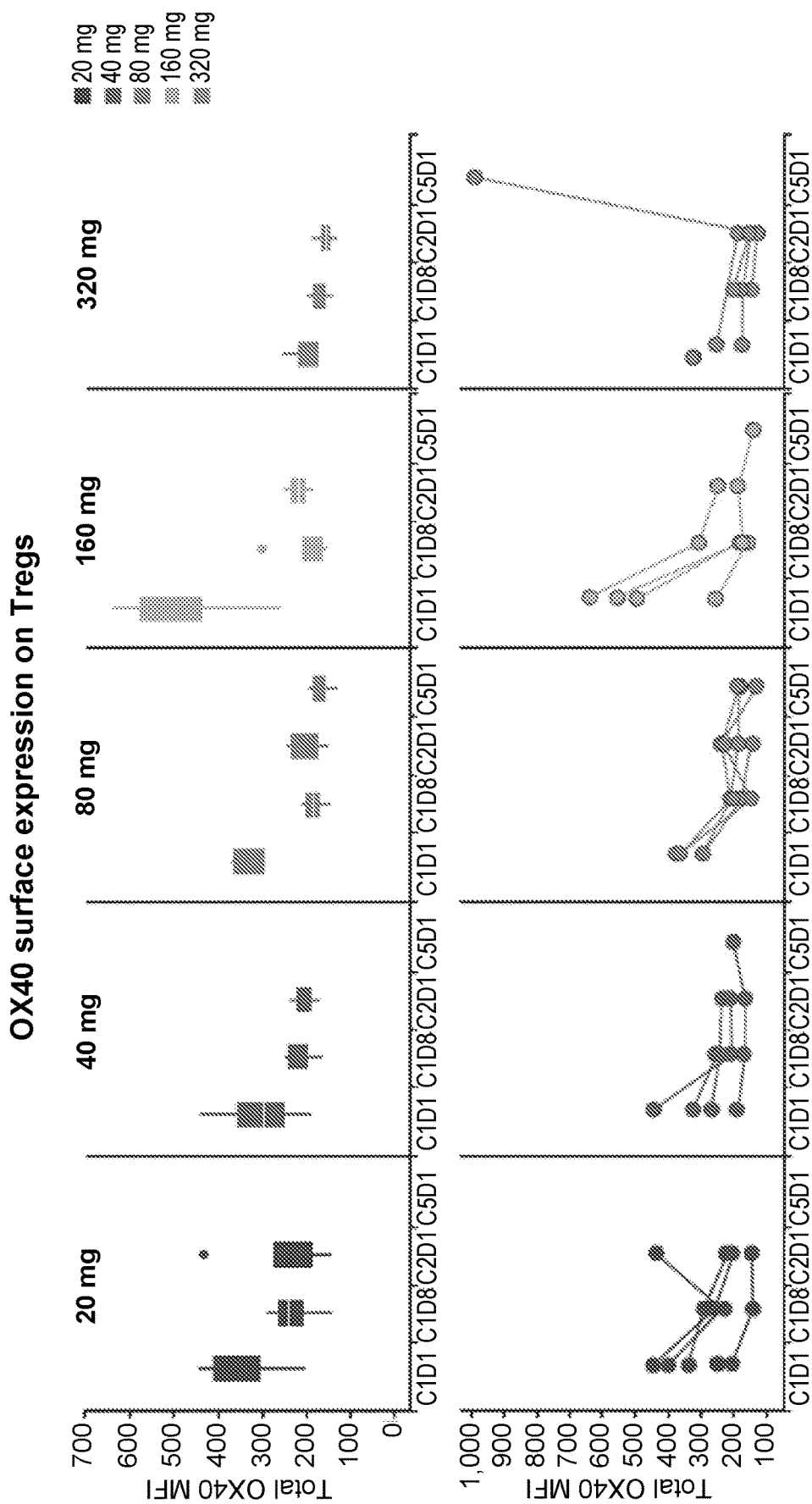
FIG. 42 is total OX40 expression as measured by mean fluorescence intensity on peripheral Tregs using surface markers C1D1, C1D8, C2D1, or C5D1 after treatment with 20 mg, 40 mg, 80 mg, 160 mg or 320 mg of OX-40.21.

As shown in FIG. 42, downregulation of OX40 expression on the surface of Tregs was observed in patients treated with ≥40 mg of BMS-986178, where RO approached saturation.

Figure 43A:
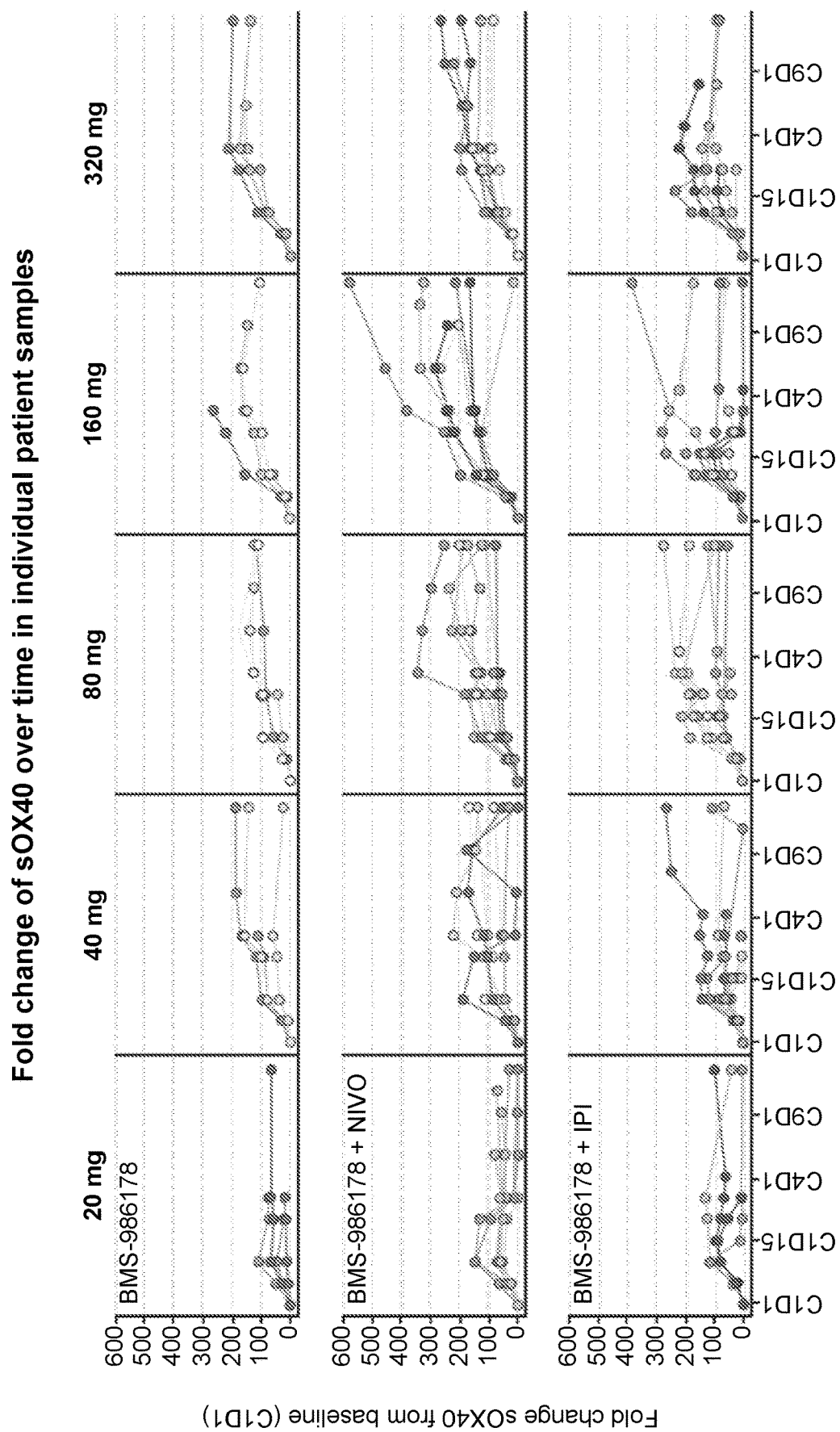
FIG. 43A shows fold change of sOX40 over time in individual patient samples at various doses.
Figure 43B:
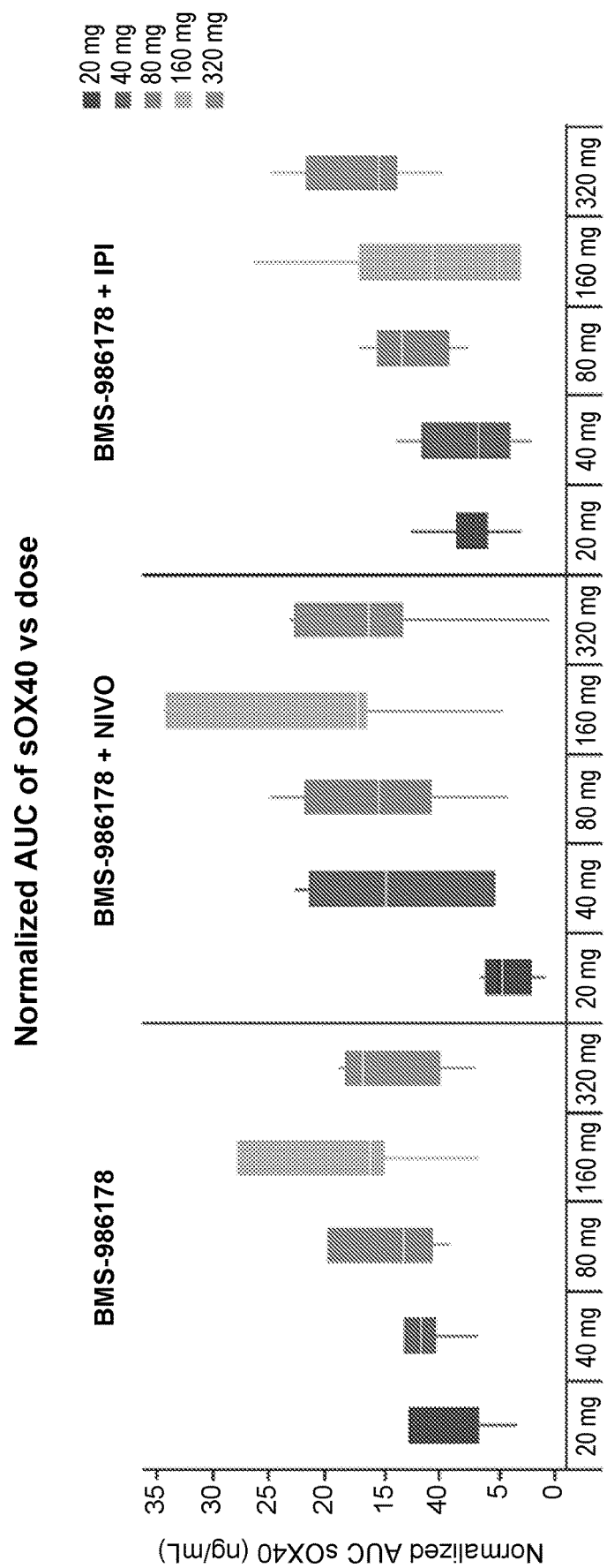
FIG. 43B shows the normalized AUC of sOX40 at various doses. Normalized AUC of sOX40 was calculated using (AUC0–$T_{last}/T_{last}$), which accounted for patients with different follow-up times; $AUC_{0-Tlast}$=area under the curve from time 0 to last follow-up; $T_{last}$=last follow-up time.

It was next determined whether this trend was also observed in individual patients treated with BMS-986178 monotherapy or with combination of BMS-986178 and nivolumab or ipilimumab. As shown in FIGS. 43A and 43B, sOX40, a marker of T-cell activation, showed time- and dose-dependent modulation in patients treated with BMS-986178±nivolumab or ipilimumab, confirming OX40 target engagement by BMS-986178. sOX40 levels in patients treated with ≥160 mg BMS-986178 became almost saturated, consistent with RO results (FIG. 42) and preclinical observations (data not shown).

Figure 44A:
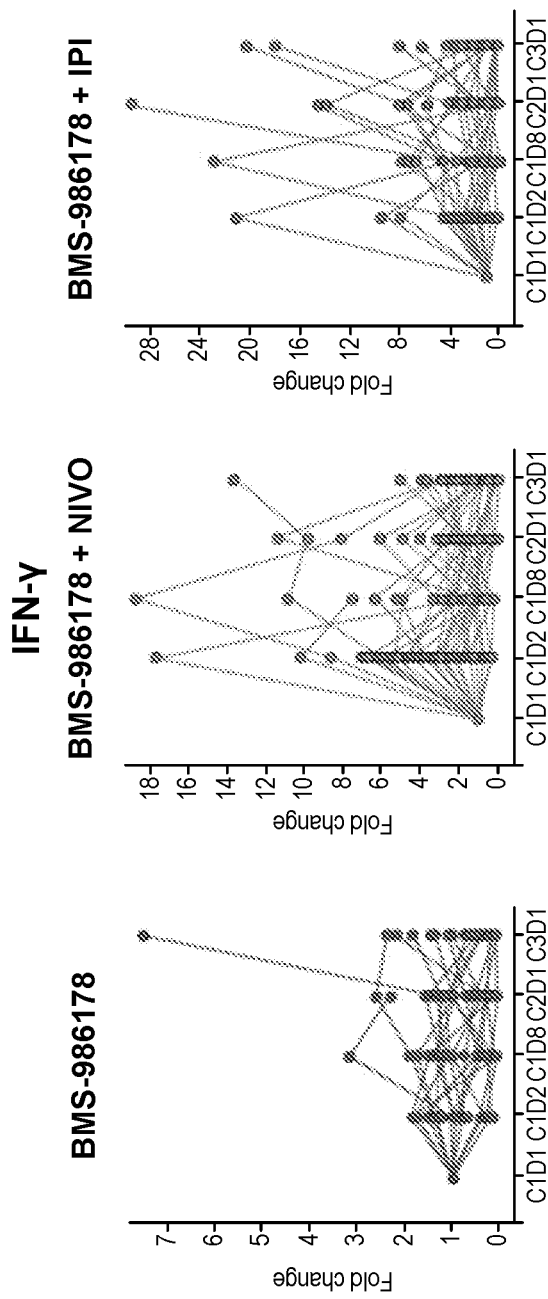
FIGS. 44A and 44B show BMS-986178±nivolumab or ipilimumab stimulated production of IFN-γ (FIG. 44A) and IP-10 (FIG. 44B).
Figure 44B:
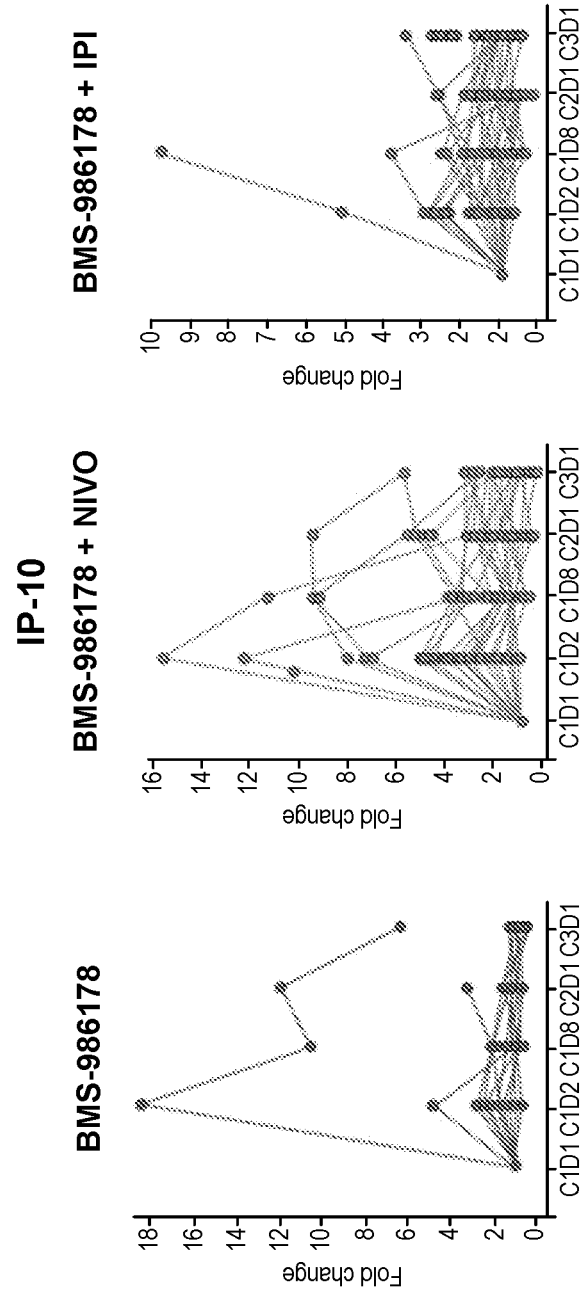

Example 18: Serum Cytokine Expression of Monotherapy and Combination (Agonist BMS-986178 f Nivolumab (NIVO) or Ipilimumab (IPI)) Therapy Interferon-gamma (IFN-γ) and IP-10 were measured in patients treated with BMS-986178 monotherapy and combination therapy. Briefly, IFN-γ and IP-10 in patient serum were measured using Luminex-based technology (customized multi-analyte profile [MAP] panel combining several human inflammatory MAP panels [Myriad RBM]). As shown in FIGS. 44A and 44B, BMS-986178±NIVO or IPI stimulated production of the TH1-associated cytokine IFN-γ (FIG. 44A) and the proinflammatory cytokine 10 kDa IFN-γ induced protein IP-10 (FIG. 44B), suggesting peripheral T-cell activation. Further, a greater number of patients who received BMS-986178+NIVO or IPI showed robust increases in IFN-γ and IP-10 production.

Figure 45A:
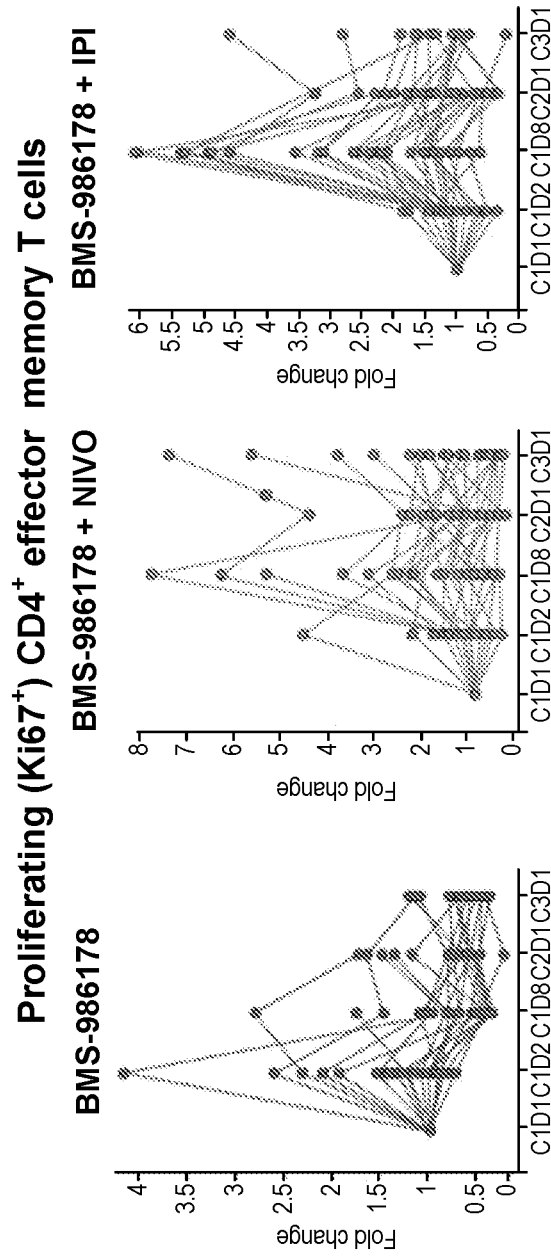
FIGS. 45A and 45B shows BMS-986178±nivolumab or ipilimumab increased level of proliferating (Ki67$^+$) CD4$^+$ (FIG. 45A) and CD8$^+$ (FIG. 45B) effector memory T cells.
Figure 45B:
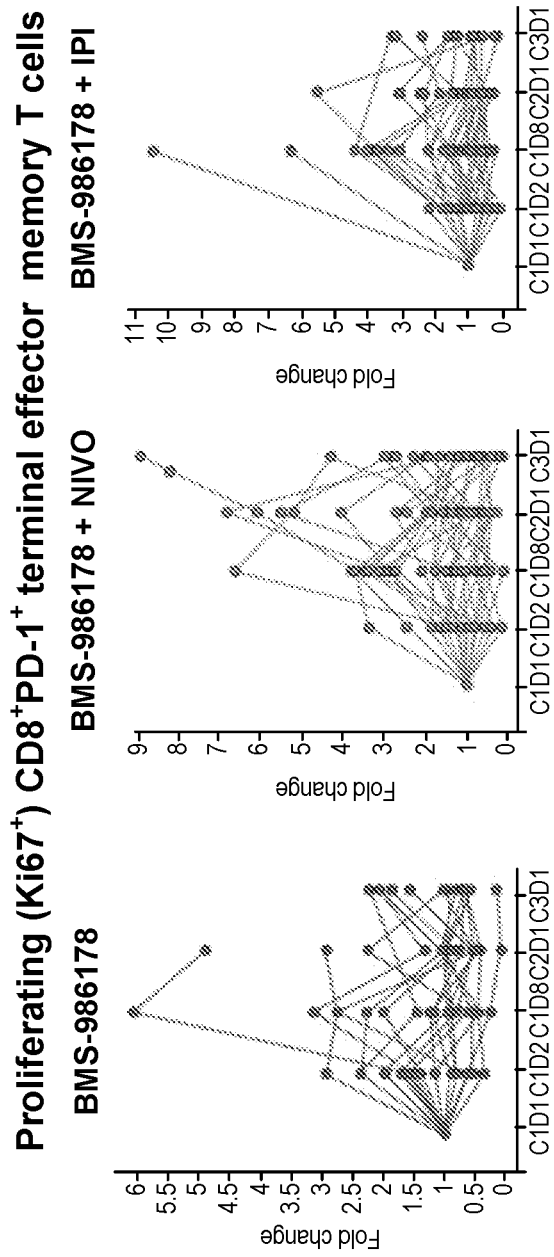

It was also observed that BMS-986178±NIVO or IPI increased level of proliferating (Ki67+) CD4+ and CD8+ effector memory T cells. As shown in FIGS. 45A and 45B, patients treated with BMS-986178±NIVO or IPI showed increased proliferating (Ki67+) CD4+ effector memory T cells (FIG. 45A) and CD8+PD-1+ terminal effector memory T cells (FIG. 45B) Thus, BMS-986178+NIVO or IPI showed a more profound increase in proliferating CD4+ and CD8+ effector memory T cells in a greater number of patients than did BMS-986178 alone.

Figure 37:
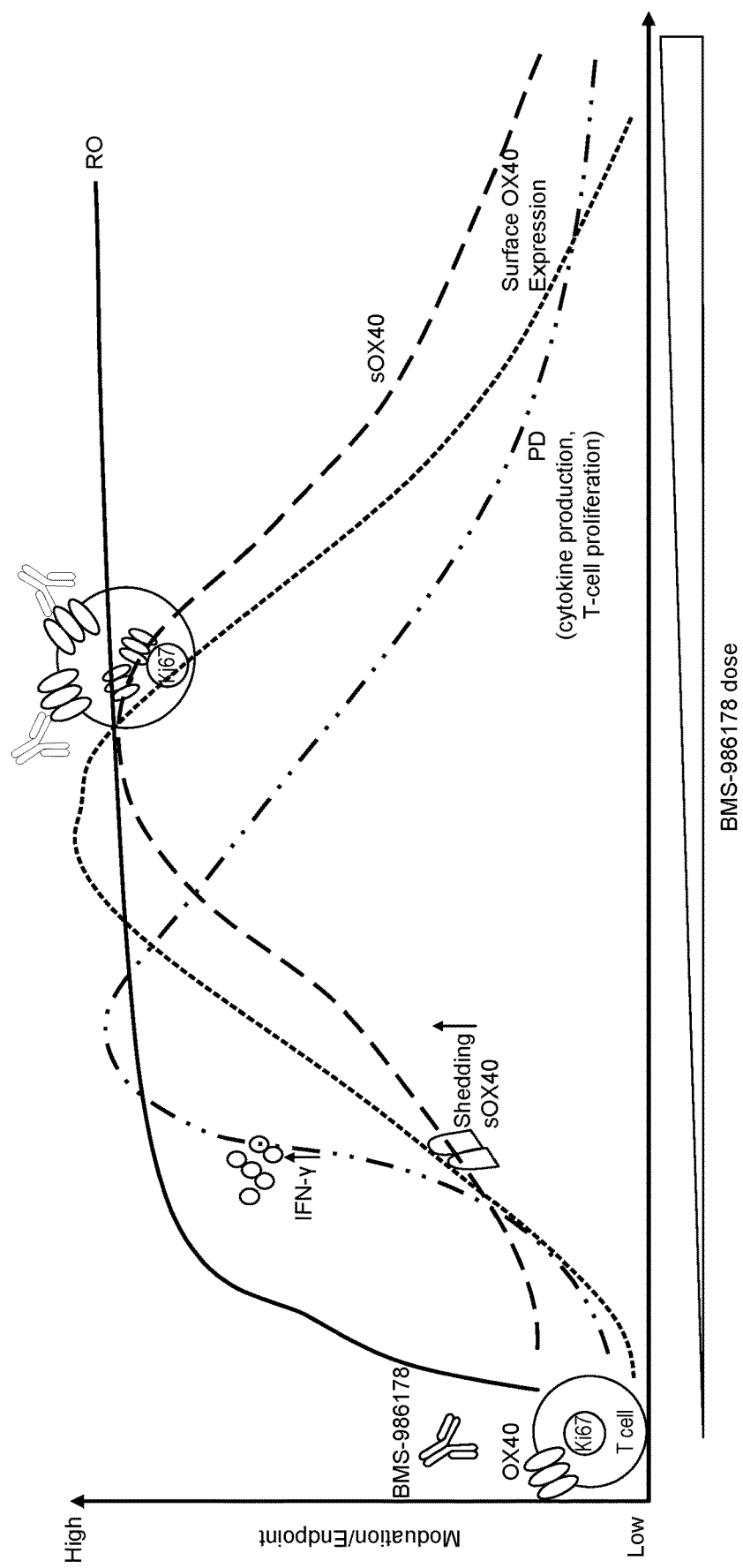
FIG. 37 is a schematic model of the relationship between BMS-986178 (BMS-986178 surrogate mouse antibody) dose, OX40 RO, OX40 expression, and PD modulation.

Based on the data presented above, without being limited to a particular mechanism, a schematic model of the relationship between BMS-986178 dose, OX40 RO, OX40 expression, and PD modulation is presented in FIG. 37.

Example 19: Development and Validation of Human Total Soluble OX40 Biomarker Assay As described in Example 17, an assay to measure total sOX40 in patient serum was developed and validated using the Meso Scale Discovery (MSD) platform. The assay was validated using fit-for-purpose biomarker validation, including accuracy and precision, dilution linearity/parallelism, specificity (matrix effects and drug interference), stability, and selectivity, was conducted.

Figure 46A:
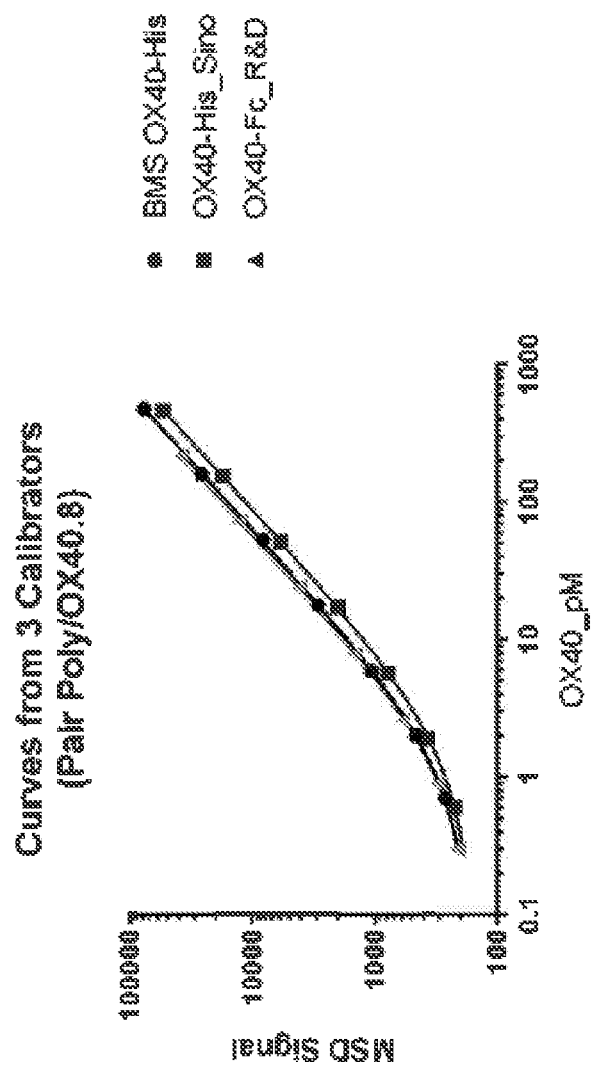
FIGS. 46A to 46H show the validation results of the human total soluble OX40 biomarker assay that was developed to measure total soluble OX40 levels in human serum.
Figure 46B:
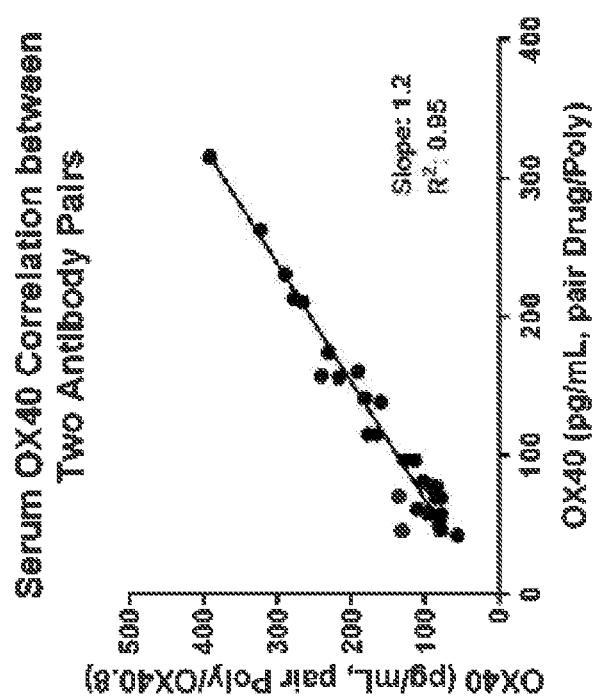
Figure 46C:
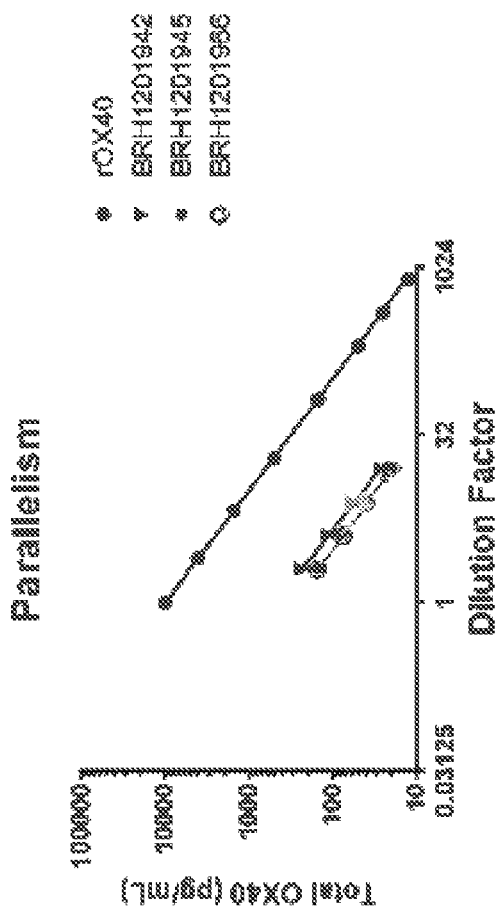
Figure 46D:
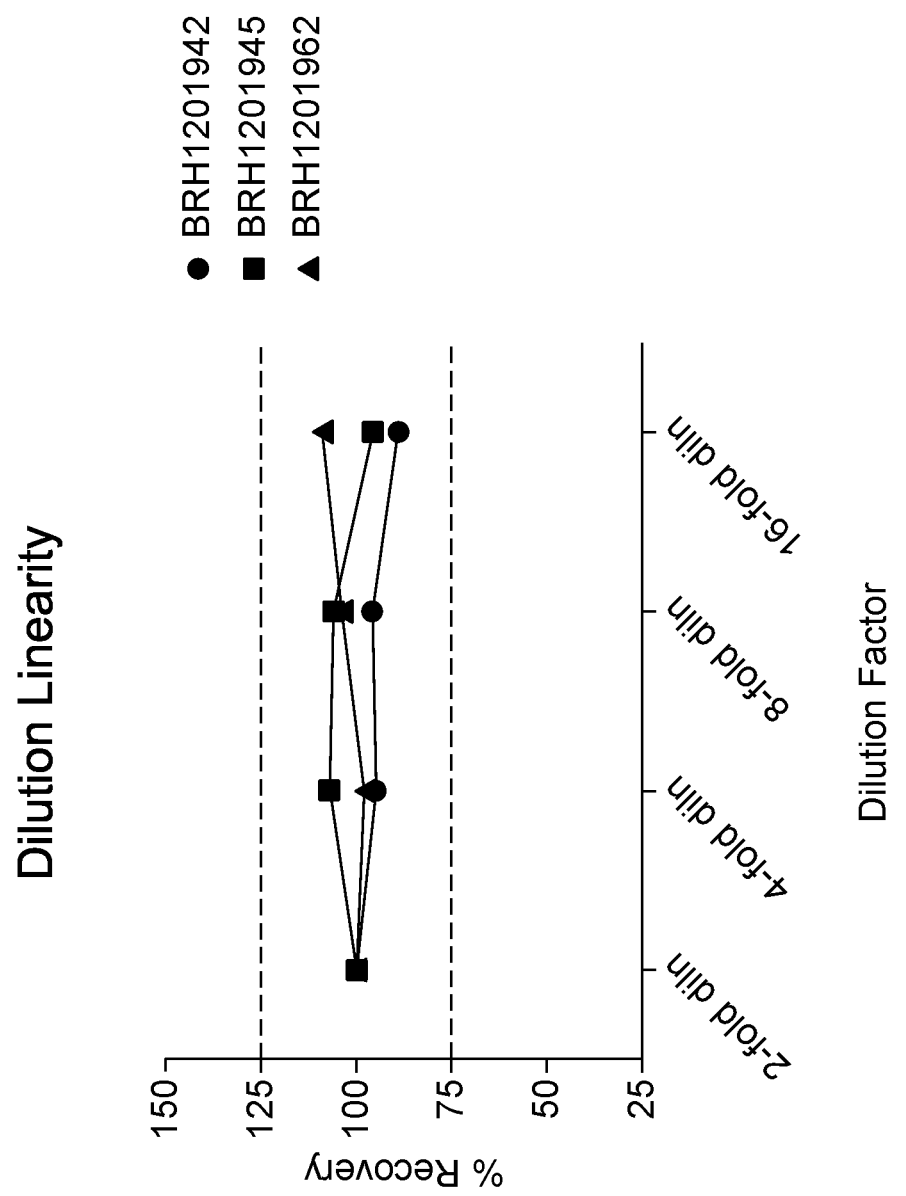
Figure 46E:
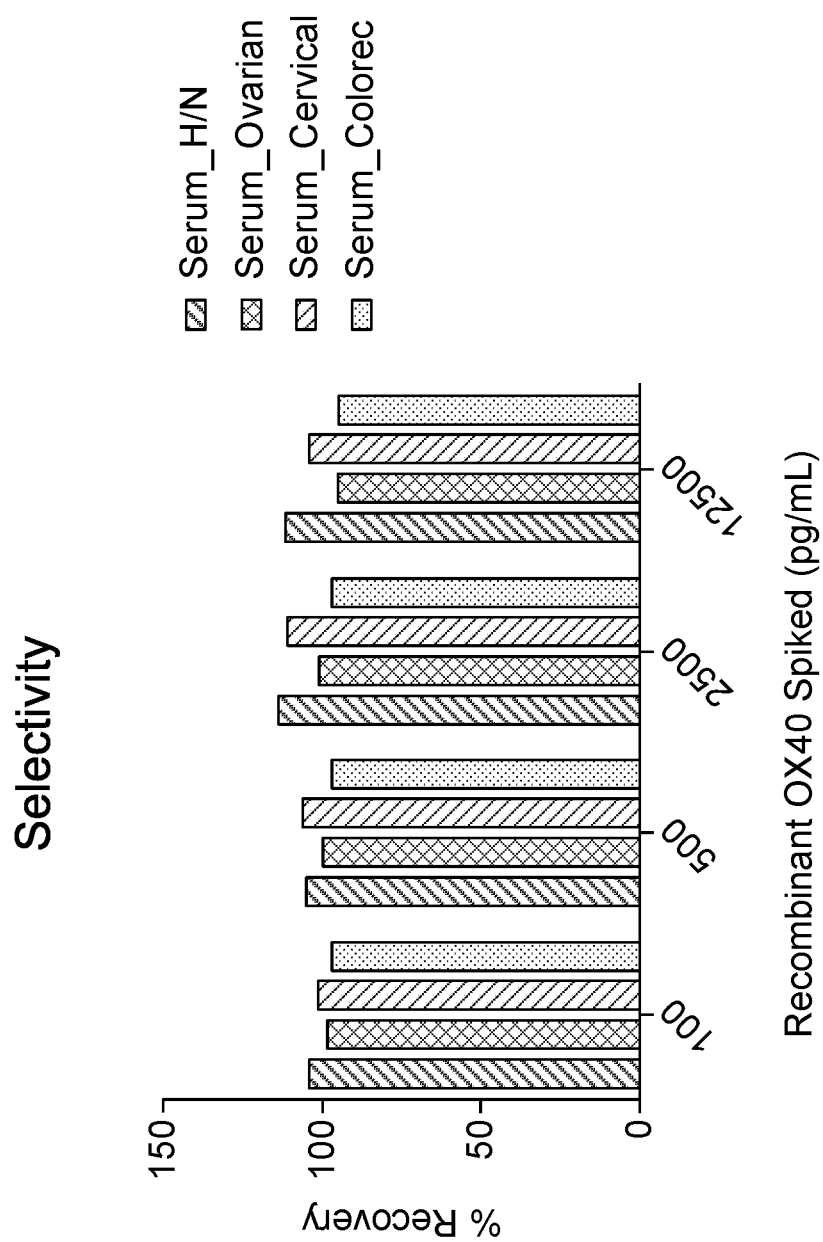
Figure 46F:
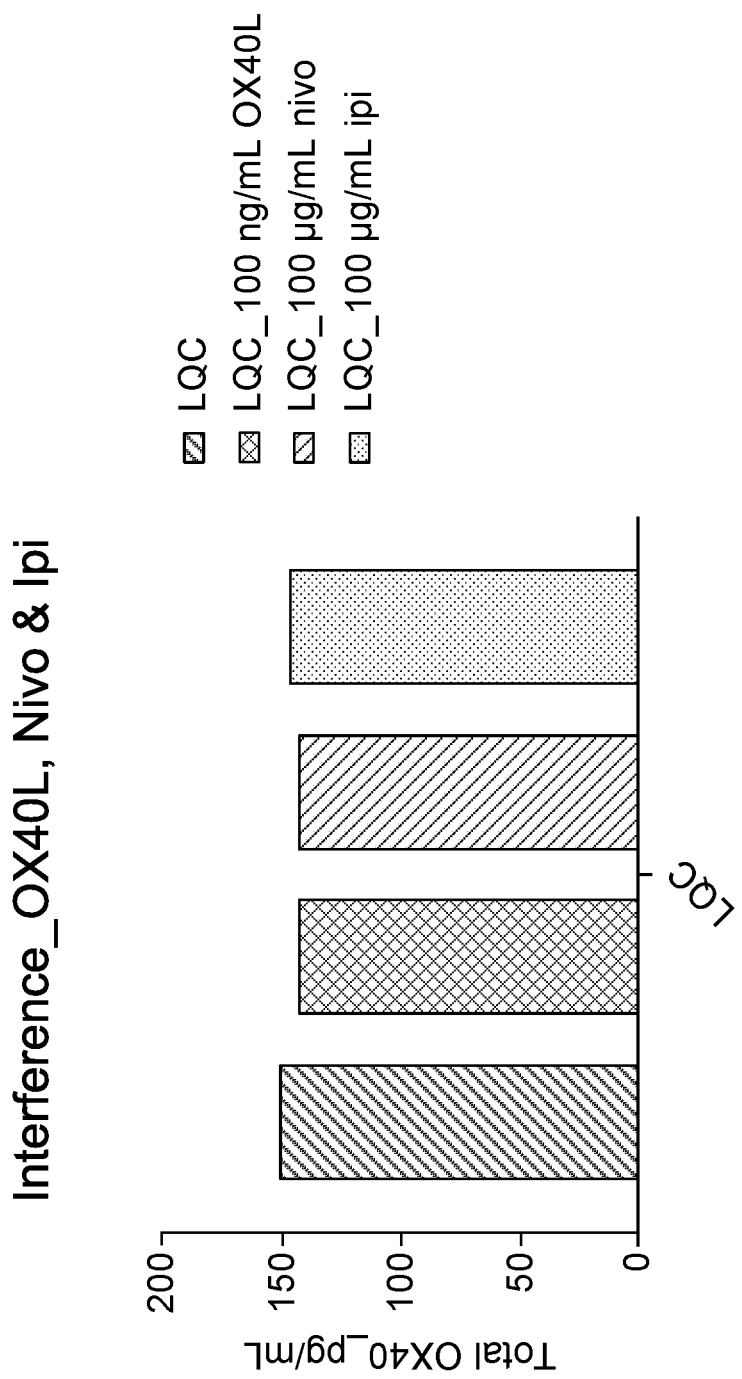
Figure 46G:
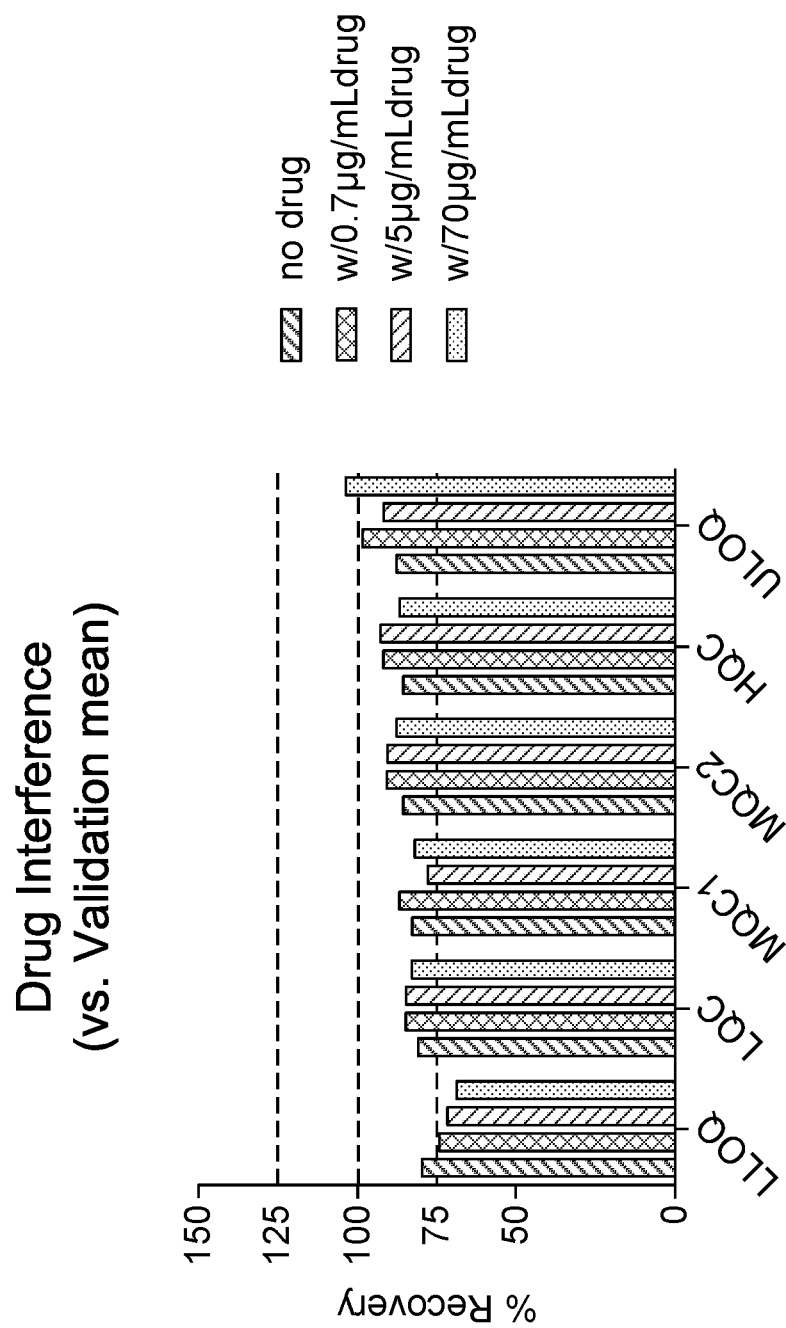
Figure 46H:
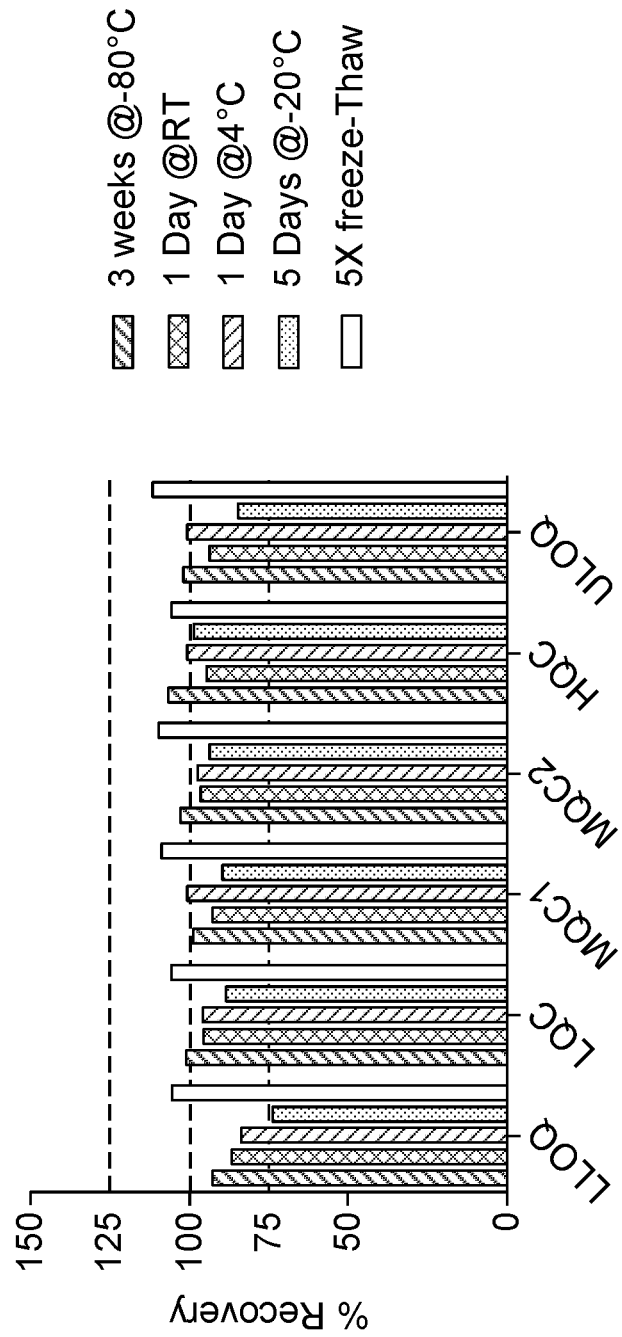
Figure 48:
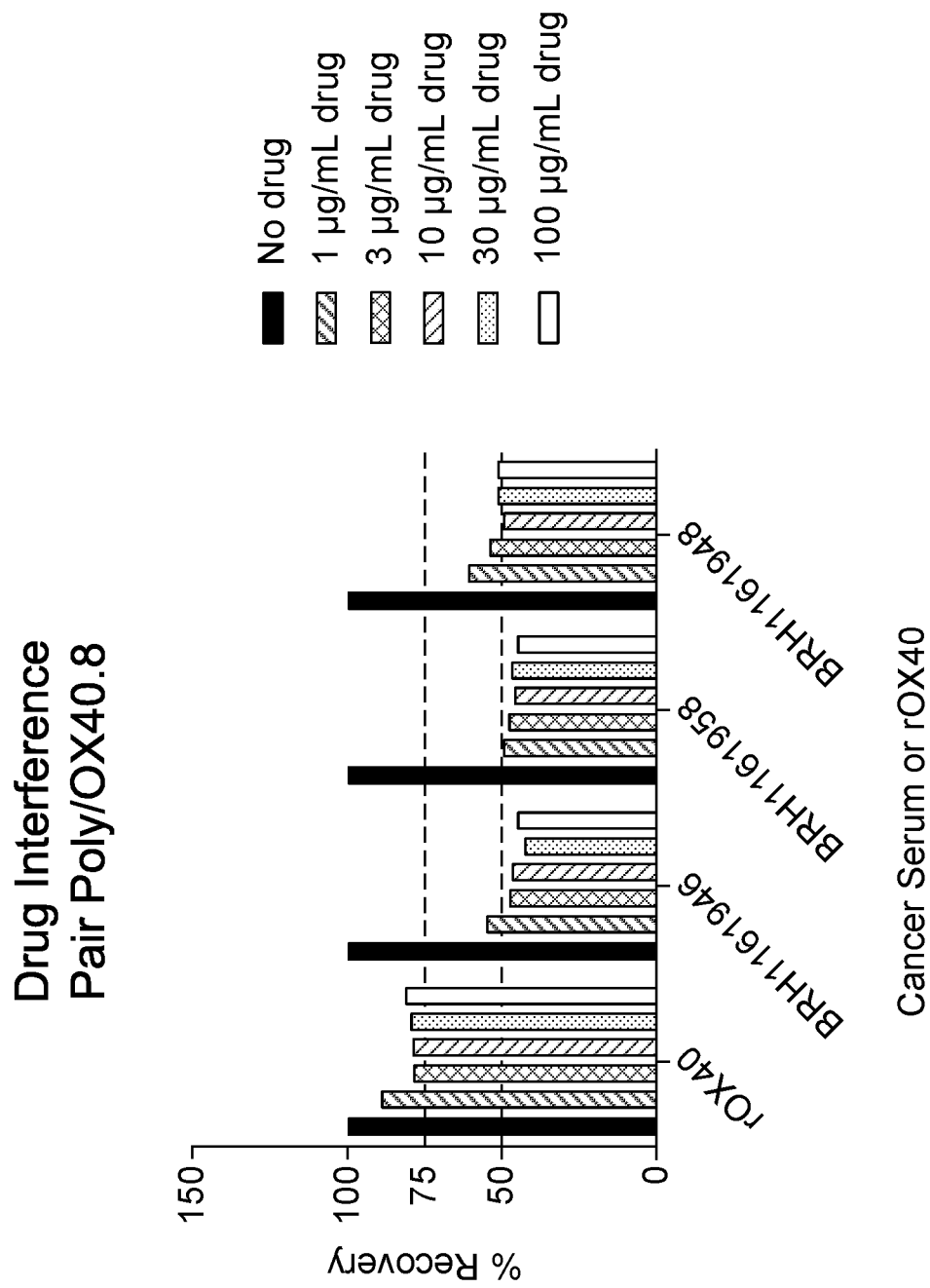
FIG. 48 shows the drug interference data for OX40.8 antibody.

The validation results are provided in FIGS. 46A to 46II and Tables 11-12. As shown, the assay range of human serum total sOX40 was 25-20,000 pg/mL. Accuracy of 7 standard curve points (n=20) were within 98-103% and had a CV≤8%. QC performance was within acceptable limits: CV was below 14% for LQC, MQC, HQC, and ULOQ (with 26% CV at LLOQ). Tables 11 and 12. The assay calibrator demonstrated parallelism between BMS-986178 and the commercial calibrators (i.e., OX40-His_Sino and OX40-Fc_R&D). FIG. 46A. There was also good serum OX40 correlation between two different antibody pairs. FIG. 46B. Dilution linearity/parallelism, specificity, stability, and selectivity all recovered within ±25% of the expected concentrations. FIG. 46C to 46E. Storage and freeze-thaw stabilities of OX40 were also within performance expectations. FIG. H. Lastly, minimal interference from anti-OX40 antibody, OX40L fusion protein, nivolumab, and ipilimumab was observed. FIGS. 46F, 46G, and 48. These results demonstrate the high precision, sensitivity, and suitability of the assay for analysis of clinical samples.

TABLE 11

Summary of Calibration Curve Validation Data

| Conc. in Serum (pg/mL) | 20000 | 8000 | 3000 | 1000 | 300 | 100 | 50 | 25 |
|---|---|---|---|---|---|---|---|---|
| Conc. on Plate (pg/mL) | 10000 | 4000 | 1500 | 500 | 150 | 50 | 25 | 12.5 |

Back-Calculated OX40 (pg/mL)

| n | 20 | 20 | 20 | 20 | 20 | 20 | 20 | 20 |
|---|---|---|---|---|---|---|---|---|
| Mean (pg/mL) | 10180 | 4008 | 1488 | 496 | 150 | 51 | 25 | 12.3 |
| % CV | 8 | 2 | 3 | 2 | 2 | 3 | 5 | 5 |
| % Accuracy | 102 | 100 | 99 | 99 | 100 | 103 | 100 | 98 |

TABLE 12

QC performance.

| | LLOQ_A | LLOQ | LQC | MQC1 | MQC2 | HQC | ULOQ |
|---|---|---|---|---|---|---|---|
| n | 24 | 40 | 40 | 40 | 40 | 40 | 40 |
| Mean (pg/mL) | 31 | 61 | 126 | 841 | 2462 | 15378 | 20158 |
| % CV_Intra-Assay | 14 | 7 | 7 | 5 | 5 | 5 | 6 |
| % CV_Inter-Assay | 24 | 13 | 9 | 9 | 9 | 8 | 8 |
| % CV | 26 | 14 | 11 | 10 | 10 | 9 | 10 |
| Mean ± 2 Stdev | 15-48 | 43-78 | 99-153 | 668-1013 | 1963-2960 | 12527-18230 | 16318-23998 |

Figure 47:
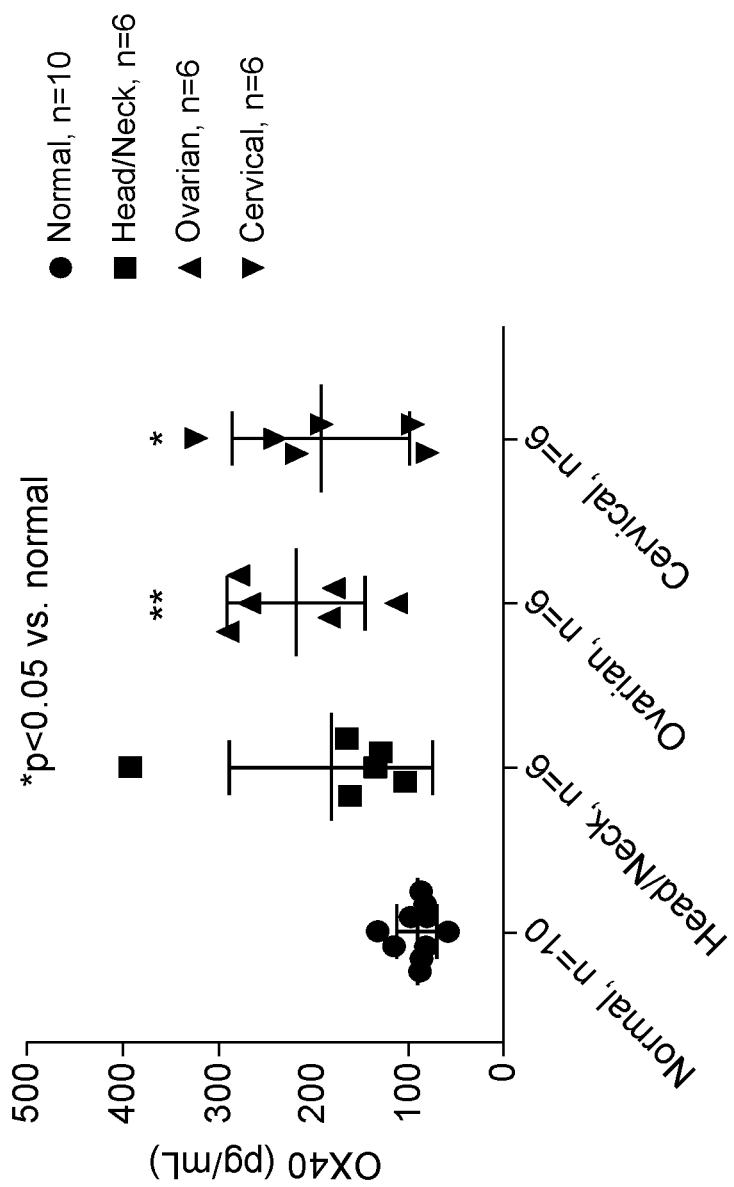
FIG. 47 shows soluble OX40 levels, as measured using the human total soluble OX40 biomarker assay, in normal healthy individuals and in three different cancer subjects (head/neck, ovarian, and cervical).

Once validated, the assay was used to measure serum sOX40 levels in normal healthy volunteers and in cancer subjects. As shown in FIG. 47, sOX40 levels were significantly elevated in cancer patients (head/neck, ovarian, or cervical) compared to normal healthy individuals. This result supports the use of an anti-OX40 antibody (e.g., BMS-986178), alone or in combination with other therapeutic agents, such as nivolumab and ipilimumab, to treat cancer.

TABLE 13

Summary of sequences

| SEQ ID | Description | Sequence |
|---|---|---|
| 1 | Human OX40 precursor | MCVGARRLGRGPCAALLLLGLGLSTVTGLHCVGDTYPSNDRCCHECR PGNGMVSRCSRSQNTVCRPCGPGFYNDVVSSKPCKPCTWCNLRSGSE RKQLCTATQDTVCRCRAGTQPLDSYKPGVDCAPCPPGHFSPGDNQAC KPWTNCTLAGKHTLQPASNSSDAICEDRDPPATQPQETQGPPARPIT VQPTEAWPRTSQGPSTRPVEVPGGRAVAAILGLGLVLGLLGPLAILL ALYLLRRDQRLPPDAHKPPGGGSFRTPIQEEQADAHSTLAKI |
| 2 | Extracellular domain of mature human OX40 | LHCVGDTYPSNDRCCHECRPGNGMVSRCSRSQNTVCRPCGPGFYNDV VSSKPCKPCTWCNLRSGSERKQLCTATQDTVCRCRAGTQPLDSYKPG VDCAPCPPGHFSPGDNQACKPWTNCTLAGKHTLQPASNSSDAICEDR DPPATQPQETQGPPARPITVQPTEAWPRTSQGPSTRPVEVPGGRAVA A |
| 3 | Cynomolgus OX40 | MCVGARRLGRGPCAALLLLGLGLSTTAKLHCVGDTYPSNDRCCQECR PGNGMVSRCNRSQNTVCRPCGPGFYNDVVSAKPCKACTWCNLRSGSE RKQPCTATQDTVCRCRAGTQPLDSYKPGVDCAPCPPGHFSPGDNQAC KPWTNCTLAGKHTLQPASNSSDAICEDRDPPPTQPQETQGPPARPTT VQPTEAWPRTSQRPSTRPVEVPRGPAVAAILGLGLALGLLGPLAMLL ALLLLRRDQRLPPDAPKAPGGGSFRTPIQEEQADAHSALAKI |
| 4 | Human OX40-L | MERVQPLEEN VGNAARPRFE RNKLLLAMSV IQGLGLLLCF TYICLHFSTL QVSHRYPRIQ SIKVQFTEYK KEKGFILTSQ KEDEIMKVQN NSVIINCDGF YLISLRGYFS QEVNISLHYQ KDEEPLFQLK KVRSVNSLMV ASLTYKDKVY LNVTTDNTSL DDFHVNGGEL ILIHQNPGEF CVL* |
| 5 | OX40.21 VHCDR1 | SYAMY |
| 6 | OX40.21 VHCDR2 | AIDTDAGTFYADSVRG |
| 7 | OX40.21 VHCDR3 | LGEGYFFDY |
| 8 | OX40.21 VLCDR1 | RASQSVSSYLA |
| 9 | OX40.21 VLCDR2 | DASNRAT |
| 10 | OX40.21 VLCDR3 | QQRSNWPPT |
| 11 | OX40.21 VH | EVQLVQSGGGLVQPGGSLRLSCAGSGFTFSSYAMYWVRQAPGKGLEW VSAIDTDAGTFYADSVRGRFTISRDNAKNSLYLQMNSLRAEDTAVYF CARLGEGYFFDYWGQGTLVTVSS |
| 12 | OX40.21 VL | EIVLTQSPATLSLSPGERATLSCRASQSVSSYLAWYQQKPGQAPRLL IYDASNRATGIPARFSGSGSGTDFTLTISSLEPEDFAVYYCQQRSNW PPTFGGGTKVEIK |
| 13 | OX40.21 HC | EVQLVQSGGGLVQPGGSLRLSCAGSGFTFSSYAMYWVRQAPGKGLEW VSAIDTDAGTFYADSVRGRFTISRDNAKNSLYLQMNSLRAEDTAVYF CARLGEGYFFDYWGQGTLVTVSSASTKGPSVFPLAPSSKSTSGGTAA LGCLVKDYFPEPVTVSWNSGALTSGVHTFPAVLQSSGLYSLSSVVTV PSSSLGTQTYICNVNHKPSNTKVDKRVEPKSCDKTHTCPPCPAPELL GGPSVFLFPPKPKDTLMISRTPEVTCVVVDVSHEDPEVKFNWYVDGV EVHNAKTKPREEQYNSTYRVVSVLTVLHQDWLNGKEYKCKVSNKALP APIEKTISKAKGQPREPQVYTLPPSREEMTKNQVSLTCLVKGFYPSD IAVEWESNGQPENNYKTTPPVLDSDGSFFLYSKLTVDKSRWQQGNVF SCSVMHEALHNHYTQKSLSLSPG |
| 14 | OX40.21 LC | EIVLTQSPATLSLSPGERATLSCRASQSVSSYLAWYQQKPGQAPRLL IYDASNRATGIPARFSGSGSGTDFTLTISSLEPEDFAVYYCQQRSNW PPTFGGGTKVEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC |
| 15 | OX40 polypeptide bound by OX40.21 | DVVSSKPCKPCTWCNLR |
| 16 | Heavy chain - nivolumab | QVQLVESGGGVVQPGRSLRLDCKASGITFSNSGMHWVRQAPGKGLEW VAVIWYDGSKRYYADSVKGRFTISRDNSKNTLFLQMNSLRAEDTAVY YCATNDDYWGQGTLVTVSSASTKGPSVFPLAPCSRSTSESTAALGCL VKDYFPEPVTVSWNSGALTSGVHTFPAVLQSSGLYSLSSVVTVPSSS LGTKTYTCNVDHKPSNTKVDKRVESKYGPPCPPCPAPEFLGGPSVFL FPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTI SKAKGQPREPQVYTLPPSQEEMTKNQVSLTCLVKGFYPSDIAVEWES |

TABLE 13-continued

Summary of sequences

| SEQ ID | Description | Sequence |
|---|---|---|
| | | NGQPENNYKTTPPVLDSDGSFFLYSRLTVDKSRWQEGNVFSCSVMHE ALHNHYTQKSLSLSLGK |
| 17 | Light chain - nivolumab | EIVLTQSPATLSLSPGERATLSCRASQSVSSYLAWYQQKPGQAPRLL IYDASNRATGIPARFSGSGSGTDFTLTISSLEPEDFAVYYCQQSSNW PRTFGQGTKVEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC |
| 18 | Heavy chain variable region - nivolumab | QVQLVESGGGVVQPGRSLRLDCKASGITFSNSGMHWVRQAPGKGLEW VAVIWYDGSKRYYADSVKGRFTISRDNSKNTLFLQMNSLRAEDTAVY YCATNDDYWGQGTLVTVSS |
| 19 | Light chain variable region - nivolumab | EIVLTQSPATLSLSPGERATLSCRASQSVSSYLAWYQQKPGQAPRLL IYDASNRATGIPARFSGSGSGTDFTLTISSLEPEDFAVYYCQQSSNW PRTFGQGTKVEIK |
| 20 | HCDR1 - nivolumab | NSGMH |
| 21 | HCDR2 - nivolumab | VIWYDGSKRYYADSVKG |
| 22 | HCDR3 - nivolumab | NDDY |
| 23 | LCDR1 - nivolumab | RASQSVSSYLA |
| 24 | LCDR2 - nivolumab | DASNRAT |
| 25 | LCDR3 - nivolumab | QQSSNWPRT |
| 26 | Heavy chain variable region - ipilimumab (from WO01/014424) | QVQLVESGGGVVQPGRSLRLSCAASGFTFSSYTMHWVRQAPGKGLEW VTFISYDGNNKYYADSVKGRFTISRDNSKNTLYLQMNSLRAEDTAIY YCARTGWLGPFDYWGQGTLVTVSS |
| 27 | Light chain variable region - ipilimumab (from WO01/014424) | EIVLTQSPGTLSLSPGERATLSCRASQSVGSSYLAWYQQKPGQAPRL LIYGAFSRATGIPDRFSGSGSGTDFTLTISRLEPEDFAVYYCQQYGS SPWTFGQGTKVEIK |
| 28 | HCDR1 - ipilimumab (from WO01/014424) | SYTMH |
| 29 | HCDR2 - ipilimumab (from WO01/014424) | FISYDGNNKYYADSVKG |
| 30 | HCDR3 - ipilimumab (from WO01/014424) | TGWLGPFDY |
| 31 | LCDR1 - ipilimumab (from WO01/014424) | RASQSVGSSYLA |
| 32 | LCDR2 - ipilimumab (from WO01/014424) | GAFSRAT |
| 33 | LCDR3 - ipilimumab (from WO01/014424) | QQYGSSPWT |

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. A method of treating a cancer in a subject in need thereof, comprising administering to the subject an agonistic antibody that specifically binds to OX40 ("anti-OX40 antibody"), wherein the anti-OX40 antibody is administered at a dose and/or frequency that is sufficient to achieve and/or maintain an OX-40 receptor occupancy of 20% to 80% in the subject for 7 days after the administration of the anti-OX40 antibody.

2. The method of claim 1, wherein the cancer is selected from the group consisting of: a bladder cancer, a breast cancer, an uterine/cervical cancer, an ovarian cancer, a prostate cancer, a testicular cancer, an esophageal cancer, a gastrointestinal cancer, a pancreatic cancer, a colorectal cancer, a colon cancer, a kidney cancer, a head and neck cancer, a lung cancer, a stomach cancer, a germ cell cancer, a bone cancer, a liver cancer, a thyroid cancer, a skin cancer, a neoplasm of the central nervous system, a lymphoma, a leukemia, a myeloma, a sarcoma, a non-small cell lung cancer, and a virus-related cancer.

3. The method of claim 1, further comprising administering one or more additional therapies selected from an anti-PD1 antibody, an anti-LAG-3 antibody, an anti-CTLA-4 antibody, an anti-PD-L1 antibody, an anti-TGFβ antibody, or combinations thereof.

4. The method of claim 3, wherein the one or more additional therapies comprises an anti-PD1 antibody.

5. The method of claim 3, wherein the agonistic antibody is administered (i) before administration of the one or more additional therapies, (ii) after administration of the one or more additional therapies, or (iii) concurrently with the one or more additional therapies.

6. The method of claim 3, wherein the one or more additional therapies are administered at a fixed frequency.

7. The method of claim 4, comprising at least one administration cycle of a combination of the anti-OX40 antibody and the anti-PD1 antibody, wherein each of the at least one administration cycle is a period of twelve weeks, and wherein each of the at least one administration cycle comprises one administration of the anti-OX40 antibody at a dose of 20, 40, or 80 mg and three administrations of the anti-PD-1 antibody, wherein each administration of the anti-PD-1 antibody is at a dose of 480 mg.

8. The method of claim 7, wherein the anti-PD-1 and anti-OX40 antibodies are formulated for intravenous administration.

9. The method of claim 7, wherein the anti-PD-1 and anti-OX40 antibodies are formulated together or separately.

10. The method of claim 7, wherein the anti-OX40 antibody is administered (i) prior to administration of the anti-PD-1 antibody, (ii) after administration of the anti-PD-1 antibody, or (iii) concurrently with the anti-PD-1 antibody.

11. The method of claim 7, consisting of up to 9 administration cycles.

12. The method of claim 7, wherein the anti-OX40 antibody is administered on Day 1 of each of the at least one administration cycle.

13. The method of claim 7, wherein the anti-PD-1 antibody is administered on Days 1, 29, and 57 of each of the at least one administration cycle.

14. The method of claim 7, wherein the anti-OX40 antibody comprises
   (a) a heavy chain variable region CDR1 comprising the sequence set forth in SEQ ID NO: 5;
   (b) a heavy chain variable region CDR2 comprising the sequence set forth in SEQ ID NO: 6;
   (c) a heavy chain variable region CDR3 comprising the sequence set forth in SEQ ID NO: 7;
   (d) a light chain variable region CDR1 comprising the sequence set forth in SEQ ID NO: 8;
   (e) a light chain variable region CDR2 comprising the sequence set forth in SEQ ID NO: 9; and
   a light chain variable region CDR3 comprising the sequence set forth in SEQ ID NO: 10.

15. The method of claim 7, wherein the anti-PD-1 antibody comprises (a) a heavy chain variable region CDR1 comprising the sequence set forth in SEQ ID NO: 20;
   (b) a heavy chain variable region CDR2 comprising the sequence set forth in SEQ ID NO: 21;
   (c) a heavy chain variable region CDR3 comprising the sequence set forth in SEQ ID NO: 22;
   (d) a light chain variable region CDR1 comprising the sequence set forth in SEQ ID NO: 23;
   (e) a light chain variable region CDR2 comprising the sequence set forth in SEQ ID NO: 24; and
   a light chain variable region CDR3 comprising the sequence set forth in SEQ ID NO: 25.

16. A method of reducing or depleting the number of regulatory T cells in a tumor of a subject with a cancer, comprising administering to the subject an agonistic antibody that specifically binds to OX40 ("anti-OX40 antibody"), wherein the anti-OX40 antibody is administered at a dose and/or frequency that is sufficient to achieve and/or maintain an OX-40 receptor occupancy of 20% to 80% in the subject for 7 days after the administration of the anti-OX40 antibody.

17. A method of stimulating an immune response in a subject with a cancer, comprising administering to the subject an agonistic antibody that specifically binds to OX40 ("anti-OX40 antibody"), wherein the anti-OX40 antibody is administered at a dose and/or frequency that is sufficient to achieve and/or maintain an OX-40 receptor occupancy of 20% to 80% in the subject for 7 days after the administration of the anti-OX40 antibody.

18. The method of claim 1, wherein the anti-OX40 antibody is administered at a dose and/or frequency that is sufficient to achieve and/or maintain an OX-40 receptor occupancy of 20% to 70% in the subject for 7 days after the administration of the anti-OX40 antibody.

19. The method of claim 1, wherein the anti-OX40 antibody is administered at a dose and/or frequency that is sufficient to achieve and/or maintain an OX-40 receptor occupancy of 20% to 60% in the subject for 7 days after the administration of the anti-OX40 antibody.

20. The method of claim 1, wherein the anti-OX40 antibody is administered at a dose and/or frequency that is sufficient to achieve and/or maintain an OX-40 receptor occupancy of 20% to 50% in the subject for 7 days after the administration of the anti-OX40 antibody.

\* \* \* \* \*